United States Patent [19]

Stirling et al.

[11] Patent Number: 4,524,073

[45] Date of Patent: Jun. 18, 1985

[54] β-LACTAM COMPOUNDS

[75] Inventors: Irene Stirling, Reigate; Gordon Bruton, Croydon; Stephen H. Calvert, Guildford; Brian P. Clarke, Kingswood, all of England

[73] Assignee: Beecham Group p.l.c., England

[21] Appl. No.: 516,121

[22] Filed: Jul. 20, 1983

[30] Foreign Application Priority Data

Jul. 22, 1982 [GB] United Kingdom ............... 8221162
Dec. 15, 1982 [GB] United Kingdom ............... 8235692

[51] Int. Cl.³ ................. A61K 31/44; A61K 31/42; A61K 31/43; C07D 499/32; C07D 498/10
[52] U.S. Cl. .............................. 514/80; 260/239.1; 260/245.3; 514/192; 514/193; 514/200; 514/210
[58] Field of Search ................. 260/245.3, 239.1; 424/246, 200, 263, 271, 272

[56] References Cited

U.S. PATENT DOCUMENTS 4,407,751 10/1983 Godtfredsen et al. ........... 260/239.1

*Primary Examiner*—Natalie Trousof
*Assistant Examiner*—Vera C. Clarke
*Attorney, Agent, or Firm*—Jacobs and Jacobs

[57] ABSTRACT

A compound of formula (I) or a pharmaceutically acceptable salt or in vivo hydrolysable ester thereof:

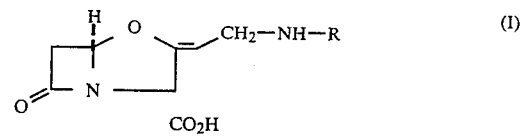

wherein R represents an alkyl or aralkyl group, substituted on an alkyl carbon atom other than that adjacent to —NH— group, with one or more functional groups selected from halogen, non-aromatic heterocyclyl linked through carbon, aromatic heterocyclyl, nitro, oxo, —OR$^1$, SR$^1$, —P(O)R$^2$R$^3$, —NR$^4$R$^5$, =NR$^6$, or a sulphur linked organic radical, wherein R$^1$, R$^2$, R$^3$, R$^4$, R$^5$ and R$^6$ are various organic radicals.

Processes for the preparation of these compounds and pharmaceutical compositions containing them are also disclosed.

46 Claims, No Drawings

β-LACTAM COMPOUNDS

This invention relates to novel β-lactam containing compounds, their preparation and their use, and in particular to a novel class of clavams. These compounds have antibacterial and β-lactamase inhibitory properties, and therefore are of use in the treatment of bacterial infections in humans and animals either alone or in a synergistic composition with other β-lactam antibacterial agents, such as penicillins and cephalosporins.

In particular, this invention relates to a class of secondary amino derivatives of clavulanic acid containing a functionally substituted alkyl group.

Clavulanic acid has the structure:

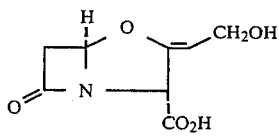

and is described in British Pat. No. 1508977.

The present invention provides a compound of formula (I) or a pharmaceutically acceptable salt or in vivo hydrolysable ester thereof;

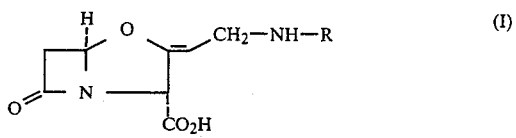

wherein R represents an alkyl or aralkyl group, substituted on an alkyl carbon atom other than that adjacent to —NH— group, with one or more functional groups selected from halogen, non-aromatic heterocyclyl linked through carbon, aromatic heterocyclyl, nitro, oxo, —OR$^1$, SR$^1$, —P(O)R$^2$R$^3$, —NR$^4$R$^5$, =NR$^6$, or a sulphur linked organic radical;

R$^1$ represents hydrogen or a carbon linked organic radical or two of said R$^1$ groups may be joined to form a ring;

R$^2$ and R$^3$ independently represent hydroxy or a hydrocarbon or hydrocarbyloxy group;

R$_4$ represents hydrogen or a hydrocarbon group;

R$^5$ represents hydrogen or a carbon linked organic radical or a sulphur linked organic radical;

R$^6$ represents hydroxy, hydrocarbon, hydrocarbyloxy, amino, arylamino, or a group —NHCONH$_2$;

provided that a carbon atom of the group R which carries an oxo substituent does not carry a second substituent other than a group —NR$^4$R$^5$.

The group R may have for example up to three substituent groups, suitably two substituent groups, and preferably one substituent group.

When R is an alkyl group, it may be straight or branched chain and may contain, for example, from 2 to 12 carbon atoms, suitably from 2 to 6 carbon atoms. In particular the group R may be substituted ethyl, n-, or iso-propyl, or n-, sec-, iso- or tert-butyl. A substituted ethyl group is preferred.

Suitable aralkyl groups for R include those with 2-6 carbon atoms in the substituted alkyl moiety and an unsubstituted aryl moiety such as phenyl. In particular R may be phenyl ethyl substituted on the ethyl chain.

The term 'halogen' refers to fluorine, chlorine, bromine and iodine.

Suitable 'carbon linked organic radicals' include an optionally substituted hydrocarbon, heterocyclic group, or a group —COR$^H$, CO$_2$R$^H$ or CON(R$^H$)$_2$ where R$^H$ represents hydrogen or a hydrocarbon or heterocyclic group.

Suitable 'sulphur linked organic radicals' include a group —S(O)$_n$R$^S$ where n is one or two, and R$^S$ is hydroxy or an optionally substituted hydrocarbon, hydrocarbyloxy or heterocyclic group, or R$^S$ is a group —NR$^T$R$^U$ where R$^T$ and R$^U$ are independently hydrogen or optionally substituted hydrocarbon, or R$^T$ and R$^U$ together form the residue of a heterocyclic ring.

The term 'hydrocarbon' includes groups having up to 18 carbon atoms, suitably up to 10 carbon atoms, conveniently up to 6 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, aryl, and aryl(C$_{1-6}$)alkyl.

Suitable alkyl groups include straight and branched chain alkyl groups containing from 1 to 6 carbon atoms, such as methyl, ethyl, propyl and butyl. A particular alkyl group is methyl.

The term 'heterocyclyl' includes single or fused rings comprising up to four hetero atoms in the ring selected from oxygen, nitrogen and sulphur and optionally substituted with up to three halogen, C$_{1-6}$ alkyl, C$_{1-6}$ alkoxy, halo-(C$_{1-6}$)-alkyl, hydroxy, amino, carboxy, C$_{1-6}$ alkoxycarbonyl, C$_{1-6}$ alkoxycarbonyl(C$_{1-6}$)alkyl, aryl or oxo groups.

The heterocyclic groups may be aromatic or non-aromatic. Non-aromatic heterocyclic groups are linked through a carbon atom. Aromatic heterocyclic groups may be linked through carbon or nitrogen.

Suitably the heterocyclic ring comprises from 4 to 7 ring atoms, preferably 5 to 6 atoms.

Suitable aromatic heterocyclic groups include imidazolyl, triazole, tetrazole, furyl, thienyl, pyrrolyl, N-methylpyrrolyl, pyridyl, indolyl, oxazolyl, thiazolyl, quinolyl.

When used herein the term 'aryl' includes phenyl and naphthyl optionally substituted with up to five halogen, C$_{1-6}$ alkyl, C$_{1-6}$ alkoxy, halo(C$_{1-6}$)alkyl, hydroxy, amino, nitro, carboxy, C$_{1-6}$ alkoxycarbonyl, or C$_{1-6}$ alkoxycarbonyl-(C$_{1-6}$)-alkyl groups.

Suitable optional substituents for the hydrocarbon, heterocyclic groups and organic radicals include C$_{1-6}$ alkyl, heterocyclic, amino, C$_{1-6}$ alkanoylamino, mono, di- and tri-(C$_{1-6}$)alkylamino, hydroxy, C$_{1-6}$ alkoxy, mercapto, C$_{1-6}$ alkylthio, heterocyclylthio, arylthio, sulphamoyl, carbamoyl, amidino, quanidino, nitro, chloro, bromo, fluoro, carboxy and salts and esters thereof, C$_{1-6}$ alkanoyloxy, arylcarbonyl and heterocyclylcarbonyl.

Specific groups —OR$^1$ are hydroxy, C$_{1-6}$ alkoxy, in particular methoxy; and C$_{1-6}$ alkanoyloxy, in particular acetoxy.

The group —OR$^1$ may also conveniently represent the residue of a β-lactam antibiotic, such as a penicillin or cephalosporin. In particular the group —OR$^1$ may represent a group of formula (A):

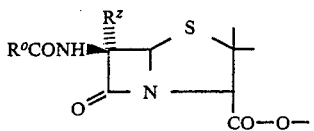
(A)

wherein R⁰CONH— represents an organic acylamino group of an antibacterially active penicillin, and $R^z$ represents hydrogen or methoxy. In particular $R^o$ may represent a group of formula (B):

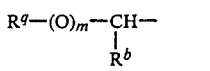
(B)

where $R^q$ represents aryl, m is zero or 1, and $R^b$ represents hydrogen, amino, carboxy or an ester thereof, acylamino such as acetamino, or ureido.

Specific examples of suitable groups (B) include
phenylacetamido;
phenoxyacetamido;
α-aminophenylacetamido;
α-amino-p-hydroxyphenylacetamido;
α-carboxyphenylacetamido;
α-phenoxycarboxylphenylacetamido;
α-(o-, m, or p-)methylphenoxycarbonylphenylacetamido;
α-carboxythien-3-ylacetamido;
α-phenoxycarbonylthien-3-yl;
α-(o-, m-, or p-)methylphenoxycarbonylthienyl-3-ylacetamido.

Preferably $R^z$ represents methoxy when $R^b$ is carboxy or an ester thereof.

A preferred halogen substituent for the alkyl group R is chloro.

Specific groups —$SR^1$ are $C_{1-6}$alkylthio, in particular methylthio, and arylthio in particular phenylthio.

Specific groups —$P(O)R^2R^3$ are those wherein $R^2$ and $R^3$ are $C_{1-6}$ alkoxy, in particular the group

Specific groups —$NR^4R^5$ are amino(—$NH_2$)($C_{1-6}$)alkoxycarbonylamino, such as methoxycarbonylamino (—$NHCO_2CH_3$)($C_{1-6}$)alkylsulphonamido, such as methylsulphonylamido(—$NHSO_2CH_3$), ($C_{1-6}$)alkylureidoamino such as dimethylureidoamino(—NHCONMe₂).

Specific sulphur linked organic radicals include sulphonato or salts or esters thereof. The salts may be pharmaceutically acceptable and the esters may be in-vivo hydrolysable as described hereinafter. However, non-pharmaceutically acceptable salts such as the lithium salt may be employed as intermediates in the production of the free acid, pharmaceutically acceptable salts or in-vivo hydrolysable ester of formula I.

When two of the groups $R^1$ are joined, they may together suitably represent divalent radicals of formula —O—$(CH_2)_p$—O—, —S—$(CH_2)_p$—S—, or —O—$(CH_2)_p$—S— wherein p is from 1 to 6, preferably 2 or 3.

When the alkyl group R contains two substituents, they may be on the same or different carbon atoms. For example, suitably two $C_{1-6}$ alkoxy substituents are present on one carbon atom of the group R, in particular two methoxy groups, or an oxo and —$NR^4R^5$ group may be present on the same carbon atom of the group R to form a carbamoyl group.

The carboxylic free acid form of the compound of formula (I) may be in the form of the Zwitterion.

Examples of suitable pharmaceutically acceptable in vivo hydrolysable ester groups include those which break down readily in the human body to leave the parent acid or its salts, for example acyloxyalkyl groups, such as acetoxymethyl, pivaloyloxymethyl, α-acetoxyethyl and α-pivaloyloxyethyl groups; alkoxycarbonyloxyalkyl groups, such as ethoxycarbonyloxymethyl and α-ethoxycarbonyloxyethyl; dialkylaminoalkyl groups, such as dimethylaminomethyl, dimethylaminoethyl, diethylaminomethyl or diethylaminoethyl; and lactone groups such as phthalidyl or dimethoxyphthalidyl.

Esters of the compound of the formula (I) may be presented in the form of their acid addition salts if desired. The acid used to form the salt will most suitably be pharmaceutically acceptable, but non-pharmaceutically acceptable acid addition salts are also envisaged, for example as intermediates in the preparation of the pharmaceutically acceptable salts by ion exchange. Suitable pharmaceutically acceptable acid addition salts include those of inorganic and organic acids, such as hydrochloric, phosphoric, sulphuric, methanesulphonic, toluenesulphonic, citric, malic, acetic, lactic, tartaric, propionic and succinic acid.

Most suitably the acid addition salt is provided as a solid and preferably as a crystalline solid.

Compounds of this invention when in crystalline form may be solvated, for example hydrated.

Suitable pharmaceutically acceptable salts of the compounds of formula (I) include metal salts, eg aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidien, N-benzyl-β-phenethylamine, dehydroabietylamine, N,N'-bisdehydroabietylamine, ethylenediamine, or bases of the pyridine type such as pyridine, collidine or quinoline.

Specific compounds of this invention include the following, and salts and esters thereof:
9-N-(2,2-dimethoxyethyl)aminodeoxyclavulanic acid;
9-N-(2-chloroethyl)aminodeoxyclavulanic acid;
9-N[2(N-methoxycarbonylamino)ethyl]amino-9-deoxyclavulanic acid;
9-N-(2-pyrid-2'-ylethyl)aminodeoxyclavulanic acid;
9-N-(2-pyrid-4'-ylethyl)aminodeoxyclavulanic acid;
9-N(2-methoxyethyl)aminodeoxyclavulanic acid;
9-N-[(N'-benzyl-N'-methylsulphonamido)ethyl]aminodeoxyclavulanic acid;
9-N-(2-diethyloxyphosphorylethyl)aminodeoxyclavulanic acid;
9-N-[4-(sulphonato)butyl]aminodeoxyclavulanic acid;
9-N(2-phenylthioethyl)aminodeoxyclavulanic acid;
9-N-2[(N,N-dimethylsulphamoyl)benzylamino]ethylaminodeoxyclavulanic acid;
9-N-(2-methylsulphonamidoethyl)amionodeoxyclavulanic acid;
9-N-(3-methylsulphonamidopropyl)aminodeoxyclavulanic acid;

9-N-[2-(N-methyl)methylsulphonamidoethyl-]aminodeoxyclavulanic acid;
9-N-[2-[6β-(DL-2-Phenoxycarbonyl-2-thien-3'-ylacetamido)penicillanoyloxy]ethyl]aminodeoxyclavulanic acid;
9-N-[2-[6β-(DL-2-Phenoxycarbonyl-2-thien-3-ylacetamido)penicillanoyloxy]ethyl]aminodeoxyclavulanic acid;
9-N-[2-[6β-(DL-2-Phenoxycarbonyl-2-thien-3'-yl acetamido)penicillanoyloxy]ethyl]-N-(2-methallyl-)aminodeoxyclavulanic acid;
9-N-[3-Imidazol-1-yl)propyl]aminodeoxyclavulanic acid;
9-N-(4,4-Diethoxybutyl)amino deoxyclavulanic acid;
9-N-(4-Acetoxybutyl)aminodeoxyclavulanic acid;
9-N-[4-Methyl-4-nitropentyl]aminodeoxyclavulanic acid;
9-[N-benzyl-N-(N'N'-dimethylureido)ethyl]aminodeoxyclavulanic acid and 9-N-(N"-dimethylureido)ethylaminodeoxyclavulanic acid;
9-N-[2-(phenylsulphonyl)ethyl]aminodeoxyclavulanic acid;
9-N-(3-N-benzylcarbamoylprop-1-yl)aminodeoxyclavulanic acid;
9-N-(3-N-Benzylcarbamoyleth-1-yl)aminodeoxyclavulanic acid;
9-N-(2-Indol-3'-ylethyl)aminodeoxyclavulanic acid;
9-N-(2-chloro-2-phenylethyl)-aminodeoxyclavulanic acid;
9-N-(2-carbamoylethyl)aminodeoxyclavulanic acid.

The compounds of the present invention may be prepared by a process which comprises removing a group $R^x$ from a compound of the formula (II):

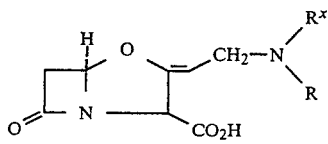
(II)

or a salt or ester thereof wherein R is as defined in relation to formula (I) and $R^x$ is a removable protecting group, and optionally thereafter converting the product to a salt or ester as necessary.

Suitably the group $R^x$ is one which may be removed by hydrogenation, for example $R^x$ may be a group $R^a$ where $R^a$ represents

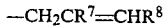

wherein $R^7$ is a hydrogen atom or $C_{1-6}$ alkyl group and $R^8$ is a hydrogen atom, a $C_{1-6}$ alkyl group, or a phenyl group optionally substituted by a $C_{1-6}$ alkoxy group; or $R^7$ and $R^8$ together with the carbon atoms to which they are joined represent a phenyl group.

Suitably also $R^x$ may be arylmethoxycarbonyl, in particular benzyloxy-carbonyl.

Particularly suitable groups $R^a$ include the following:
$CH_2CH=CHCH_3$, $CH_2CH=CHC_6H_5$,
$CH_2C(CH_3)=CH_2$, $CH_2C(C_2H_5)=CH_2$,
$CH_2C(nC_3H_7)=CH_2$, $CH_2C(CH_3)=CHCH_3$,
$CH_2C(CH_3)=C(CH_3)_2$, $CH_2C(CH_3)=CHC_2H_5$,
$CH_2C(CH_3)=CHC_6H_5$ and $CH_2C_6H_5$.

Favoured groups $R^a$ are $CH_2CH=CHCH_3$, $CH_2CH=CHC_6H_5$, $CH_2C(CH_3)=CH_2$, $CH_2C(CH_3)=CHC_6H_5$ and $CH_2C_6H_5$.

A preferred group $R^a$ is $CH_2C_6H_5$.

The hydrogenation is normally carried out in the presence of a transition metal catalyst, such as palladium, for example in the form of palladium on carbon (charcoal), palladium on barium sulphate, palladium on calcium carbonate, and palladium black.

A favoured catalyst is palladium on carbon (sometimes referred to as palladium on charcoal); for example 5%, 10%, 20% or 30% palladium on carbon.

A low, medium or high pressure of hydrogen may be used in this reaction, for example from 1 to 6 atmospheres.

The reaction is normally carried out at a non-extreme temperature, for example from 0° C. to 30° and more usually from 12° C. to 25° C. It is generally convenient to carry out the reaction at ambient temperature.

Suitable solvents for carrying out the hydrogenation include ethanol, n-propanol, isopropanol, tetrahydrofuran, dioxan, ethyl acetate or mixtures of such solvents or such solvents in the presence of water. A favoured solvent is ethanol.

It is often preferable to carry out the hydrogenation reaction on a hydrogenolysable ester of a compound of the formula (II), for example a benzyl ester, so that a compound of the formula (I) per se is formed by the hydrogenation. Such hydrogenation reactions proceed at least in part via the formation of a compound of the formula (II). Favoured hydrogenolysable esters include benzyl and substituted benzyl esters such as methoxybenzyl, nitrobenzyl (for example the p-nitrobenzyl ester), chlorobenzyl and bromobenzyl esters. A particularly suitable hydrogenolysable ester is the p-methoxybenzyl ester. Further favoured hydrogenolysable ester groups include those groups $CH_2CR^7=CHR^8$ that have been specified hereinbefore as being favoured for removal from a nitrogen atom by hydrogenolysis.

When $R^x$ is aryl-methoxycarbonyl, hydrogenation of the compound an ester of formula II in the presence of acid yields the ester acid addition salt of the compound of formula I.

The product may be isolated by methods known in the art.

The compounds of the invention may also be prepared by a process which comprises reacting a compound of the formula (III) or a salt or ester thereof:

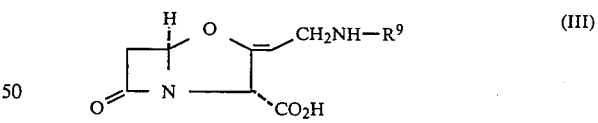
(III)

wherein $R^9$ is a hydrogen atom or an amino protecting group; with a compound of the formula R—Z; wherein R is as defined in relation to formula (I) and Z is a readily displaceable group, removing any group $R^9$ that is not hydrogen, and optionally thereafter converting the product to a salt or ester as necessary.

Preferably $R^9$ is hydrogen, but it may conveniently be a silyl group such as trimethylsilyl or a group of formula $R^a$ above.

Preferably compound (III) is employed in the ester form, suitably a silyl ester.

Suitable groups Z include halides, for example bromide and iodide, and sulphonate esters, for example alkyl sulphonates and arylsulphonates, such as methanesulphonate; benzenesulphonate, p-toluenesulphonate and p-bromobenzenesulphonate. Preferably Z is iodide.

The reaction of the compound of the formula (III) with the compound of formula R—Z is conveniently carried out in an inert organic solvent such as dimethylformamide, acetonitrile or dichloromethane, preferably in the presence of a strong non-nucleophilic organic base such as diazabicyclononene or diazabicycloundecane at a non-extreme temperature for example −10° C. to +50° C., more usually −50° C. to +20° C. and most conveniently in the range −5° C. to +10° C.

Esters of formula (I) may be prepared by esterification of a carboxylic acid of formula (I) or a salt or other reactive derivative of the acid with an alcohol or an esterifying derivative thereof. Esterification may be performed by any suitable method, for example, by reaction of a salt of the free acid:

(a) with the appropriate halide, tosylate, mesylate sulphate or alkyl oxonium salt of the alcohol in the presence of a solvent such as dimethylsulphoxide, dimethylformamide, hexamethylphosphoramide, dichloromethane or ethyl acetate;

(b) by phase transfer catalysis methods with the halide and/or sulphate of the alcohol in aqueous and/or organic solution in the presence of a quaternary ammonium salt such as tetrabutyl ammonium bisulphate or halide, or benzyltrimethyl ammonium halide.

The compounds of the formula (II) where $R^x$ is a group $R^a$ may be prepared by the reaction of an ester of a compound of the formula (IV) or (V):

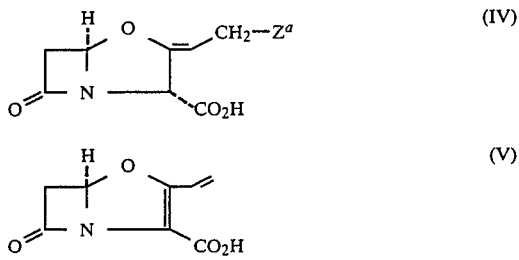

wherein $Z^a$ is a displaceable group; with an amine of the formula (VI):

$$R^a—NH—R \qquad (VI)$$

wherein $R^a$, and R are as hereinbefore defined.

Suitable groups $Z^a$ include halogen, for example chlorine or bromine, alkyl- or arylsulphonyloxy, or acyloxy such as optionally substituted $C_{1-6}$ alkanoyloxy, for example acetoxy, chloroacetoxy, chloroacetoxy, dichloroacetoxy, trichloroacetoxy, or sulphate.

Suitably the reaction of the amine of the formula (VI) with the compound of the formula (IV) or (V) will take place in an aprotic solvent such as acetonitrile or dimethylformamide at a non-extreme temperature, for example −50° to +50°, more usually −5° to +25°, and conveniently within the range 0° to +20°.

Compounds of formula (II) or an ester thereof where $R^x$ is arylmethyloxycarbonyl, may be prepared by reacting a compound of formula (I) with a compound of formula:

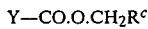

where $R^c$ represents aryl and Y is a readily displaceable group.

Favoured groups Y include the chlorine and bromine atom, and sulphonate and carboxylate esters.

The compounds of the formula (III) where $R^9$ is hydrogen may be prepared by the methods of French Patent Application Publication No. 2353556.

The compounds of formula (III) where $R^9$ is a group $R^a$ may be prepared by the reaction of a compound of the formula (III) or salt or ester thereof wherein $R^9$ is hydrogen with a compound of the formula $R^a$—Z wherein $R^a$ and Z are as hereinbefore defined.

The present invention also provides a pharmaceutical composition which comprises a compound of this invention and a pharmaceutically acceptable carrier.

The compositions of the invention include those in a form adapted for oral, topical or parenteral use and may be used for the treatment of the infection in animals especially mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrant and the like in accordance with conventional pharmaceutical practice in the manner well understood by those skilled in the art of formulating antibiotics.

The injectable solution of the compound of this invention may be made up in a sterile pyrogen-free liquid such as water, aqueous ethanol or the like.

An alternative approach to administering the compounds of this invention is to utilise an injectable suspension. Such suspensions may be made up in sterile water; sterile saline or the like and may also contain suspending agents such as polyvinylpyrrolidone, lecithin or the like. For use in such suspensions the zwitterionic compounds of this invention should be in the form of fine particles.

The compositions may contain from 0.1% by weight, preferably from 10–60% by weight, of the active material, depending on the method of administration. Where the composition comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

The compound of the formula may be present in the composition as sole therapeutic agent or it may be present together with other therapeutic agents such as, for example, a penicillin or cephalosporin. Considerable advantages accrue from the inclusion of a penicillin or cephalosporin which shows instability to β-lactamases since the resulting composition shows enhanced effectiveness (synergy). Suitable penicillins, cephalosporins or other β-lactam antibiotics for inclusion in such synergistic compositions include not only those known to be highly susceptible to β-lactamases but also those which have a degree of intrinsic resistance to β-lactamases.

Suitable penicillins for inclusion in the compositions of this invention include benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, sulbenicillin, piperocillin, and other well known penicillins including prodrugs thereof such as their in vivo hydrolysble esters such as the acetoxymethyl, pivaloyloxymethyl, α-ethoxycarbonyloxyethyl or phthalidyl esters of ampicillin benzylpenicillin or amoxycillin, and aldehyde or ketone adducts of penicillins containing a 6-α-aminoacetamide side chain (such as hetacillin, metampicillin and analogous derivatives of amoxycillin) or α-esters of carbenicillin or ticarcillin such as their phenyl or indanyl α-esters.

Suitable cephalosporins for inclusion in the compositions of this invention include, for example, cefatrizine, cephaloridine, cephalothin, cefazolin, cephalexin, cephacetrile, cephapirin, cephamandole nafate, cephradine, 4-hydroxycephalexin, cefaparole, cephaloglycin, cefoperazone, and other well known cephalosporins or prodrugs thereof.

Highly favoured penicillins for use in the compositions of this invention include ampicillin, amoxycillin, carbenicillin and ticarcillin. Such penicillins may be used as a pharmaceutically acceptable salt such as the sodium salt. Alternatively the ampicillin or amoxycillin may be used in the form of fine particles of the zwitterionic form (generally as ampicillin trihydrate or amoxycillin trihydrate) for use in an injectable suspension, for example, in the manner hereinbefore described for a compound of this invention.

The preferred penicillin for use in the synergistic composition is amoxycillin, for example as its sodium salt or trihydrate.

Particularly suitable cephalosporins for use in the compositions of this invention include cephaloridine and cefazolin which may be in the form of a pharmaceutically acceptable salt, for example the sodium salt.

When present together with a cephalosporin or penicillin, the ratio of a compound of the invention to the penicillin or cephalosporin agent may vary over a wide range of ratios, such as from 10:1 to 1:10, for example about 3:1, 2:1, 1:1, 1:2, 1:3, 1:4, 1:5 or 1:6 (wt/wt, based on pure free antibiotic equivalent).

The present invention also provides a method of treating bacterial infections in animals, in particular humans or domestic mammals, which comprises the administration of a composition of this invention Commonly the infection treated will be due to a strain of *Staphylococcus aureus, Klebsiella aerogenes, Escherichia coli, Proteus* sp., *Bacteroides fragilis* or the like. The organisms believed to be most readily treated by an antibacterially effective amount of a compound of this invention is *Staphylococcus aureus*. The other organisms named are more readily treated by using a synergistically effective amount of the compound of this invention and a penicillin or cephalosporin. The administration of the two components may take place separately but in general we prefer to use a composition containing both the synergist and the penicillin or cephalosporin.

The indications for treatment include respiratory tract and urinary tract infections in humans.

The following Examples illustrate the present invention.

EXAMPLE 1

9-N-(2,2-Dimethoxyethyl)amino deoxyclavulanate

Benzyl 9-N-(2,2-dimethoxyethyl)-N-2-methallylamino deoxyclavulanate (1.15 g) in ethanol (15 cm$^3$) was hydrogenolysed at atmospheric pressure in the presence of 10% palladium on carbon (0.4 g) for ¾ hour. The catalyst had been prehydrogenated for ten minutes. The catalyst was filtered off, washed with ethanol (30 cm$^3$) and then separately with aqeuous ethanol (30 cm$^3$). The aqueous washings were evaporated to afford a white crystalline solid. Washing with ethanol and drying afforded 220 mg of the title compound. The original filtrate and ethanolic washings were evaporated to give an oil. Ethanol was added forming a further 97 mg of the title compound as a white crystalline solid. Total yield 0.32 g (41%). ν (KBr) 1790, 1690, 1600, 1460, 1392, 1300, 1195, 1125, 1082, 1042, 1020, 955, 918, 894, 750 cm$^{-1}$. δ (D$_2$O) 3.15 (1H, d, J 17 Hz, 6βCH partially obscured), 3.17 (2H, d, J 5 Hz, CH$_2$CH(OCH$_3$)$_2$), 3.47 (6H, s, 2×OC$\underline{H}_3$), 3.58 (1H, dd, J 17 and 3 Hz, 6αC$\underline{H}$), 3.73 and 3.81 (2H, d ABq, J 13 and 8 Hz, 9C$\underline{H}_2$), 4.73 (1H, t, J 5 Hz, CH$_2$C$\underline{H}$(OCH$_3$)$_2$), 8CH obscured by HOD at 4.85, 5.03 (1H, s, 3CH) 5.79 (1H, d, J 3 Hz, 5αC$\underline{H}$).

Preparation 2a

N-Benzyl-N-(2-chloroethyl)amine

N-Benzyl ethanolamine (15.1 g, 100 mmol) was stirred in benzene (160 ml) at room temperature. Thionyl chloride (30 ml) was added dropwise over ten minutes. A white precipitate began to form immediately and the reaction mixture was warmed to 80° C. for 30 minutes. After cooling to room temperature the white solid was filtered off, washed with ether and dried. This solid was neutralised with sodium hydroxide solution and extracted with ethylacetate, washed with brine, dried (MgSO$_4$) and evaporated to a yellow oil which was chromatographed on silica gel. Elution with petrol/ethylacetate: 1/1 afforded the title amine as a colourless oil, yield 6.75 g (40%).

N.M.R. (CDCl$_3$). 1.90 (s, D$_2$O exch.), 2.82 (2H, t, J 7 Hz), 3.50 (2H, t, J 7 Hz), 3.70 (2H, s) and 7.30 (5H, s, C$_6$H$_5$).

Preparation 2b

Benzyl 9-N-benzyl-N-(2'-chloroethyl)aminodeoxyclavulanate

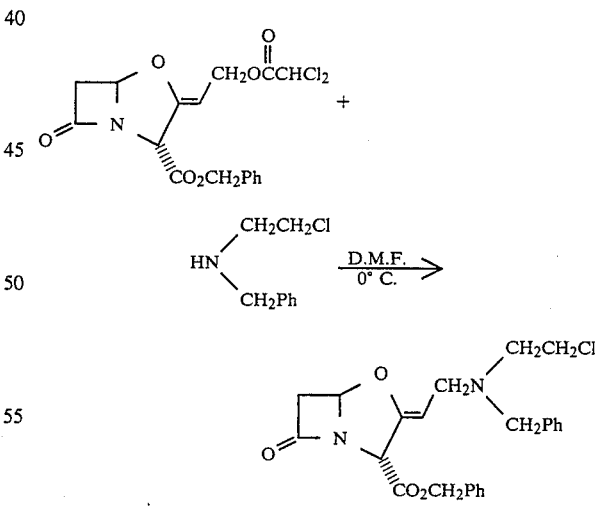

N-Benzyl-N-(2'-chloroethyl)amine (6.5 g, 38 mmol) in dry dimethylformamide (50 ml) was added dropwise to a solution of benzyl dichloroacetylclavulanate (7.6 g, 19 mmol) in dimethylformamide (100 ml) at 0° C. After 2½ hours at this temperature the reaction mixture was poured into water and extracted with ethylacetate. The organic phase was washed with water (3×), brine (2×), dried (Mg. SO$_4$) and evaporated to low volume (~15 ml) in the presence of toluene. This solution was chromatographed on silica gel: elution-petrol/ethylacetate: 5/1 grading to 3/1, to afford the title ester as an oil. Yield 1.60 g (19%).

I.R. (CHCl$_3$) 1802, 1750, 1698, 1601 and 1305 cm$^{-1}$.

N.M.R. (CDCl$_3$). 2.71 (2H, t, J 7 Hz), 2.95 (1H, d, J 17 Hz), 3.22 (2H, d, J 7 Hz). 3.43 (1H, dd, J 17 and 3 Hz, partly obscured by signal at 3.52δ), 3.44 (2H, t, J 7 Hz), 3.52 (2H, s), 4.71 (1H, bt, J 7 Hz), 5.07 (1H, s), 5.19 (2H, s), and 3.16–3.45 (10H, m).

M.S. Observed M$^+$=440.1508. C$_{24}$H$_{25}$N$_2$ClO$_4$ requires M=440.1503.

EXAMPLE 2

9-N-(2-Chloroethyl)amino-deoxyclavulanic acid

Benzyl-9-N-benzyl-N-(2-chloroethyl)amino-deoxyclavulanate (2.67 g, 6.06 mmol) in toluene (20 ml) was extracted twice with tartaric acid (0.91 g, 6.06 mmol) in water (25 ml). The combined aqueous washings were partitioned with ethyl acetate and treated dropwise with a saturated potassium carbonate solution, with vigorous stirring, until pH 5. The ethyl acetate was separated, dried (MgSO$_4$), and evaporated. The benzyl-9N-benzyl-N-(2-chloroethyl)aminodeoxyclavulanate thus obtained (2.37 g, 5.38 mmol) in tetrahydrofuran (20 ml) was added to prehydrogenated Pd/C, 10% (0.6 g) in tetrahydrofuran (15 ml). The mixture was hydrogenated for 20 min. when thin layer chromatographic monitoring indicated the total consumption of the starting material. The hydrogenation was halted and the solution filtered and evaporated. The residue was crystallized from aqueous acetone to give the title acid (0.7 g, 50% yield).

$\nu_{max}$. (Nujol) 1796, 1696 and 1600 cm$^{-1}$.

N.m.r. (CDCl$_3$) 3.06 (1H, d, J 17 Hz, 6β—CH), 3.22–3.55 (2H, m, CH$_2$NH$^+$), 3.60–3.90 (5H, m, 9—CH$_2$, CH$_2$Cl and 6α—CH), 4.78 (1H, bt, J 7 Hz, 8—CH), 4.97 (1H, s, 3—CH) and 5.72 (1H, d, J 3 Hz, 5—CH).

Preparation 3

9-[N-Benzyl-N(N′-methoxycarbonyl-2′-aminoethyl)-]amino-9-deoxyclavulanic acid

A stirred solution of 9-N-benzylamino-9-deoxyclavulanic acid (1.0 g, 3.46 mmol) in dry dimethylformamide (20 ml) was cooled (0°) and treated with 1,5-diazobicyclo[4.3.0]non-5-ene (1.0 g, 7.92 mmol) and chlorotrimethylsilane (0.46 ml, 3.46 mmol). After a further 5 mins. N-methoxycarbonyl-2-aminoiodoethane (1.2 g) was added and the solution stirred at 0° for a further 1 hr. The reaction mixture was then stored in the freezer for 3 days.

Water (0.5 ml) was added to the reaction mixture and the solvents were removed under reduced pressure. Chromatography of the residue on silica gel, eluting with n-butanol/ethanol/water (4:1:1) gave recovered 9-N-benzylamino-9-deoxyclavulanic acid (0.18 g, 18%) followed by the title compound as a white solid (0.42 g, 31%).

$\nu_{max}$. (KBr) 1790, 1700, 1620 cm$^{-1}$.

δ (D$_2$O) 2.98 (2H, t, J 7 Hz, CH$_2$CH$_2$), 3.00 (1H, d, J 17 Hz, β-lactam CHH), 3.31 (2H, t, J 7 Hz, CH$_2$CH$_2$), 3.42 (1H, dd, J 17 and 3 Hz, β-lactam CHH), 3.53 (3H, s, OCH$_3$), 3.61 (2H, d, J 7 Hz, C(9)H), 4.02 (2H, s, NCH$_2$Ph) 4.78 (1H, t, J 7 Hz, C(8)H), 4.92 (1H, s, C(3)H), 5.67 (1H, d, J 3 Hz, β-lactam CH), 7.36 (5H, s, aryl H) ppm.

EXAMPLE 3

9-N[2(N-methoxycarbonylamino)ethyl]amino-9-deoxyclavulanic acid

A solution of 9-[N-benzyl-N-(N-′methoxycarbonyl-2′-aminoethyl)]amino-9-deoxyclavulanic acid (335 mg, 0.86 mmol) in a mixture of ethanol (15 ml) and water (15 ml) was hydrogenated over 10% Pd/C (200 mg) for 2 hrs at ambient temperature and pressure.

The reaction mixture was filtered through celite and the solvents evaporated. Trituration of the resulting gum with ether and acetone afforded the title compound as a white solid (190 mg, 74%).

$\nu_{max}$. (KBr) 1800, 1700, 1600 cm$^{-1}$.

δ (D$_2$O) 3.09 (2H, t, J 7 Hz, CH$_2$CH$_2$), 3.11 (1H, d, J 17 Hz, β-lactam CHH), 3.41 (2H, t, J 7 Hz, CH$_2$CH$_2$), 3.54 (1H, dd, J 17 and 3 Hz, β-lactam CHH), 3.62 (3H, s, OCH$_3$), 3.72 (2H, d, J 7 Hz, C(9)H), 4.80 (1H, t, J 7 Hz, vinyl H), 5.00 (1H, s, C(3)H), 5.77 (1H, d, J 3 Hz, β-lactam CH) ppm.

Preparation 4

Benzyl 9-N-(2-pyrid-2′-ylethyl)-N-methallylaminodeoxyclavulanate

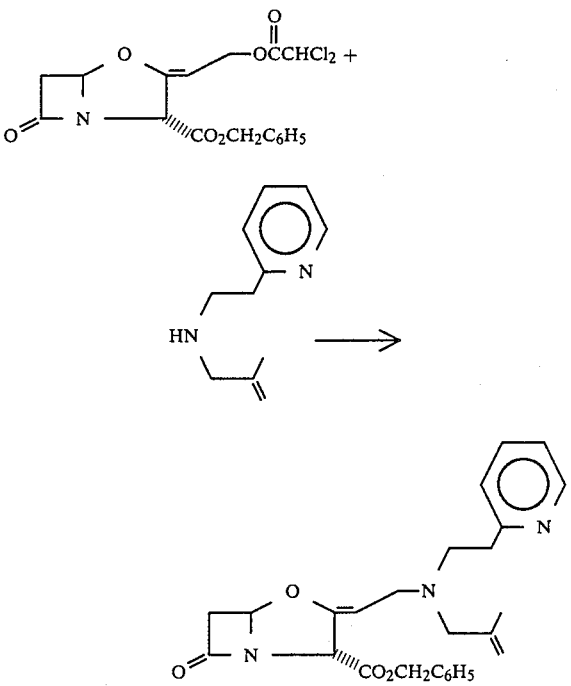

Benzyl dichloroacetylclavulanate (7.2 g) in dimethylformamide (50 cm$^3$) at −30° was treated dropwise with 1.9 equivalents of N-(2-pyrid-2′-ylethyl)-N-methallylamine in 20 cm$^3$ dimethylformamide over several minutes whilst stirring vigorously. Stirring was continued for 3 hours, allowing the temperature to rise to +10°. The mixture was poured into ethyl acetate (300 cm$^3$) and washed with water (3×100 cm$^3$) and saturated brine (5×100 cm$^3$), dried (anhydrous magnesium sulphate) and evaporated to an oil. This oil was chromatographed on silica gel eluting with ethyl acetate-cyclohexane (1:1). Fractions were collected containing the title compound Rf (SiO$_2$/ethyl acetate-cyclohexane; 1:1)=0.5, and combined fractions were evaporated to

EXAMPLE 4

9-N-(2-Pyrid-2'-ylethyl)aminodeoxyclavulanic acid

Benzyl 9-N-(pyrid-2'-ylethyl)-N-methylallylaminodeoxyclavulanate (0.4 g) in ethanol (5 cm$^3$) was hydrogenolysed at atmospheric pressure in the presence of 10% palladium on carbon (300 mg) for 2 hours. The catalyst was filtered off, washed with aqueous ethanol (100 cm$^3$) and the aqueous washings evaporated to an oil. Ethanol (3 cm$^3$) was added and the solution was cooled; crystals formed which were filtered off, washed with cold ethanol and dried to afford 23 mg of the title compound as a crystalline solid; Rf (SiO$_2$/ethyl acetate-ethanol-water; 5:4:3)=0.44 (detection by aqueous potassium permanganate spray) ν (Nujol) 1795, 1695, 1610, 1585, 1297, 1185, 1040, 1018, 915, 892, 790, 750 cm$^{-1}$. ν (KBr) 1790, 1692, 1615, 1587, 1470, 1435, 1398, 1303, 1190, 1125, 1045, 1020, 920, 895, 792, 750 cm$^{-1}$. δ (D$_2$O) 3.11 (1H, d, J 17 Hz, 6βC$\underline{H}$), 3.17 (2H, t, J 5 Hz, NC$\underline{H_2}$CH$_2$), 3.41 (2H, t, J 5 Hz, $\overline{N}$CH$_2$C$\underline{H_2}$), 3.56 (1H, dd, J 17 and 3 Hz, 6αC$\underline{H}$), 3.73 and 3.80 (2H, d ABq, 12 and 7 Hz, 9C$\underline{H_2}$), 8C$\underline{H}$ obscured by HOD, 5.02 (1H, s, 3C$\underline{H}$), 5.76 (1$\overline{H}$, d, J $\overline{3}$ Hz, 5αC$\underline{H}$),

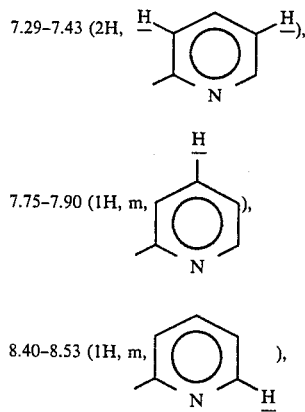

Preparation 5

Benzyl 9-N-(2-pyrid-4'-ylethyl)-N-methallylaminodeoxyclavulanate

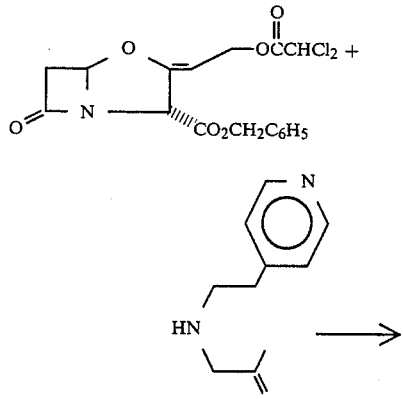

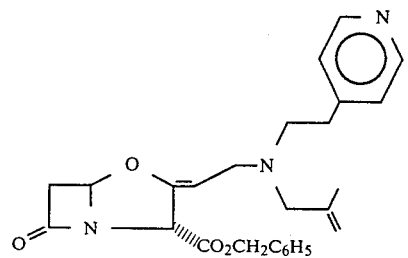

Benzyl dichloroacetylclavulanate (7.18 g; 18 mmol) in dimethylformamide (50 cm$^3$) at −30°, was treated dropwise with 1.9 equivalents of N-(2-pyrid-4'-ylethyl)-methallylamine (6 g) in dimethylformamide (20 cm$^3$) over several minutes. Stirring was continued for 1½ hours at −20° to +15° C., when the mixture was poured into ethyl acetate (300 cm$^3$) and washed with water (3×100 cm$^3$) and saturated brine (5×100 cm$^3$), dried (anhydrous magnesium sulphate) and evaporated to an oil. This crude product was hydrogenolysed to afford the secondary amine zwitterion.

EXAMPLE 5

9-N-(2-Pyrid-4'-ylethyl)amino deoxyclavulanic acid

Benzyl 9-N-(2-pyrid-4'-ylethyl)-N-methallylaminodeoxyclavulanate (crude) was hydrogenolysed in ethanol (50 cm$^3$) in the presence of 2 g 10% palladium on carbon for 5 hours. The catalyst was filtered off and washed with aqueous ethanol (50 cm$^3$), the filtrate was evaporated to afford an off-white crystalline solid from ethanol. This product was recrystallised from warm aqueous ethanol to afford the title compound as a colourless crystalline zwitterionic solid, yield = 100 mg Rf (SiO$_2$/ethylacetate-ethanol-water, 5:4:3)=0.36 (detection by aqueous potassium permanganate spray). ν (Nujol) 1795, 1690, 1600, 1590 (shoulder), 1305, 1190, 1120, 1050, 1015, 1002, 920, 895, 805 cm$^{-1}$. ν (KBr) 1795, 1692, 1600 (broad), 1475, 1420, 1400, 1377, 1305, 1192, 1185, 1118, 1047, 1015, 1005, 976, 918, 895, 805, 782, 757 cm$^{-1}$.

δ (D$_2$O/DMSO) [2.88 (2H, t, J 7 Hz) and 3.12 (2H, t, J 7 Hz)

2.94 (1H, d, J 17 Hz, 6βC$\underline{H}$), 3.44 (1H, dd, J 17 and 3 Hz, 6αC$\underline{H}$), 3.55 (2H, d, J $\overline{7}$ Hz, 9C$\underline{H_2}$), 8CH obscured by HOD, 4.72 (1H, broad s, 3C$\underline{H}$), 5.62 (1H, d, J 3 Hz, 5αC$\underline{H}$),

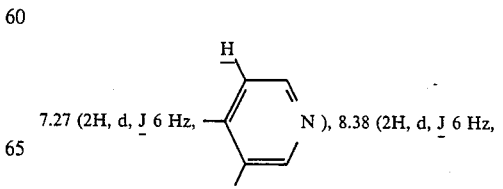

-continued

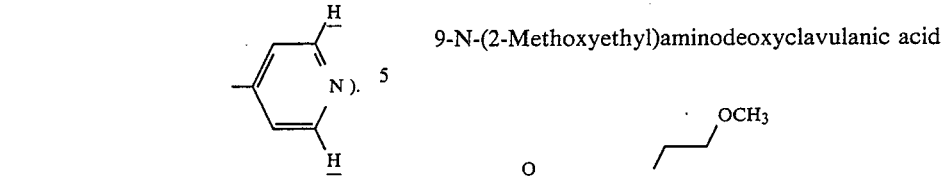

Preparation 6

Benzyl 9-N-(2-methoxyethyl)-N-(2-methallyl)aminodeoxyclavulanate

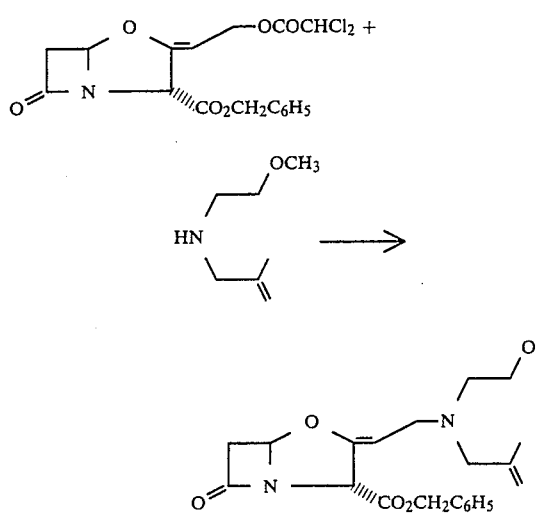

Benzyl 9-O-dichloroacetylclavulanate (18.5 g; 46.3 mmol) in dry dimethylformamide (100 cm³) was treated at −30° with 1.9 equivalents of (2-methoxyethyl)-N-(2-methallyl)amine (11.4 g) in dimethylformamide (20 cm³), dropwise, over 45 minutes between −30° and −20°. The mixture was stirred for a further 45 minutes between −20° and −10°. The mixture was poured into ethylacetate (400 cm³) and was washed with water (5×100 cm³) and saturated brine (5×100 cm³). The ethyl acetate phase was dried and evaporated to low volume. This concentrated solution was applied to a silica chromatographic column and eluted with ethylacetatecyclo-hexane (1:2). Fractions were collected containing the title compound, Rf (S:O₂/ethyl acetate-cyclohexane (1:2)=0.5 (detection by aqueous potassium permanganate spray).

Combined fractions were evaporated to an oil, yield=1.9 g (10%) σ (film) 1805, 1755, 1700, 995, 745, 700 cm⁻¹, δ (CDCl₃) 1.68 (3H, s, C=C—C$\underline{H}_3$), 2.50(2H, t, J 6 Hz, CH₂C$\underline{H}_2$N), 2.87 (2H,s,NC$\underline{H}_2$C=C), 2.97(1H, d, J 17 Hz, 6βC$\underline{H}$), 3.18(2H, d, J 7 Hz, 9C$\underline{H}_2$), 3.39(2H, t, J 6 Hz, CH₂C$\underline{H}_2$O), 3.42(1H, dd, J 17 and 3 Hz, 6αC$\underline{H}$), 4.70(1H, dt, J 7 and 1 Hz, 8C$\underline{H}$), 4.80(2H, broad s, C=C$\underline{H}_2$), 5.05(1H, d, J 1 Hz, 3C$\underline{H}$), 5.16(2H, s, CO₂C$\underline{H}_2$C₆H₅), 5.62(1H, d, J 3 Hz, 5αC$\underline{H}$), 7.33(5H, s, CH₂C₆$\underline{H}_5$).

EXAMPLE 6

9-N-(2-Methoxyethyl)aminodeoxyclavulanic acid

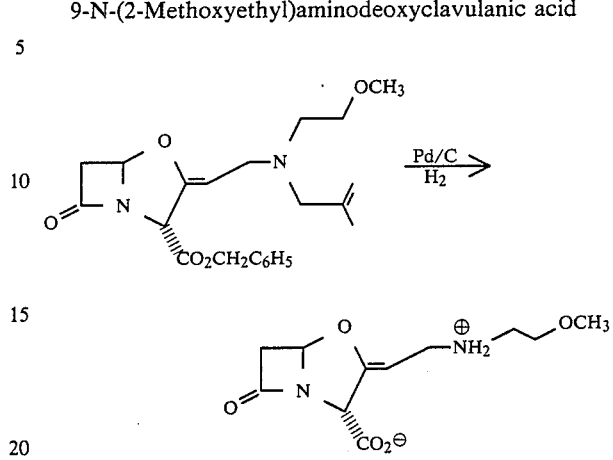

Benzyl 9-N-(2-methoxyethyl)-N-(2-methallyl)aminodeoxyclavulanate (1.85 g; 4.62 mmol) in ethanol (20 cm³) was hydrogenolysed at atmospheric pressure in the presence of 0.6 g 10% palladium on carbon (which had been prehydrogenated) for ½ hour. The catalyst was filtered off and washed with ethanol (50 cm³), then separately with water (70 cm³).

The aqueous wash was evaporated to afford colourless crystals from ethanol, yield=0.51 g (43%) Rf (Si-O₂/ethylacetate-isopropanol-water; 5:4:2)=0.34 (detection by aqueous potassium permanganate spray). ν (nujol) 1807, 1695, 1605, 1302, 1190, 1130, 1105, 1050, 1022, 1008, 950, 922, 895, 807 cm⁻¹.

The ¹H n.m.r. was consistant with the desired compound.

Preparation 7

Benzyl 9-N-[2-(N'-benzyl-N'-methylsulphonamido)ethyl]-N-(2'-methallyl)aminodeoxyclavulanate

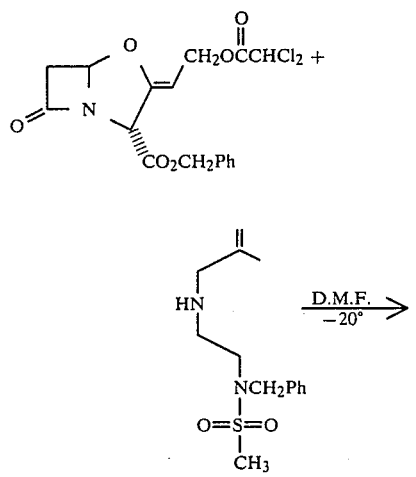

-continued

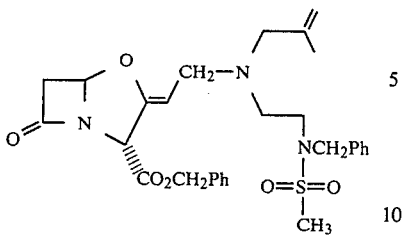

Benzyl dichloroacetyl clavulanate (3.159 g; 7.9 mmol) in dried dimethylformamide (22 ml) was cooled to −20°. A solution of 2-(N'benzyl-methylsulphonamido)ethyl-N-methylallylamine (4.24 g, 15 mmol) in dried dimethylformamide (15 ml) was added dropwise over a period of 30 minutes. After a further 30 minutes at −20° the reaction was warmed to room temperature. After 2 hours at ambient temperature the reaction was diluted with ethyl acetate and washed with brine (3×). The dried (MgSO$_4$) organic layer was evaporated to leave an orange oil which was chromatographed on silica gel (toluene/ethyl acetate 3:1 as eluent) to give the title ester as an oil, 0.16 g (3.65%).

I.R. (film) 1793, 1740, 1686, 1328 and 1150 cm$^{-1}$.

N.M.R. (CDCl$_3$) 1.69 (3H, s, C$\underline{H}_3$C:C), 2.45 (2H, m, C$\underline{H}_2$CH$_2$N), 2.87 (2H, s, NCH$_2$C:C), 2.89 (3H, s, SC$\underline{H}_3$), 3.35 (6$\overline{H}$, m, SNCH$_2$, 6—CH$_2$ and 9—CH$_2$), 4.43 (2H, s, NC$\underline{H}_2$Ph), 4.5 (1H, m, 8—CH), 4.89 (2H, s, C:C$\underline{H}_2$), 5.14 (1H, s, 3—CH), 5.26 (2H, s, OCH$_2$), 5.71 (1H, d, J 3 Hz, 5—CH) and 7.48 (10H, s, aromatics).

EXAMPLE 7

9-N-[N'-benzyl-N'-methylsulphonamido)ethyl-]aminodeoxyclavulanic acid

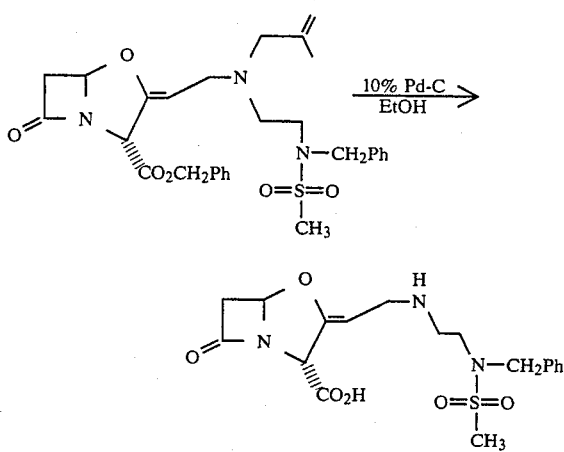

An ethanolic solution (10 ml) of benzyl-9-N-(2-[N'benzyl-methylsulphonamido]ethyl)-N-(methylallyl-)aminodeoxyclavulanate (0.15 g, 0.27 mmole), containing 10% Pd/C (0.1 g), was hydrogenated at normal temperature and pressure for 2 hours. The catalyst was filtered off and washed with ethanol; subsequent aqueous washings were collected and evaporated to leave a white solid which was recrystallised from acetone/diethylether to afford the title product, 0.037 g (33%).

I.R. (Nujol) 3400, 1783, 1685 and 1605 cm$^{-1}$.

N.M.R. (D$_2$O) 2.67 (2H, m, NH.C$\underline{H}_2$), 2.96 (3H, s, CH$_3$), 3.45 (6H, m, CH$_2$NS, 6—CH$_2$ and 9—CH$_2$), 4.5 (2H, s, C$\underline{H}_2$Ph), 4.52 (HOD obscuring 8—CH), 8.86 (1H, d, J 1.5 Hz, 3—CH), 5.64 (1H, d, J 3 Hz, 5—CH) and 7.4 (5H, s, aromatics).

Preparation 8

Benzyl 9-[N-(2-diethyloxyphosphorylethyl)-N-(2-methallyl)-]aminodeoxyclavulanate

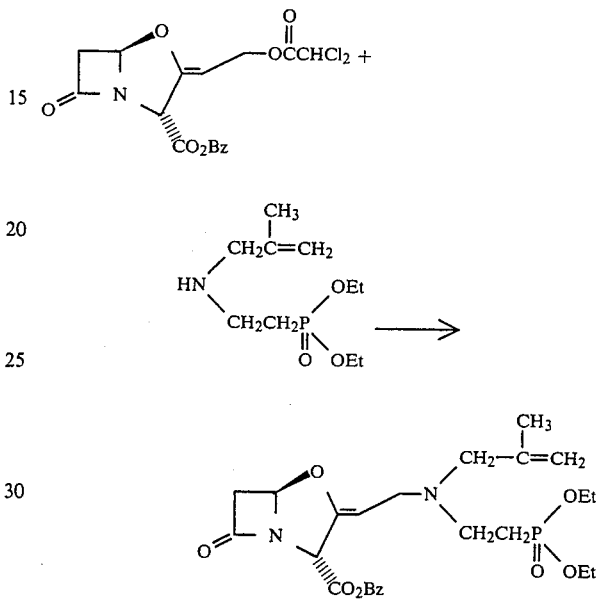

A solution of benzyl dichloroacetylclavulanate (8 g; 20 mmol) in dry dimethylformamide (80 ml), cooled to 0°, was treated dropwise (over 10 minutes) with a solution of N-(2-diethyloxyphosphorylethyl)-2-methallylamine (4.7 g; 20 mmol) in dry dimethylformamide (20 ml). The reaction mixture was warmed to room temperature and after 4 hours the solution was poured into ethyl acetate (200 ml), washed with water (2×100 ml), brine (100 ml), and dried over MgSO$_4$. The organic phase was evaporated to an oil and chromatographed on silica gel (toluene/ethyl acetate 4:1, as eluent) to give the title ester as a colourless oil in 30% yield.

$\nu_{max}$ (film) 1800, 1740, 1695 cm$^{-1}$.

δ(CDCl$_3$) 1.31(6H, t, J 7 Hz, CH$_2$C$\underline{H}_3$), 1.69(3H, s, C(C$\underline{H}_3$)=CH$_2$), $$1.93(2H, m, NCH_2C\underline{H}_2\overset{O}{\overset{\|}{P}}(OEt)_2), 2.66(2H, m, NC\underline{H}_2CH_2\overset{O}{\overset{\|}{P}}(OEt)_2),$$

2.86(2H, s, NC$\underline{H}_2$C(CH$_3$)=CH$_2$), 3.09(1H, d, J 17 Hz, 6β—C$\underline{H}$), 3.14(2H, m, 9—C$\underline{H}_2$), 3.47(1H, dd, J 17 and 3 Hz, 6α—C$\underline{H}$), 4.08(4H, m, C$\underline{H}_2$CH$_3$), 4.68(1H, dt, J 3 and 1.5 Hz, 8—C$\underline{H}$), 4.83(2H, bs, C(CH$_3$)=C$\underline{H}_2$), 5.08 (1H, s, 3—C$\underline{H}$), 5.17, 5.22(2H, ABq, J 12 Hz, C$\underline{H}_2$Ar), 5.67(1H, d, J 3 Hz, 5—C$\underline{H}$), 7.36(5H, s, Ar—$\underline{H}$).

EXAMPLE 8

9-N-(2-Diethyloxyphosphorylethyl)aminodeoxyclavulanic acid

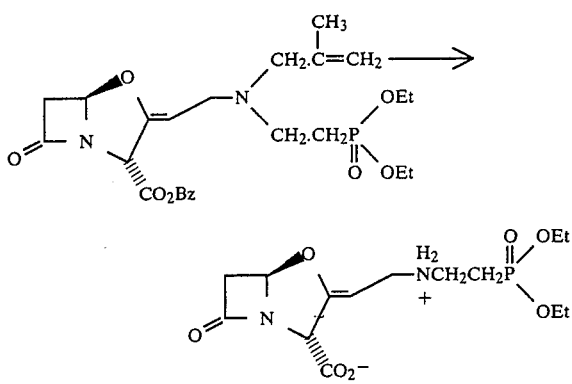

The tertiary amine (400 mg; 0.8 mmol) in aqueous tetrahydrofuran (25 ml; tetrahydrofuran:water, 10:1) was hydrogenated over 10% Pd/C (120 mg) for 1 hour. The catalyst was filtered off, cake washed with aqueous tetrahydrofuran, and the filtrate and washings combined and evaporated. The crude solid was crystallised from aqueous acetone to give the title compound in 30% yield.

$\nu_{max}$ (KBr) 1790, 1692, 1615 (b) cm$^{-1}$. $\delta$(D$_2$O), 1.34(6H, t, J 7 Hz, 2×CH$_2$CH$_3$), 2.34(2H, m, NCH$_2$CH$_2$P(OEt)$_2$), 3.17(1H, d,
                        ‖
                        O J 17 Hz, 6$\beta$—CH),3.27(2H, m, NCH$_2$CH$_2$P(OEt)$_2$),
                                          ‖
                                          O 3.6(1H, dd, J 17 and 3 Hz, 6 $\alpha$—CH), 3.77(2H, m, 9—CH$_2$), 4.17(4H, m, 2×CH$_2$CH$_3$), 4.82(1H, triplet obscured by HOD peak, 8—CH), 5.04(1H, s, 3—CH), 5.8(1H, d, J3 Hz, 5—CH).

Preparation 9

Lithium 9-N-[4-(lithium sulphonato)butyl]-N-benzylaminodeoxyclavulanate

9-N-Benzylaminodeoxyclavulanic acid (288 mg; 1 mmol) in aqueous dimethylformamide (50:50; 20 cm$^3$) was treated with lithium carbonate (37 mg) followed by 1 equivalent of 1,4-butanesultone (0.1 cm$^3$). The reaction mixture was stirred for several minutes then a further 0.2 cm$^3$ butanesultone was added followed by another 0.5 equivalents of lithium carbonate. After 24 hours and 48 hours a further 0.1 cm$^3$ 1,4-butanesultone was added. After a total of 72 hours reaction time the solvent was evaporated and the residue triturated with acetone to afford a solid. This solid was chromatographed on silica eluting with 5:4:2 ethyl acetate-ethanol-water. Fractions containing material Rf (SiO$_2$./ethyl acetate-ethanol-water; 5:4:2)=0.5 (detection by aqueous potassium permanganate spray) were combined and evaporated and triturated with ethanol to afford the title compound as an off-white solid, yield=31 mg, $\nu$ (Nujol) 1790, 1695, 1620, 1310, 1190, 1042, 740, 720, 702 cm$^{-1}$; $\nu$ (KBr) 1785, 1690, 1620, 1390, 1310, 1190, 1040, 740, 700 cm$^{-1}$; $\delta$ (D$_2$O) 1.60–1.97 (4H, m, NCH$_2$CH$_2$CH$_2$), 2.90 (2H, t, J 7 Hz, NCH$_2$(CH$_2$)$_3$), 3.10 (2H, bt, J 7.5 Hz, NCH$_2$(CH$_2$)$_2$CH$_2$SO$_3$), 3.12 (1H, d, J 17 Hz, 6$\beta$CH) 3.58 (1H, dd, J 17 and 3 Hz, 6$\alpha$CH), 3.78 and 3.85 (2H, d ABq, J 13 and 7.5 Hz, 9CH$_2$), 4.27 (2H, s, NCH$_2$C$_6$H$_5$), 4.85 (1H, t, J 7.5 Hz, 8CH), 5.05 (1H, s, 3CH), 5.78 (1H, d, J 3 Hz, 5$\alpha$CH), 7.41–7.60 (5H, m, C$_6$H$_5$).

EXAMPLE 9

Lithium 9-N-[4-(lithium sulphonato)butyl]aminodeoxyclavulanate

Lithium 9-N-[4-(lithium sulphonato)butyl]-N-benzylaminodeoxyclavulanate in aqueous tetrahydrofuran was hydrogenolysed at atmospheric pressure in the presence of 10% palladium on carbon ($\frac{1}{3}$ weight) until thin layer chromatography showed that debenzylation had gone to completion. The catalyst was filtered off and the filtrate evaporated to low volume. This solution was chromatographed on silica to afford the title compound.

Preparation 10a

N-(2-phenylthioethyl)methallyamine

N-Methallyamine (2.24 g; 31.5 mmol) and 2-chloroethylphenyl sulphide (2.7 g; 15.6 mmol) were heated together under reflux for 1 hr. Ether (100 ml) was then added, and the precipitate filtered off. The filtrate was evaporated in vacuo to give a yellow oil, which was subjected to silica-gel column chromatography eluting with ethyl acetate:cyclohexane (2:3). Fractions with Rf 0.7 (ethyl acetate:cyclohexane; 2:3) were combined and evaporated to give the title compound as a pale yellow oil (yield 51%). $\delta_H$ (CDCl$_3$) 1.47 (1H, s, NH), 1.68 (3H, broad s, CH$_2$C:CH$_2$(CH$_3$)), 2.88 (4H, m, CH$_2$CH$_2$SPh), 3.09 (2H, s, CH$_2$C:CH$_2$(CH$_3$)), 4.70–4.90 (2H, m, CH$_2$C:CH$_2$(CH$_3$)), 7.00–7.45 (5H, m, ArH). Addition of D$_2$O caused s at 1.47 to disappear.

Preparation 10b p-Nitrobenzyl 9-N-methallyl-N-(2-phenylthioethyl)aminodeoxyclavulanate

To a solution of p-nitrobenzyl dichloroacetylclavulanate (1 g, 2.2 mmol) in dimethylformamide (10 ml) at −10° C. was added dropwise over 10 min. a solution of N-(2-phenylthioethyl)methallylamine (1.1 g; 4.6 mmol) in dimethylformamide (5 ml). The reaction mixture was stirred at −10° C. for 0.5 hr. then allowed to warm to room temperature. After stirring for a further 4 hr. the solution was poured into ethylacetate (50 ml) and the organic phase washed with water (3×50 ml), saturated brine (2×50 ml) then dried over anhydrous magnesium sulphate. Removal of the solvent in vacuo produced a yellow oil, which after silica-gel column chromatography, eluting with ethyl acetate:cyclohexane (2:3) gave the title compound (Rf=0.6; ethyl acetate:cyclohexane; 2:3) as a pale yellow oil (yield 9%).

$\nu_{max}$ (CHCl$_3$) 1800, 1750 and 1700 cm$^{-1}$.

$\delta$H (CDCl$_3$) 1.68 (3H, s, C:CH$_2$(CH$_3$)), 2.50–2.80 (2H, m, CH$_2$CH$_2$SPh), 2.82–3.30 (7H, m, 6$\beta$—CH, CH$_2$CH$_2$SPh, 9—CH$_2$, CH$_2$C:CH$_2$(CH$_3$)), 3.45 (1H, dd, J 17 and 3 Hz, 6$\alpha$—CH) 4.69 (1H, t, J 7 Hz, 8—CH, partly obscured by s at $\delta$ 4.79) 4.79 (2H, broad s, CH$_2$C:CH$_2$(CH$_3$)), 5.08 (1H, s, 3—CH), 5.23 (2H, s, CH$_2$Ar), 5.62 (1H, d, J 3 Hz, 5—CH), 7.10–7.35 (5H, m, ArH), 7.47 and 8.20 (4H, ABq, J 9 Hz, ArH).

EXAMPLE 10

9-N-(2-phenylthioethyl)aminodeoxyclavulanate p-Nitrobenzyl 9-N-methallyl-N-(2-phenylthioethyl)aminodeoxyclavulanate (0.41 g; 0.78 mmol) in ethanol:-tetrahydrofuran; 1:1 (5 ml) was added to a suspension of 10% palladium on charcoal (0.14 g) in ethanol:tetrahydrofuran; 1:1 (10 ml) which had been prehydrogenated at room temperature for 1 hr after which a further quantity of 10% palladium on charcoal (0.1 g) was added and hydrogenolysis continued for 1¾ hr. The catalyst was filtered off, and washed with ethanol:tetrahydrofuran (1:1). The filtrate was evaporated in vacuo to give a brown oil, which after column chromatography using ethyl acetate:ethanol:water (8:2:1) as eluent produced the title compound.

Preparation 11

Benzyl 9N-[2(N,N-dimethylsulphamoyl)benzylaminoethyl]-N-methallyl-aminodeoxyclavulanate Benzyl dichloracetylclavulanate (3.55 g, 8.875 mmol) in dimethylformamide (20 ml) at $-20°$ C. was treated dropwise with 2[(N,N-dimethylsulphamoyl)benzylamino]ethylmethallylamine (5.52 g, 17.75 mmol) in dimethylformamide (20 ml). The reaction was then allowed to warm to ambient temperature and after 8 hr the reaction was diluted with ethyl acetate and washed with brine (3×). The organic layer was dried (MgSO$_4$) and evaporated to a syrup which was chromatographed upon silica gel (toluene/ethyl acetate 2:1 as eluent). The title ester was thus obtained as an oil, 1.2 g (15.3% yield).

$\nu_{max}$. 1805, 1751 and 1694 cm$^{-1}$. N.M.R. $\delta$ (CDCl$_3$) 1.66 (3H, br s, C:C.CH$_3$), 2.3–3.69 (10H, m, N.CH$_2$.CH$_2$.N, 2×C:C.CH$_2$ and 6—CH$_2$), 2.82 (6H, s, N(CH$_3$)$_2$, 4.4 (2H, s, N.CH$_2$Ph), 4.69 (1H, m, obscured 8—CH), 4.86 (2H, br s, C:CH$_2$), 5.11 (1H, m, 3—CH), 5.27 (2H, s, CO$_2$CH$_2$), 5.68 1H, d, J 2 Hz, 5—CH) and 7.47 (10H, s, ArH).

EXAMPLE 11

9N-[2(N,N-dimethylsulphamoyl)benzylamino]ethylaminodeoxyclavulanic acid

Benzyl-9N-[2(N,N-dimethylsulphamoyl)benzylaminoethyl]-N-methallyl-aminodeoxyclavulanate (0.769 g, 1.35 mmol) in ethanol, (5 ml) was added to prehydrogenated catalyst, Pd/C (10%, 0.3 g) in ethanol/water (10 ml, 9:1). This mixture was then hydrogenated for 25 min. when reaction was complete. The mixture was filtered and the catalyst washed with water. The aqueous washings were filtered and evaporated to afford the title acid as a white solid, 0.05 g (8.65% yield.).

$\nu_{max}$ (Nujol) 3560, 3360, 1798, 1698 cm$^{-1}$ $\delta$ (DMSO-d$^6$) 2.70(6H, s, N(CH$_3$)$_2$), 2.7–3.7 (8H, m, C=CCH$_2$NCH$_2$CH$_2$N and 6—CH$_2$), 4.33(2H, s, NCH$_2$Ph), 4.5–4.76(2H, m, 3—CH and 8—CH), 5.56(1H, bs, 5—CH), 7.33(5H, s, ArH).

Preparation 12a

1-Methanesulphonamido 2-methanesulphonyloxyethane

A stirred solution of ethanolamine (9.15 g) in pyridine (40 ml) was cooled to 0° C. in an ice-salt bath, and mesylchloride (23 ml) was added dropwise at such a rate that the temperature did not rise above 5° C. When the addition was complete the mixture was allowed to rise to room temperature for ½ hour. The mixture was poured into citric acid solution and continuously extracted with ehtylacetate for 1½ hours. The solution was dried over magnesium sulphate and evaporated to give 23.7 g of the title compound.

IR $\nu_{max}$ (film) 3290, 1350, 1325, 1180 and 1150 cm$^{-1}$.

NMR (CDCl$_3$) 3.02 (3H, s), 3.18 (3H, s), 3.48 (2H, apparent q, J=6 Hz), 4.40 (2H, t, J=6 Hz), 7.23 (1H, broad t, J=6 Hz).

Preparation 12b

1-Benzylamino 2-methanesulphonamidoethane

1-Methanesulphonamido 2-methanesulphonyloxyethane (23.3 g) was added in small portions to benzylamine (24 ml) at such a rate that the temperature did not rise above 30° C. When the addition was complete the mixture was stirred at room temperature for one hour. Ethylacetate (150 ml) was then added to the mixture and the precipitated solid was filtered off. The filtrate was evaporated and the product isolated by column chromatography of the residue using gradient elution (Kieselgel, ethylacetate going to 30% methanol in ethylacetate as eluent). The product was recrystallised from ethylacetate-petroleum ether to give 10.9 g of pale yellow crystals, mpt 71°–73° C.

IR $\nu_{max}$ (Nujol) 1310 and 1155 cm$^{-1}$.

NMR $\delta$ (CDCl$_3$) 2.65–3.00 (2H, m), 2.87 (3H, s), 3.10–3.32 (2H, m) 3.58 (2H, broad s), 3.80 (2H, s), 7.34 (5H, s).

Preparation 12c

Benzyl 9-[N-benzyl N-(2-methylsulphonamido)ethyl]aminodeoxyclavulanate

A solution of 1-benzylamino 2-methanesulphonamidoethane (4.6 g) in dimethylformamide (15 ml) was added dropwise to a solution of benzyl 9-O-dichloroacetylclavulanate (4.0 g) in dimethylformamide (25 ml) cooled to $-12°$ C. The rate of addition was such that the temperature of the solution did not rise above $-10°$ C. When the addition was complete the temperature was allowed to rise to $-5°$ C. over 45 minutes. The solution was diluted with toluene (100 ml) and washed with 6 portions of water (50 ml). The solution was washed with brine, dried over magnesium sulphate and evaporated to about 20 ml of solution. The product was obtained by column chromatography of the residual solution using gradient elution (Kieselgel, 1:1 60/80 petroleum ether:ethylacetate going to ethyl acetate as eluent). Thus was obtained 1.99 g of a pale yellow gum.

IR $\nu_{max}$ (CHCl$_3$), 1805, 1750, 1695, 1325, and 1155 cm$^{-1}$.

NMR $\delta$ (CDCl$_3$) 2.52 (2H, t, J=6 Hz), 2.70 (3H, s), 2.9–3.25 (5H, m), 3.43 (2H, s), 3.45 (1H, dd, J=3 and 17 Hz), 4.70 (1H, broad t, J=7 Hz), 5.08 (1H, s), 5.18 (2H, s), 5.64 (1H, d, J=3 Hz), 7.23 (5H, s), 7.31 (5H, s).

EXAMPLE 12

9-N-(2-methylsulphonamidoethyl)aminodeoxyclavulanic acid

A solution of benzyl 9-[N-benzyl N-(2-methylsulphonamido)ethyl]aminodeoxyclavulanate (1.84 gm) in ethanol (35 ml) and tetrahydrofuran (15 ml) was hydrogenated over 10% palladium on carbon (0.6 gm) for 1 hr. Water (10 ml) and fresh catalyst (0.5 gm) were added and the mixture was hydogenated for a further 30 minutes. The solution was filtered through celite and the organic solvents were removed on a rotary evaporator. The aqueous solution was filtered through celite and freeze-dried to give 0.89 gm of a light brown foam.

I.R. $\nu_{max.}$ (KBr) 1789, 1695, 1620, 1310 and 1145 cm$^{-1}$. N.M.R. $\delta$ (D$_2$O) 3.02 (3H, s), 2.9–3.5 (5H, m), 3.51 (1H, dd, J=3 and 17 Hz) 3.70 (2H, d, J=7 Hz), 4.73 (1H, broad t, J=7 Hz), 4.92 (1H, s), 5.69 (1H, d, J=3 Hz).

Preparation 13a

1-Methanesulphonamido 3-methanesulphonyloxypropane

This compound was prepared by the method described in preparation 12a.

IR $\nu_{max}$ (film) 3280, 1350, 1320, 1175, 1155 cm$^{-1}$.

NMR $\delta$ (CDCl$_3$) 2.12 (2H, quintet, J=6 Hz), 3.04 (3H, s), 3.12 (3H, s), 3.35 (2H, q, J=6 Hz), 4.45 (2H, t, J=6 Hz), 5.29 (1H, broad t, J=6 Hz).

Preparation 13b

1-Benzylamino 3-methanesulphonamidopropane

This compound was prepared by the method described in preparation 12b.

IR $\nu_{max}$ (Nujol) 1315, and 1150 cm$^{-1}$.

NMR $\delta$ (CDCl$_3$) 1.75 (2H, quintet, J=6 Hz), 2.80 (2H, t, J=6 Hz), 2.87 (3H,s), 3.24 (2H, t, J=6 Hz), 3.79 (2H, s), 3.6–4.2 (2H, broad), 7.32 (5H, s).

Preparation 13c

Benzyl 9-[N-benzyl N-(3-methylsulphonamido)propyl]aminodeoxyclavulanate

A solution of 1-benzylamino 3-methylsulphonamidopropane (4.84 g) in dimethylformamdie (15 ml) was added dropwise to a solution of benzyl 9-O-dichloroacetylclavulanate (4.0 g) in dimethylformamide (25 ml) cooled to −12° C. The rate of addition was such that the temperature did not rise above −10° C. When the addition was complete the solution was stirred at −10° C. for 30 minutes. Toluene (100 ml) was added to the solution, and the toluene solution was washed with 5 portions of water (50 ml). The solution was then washed with brine, dried over magnesium sulphate and evaporated to about 20 ml. The product was obtained by column chromatography of the residual solution using gradient solution (Kieselgel, 1:1 60/80 petroleum ether:ethylacetate going to ethylacetate as eluent). Thus was obtained 3.25 g of a pale yellow gum.

IR $\nu_{max}$ (CHCl$_3$) 1805, 1750, 1695, 1325, and 1150 cm$^{-1}$.

NMR $\delta$ (CDCl$_3$) 1.66 (2H, quintet, J=6 Hz), 2.44 (2H, t, J=6 Hz), 2.76 (3H, s) 2.98 (1H, d, J=17 Hz), 3.03 (2H, t, J=6 Hz), 3.15 (2H, d, J=7 Hz), 4.70 (1H, broad t, J=7 Hz), 5.07 (1H, s), 5.17 (2H, s), 5.65 (1H, d, J=3 Hz), 7.24 (5H, s), 7.31 (5H, s).

Preparation 14a 1-(N-methyl)methanesulphonamido 2-methanesulphonyloxyethane

This compound was prepared by the method described in preparation 12a.

IR $\nu_{max}$ (film) 1350, 1330, 1175, 1150 cm$^{-1}$.

NMR $\delta$ (CDCl$_3$) 2.98 (3H, s), 3.07 (3H, s), 3.18 (3H, s), 3.65 (2H, t, J=6 Hz), 4.49 (2H, t, J=6 Hz).

EXAMPLE 13

9-N-(3-Methylsulphonamidopropyl)aminodeoxyclavulanic acid

A solution of benzyl 9-[N-benzyl-N-(3-methyl sulphonamido)propyl]aminodeoxy clavulanic acid (3.16 gm.) in a mixture of tetrahydrofuran (30 ml.) ethanol (40 ml.) and water (30 ml.) was hydrogenated over 10% palladium on carbon (1 gm.) for 1½ hours. The solution was filtered through celite and the filter cake washed with water. The combined filtrates were evaporated and the product isolated by column chromatography using gradient elution (Kieselgel; 5:3:2 grading to 3:4:3 ethyl acetate:isopropanol:water). Fractions containing the major product were evaporated to about 2 ml. and triturated with ethanol. The crystalline product was filtered off, washed with ethanol and dried under vacuum to give 0.706 gm. of product.

I.R. $\nu_{max}$ (KBr) 1797, 1687, 1610 cm$^{-1}$.

N.M.R. $\delta$ (D$_2$O) 1.86(2H, quintet, J 8 Hz) 3.00(3H,s), 2.95–3.25(5H,m), 3.54(1H,dd,J 3 and 17 Hz), 3.69(2H,d,J 7 Hz), 4.77 (1H, broad t, J 7 Hz), 5.74(1H,d,J 3 Hz).

Preparation 14b

1-Benzylamino 2-(N-methyl)methanesulphonamidoethane 1-(N-methyl)methanesulphonamido 2-methanesulphonyloxyethane (22.5 g) was added, in small portions, to a stirred mixture of benzylamine (22 ml) and triethylamine (14 ml) at such a rate that the temperature did not rise above 30° C. When the addition was complete the mixture was heated at 40° for 2 hours. The mixture was then dissolved in ethylacetate and the solution washed twice with water, then with brine, and dried over magnesium sulphate. The solution was evaporated and the product isolated by column chromatography of the residue using gradient elutim (Kieselgel, ethylacetate going to 30% methanol in ethyl acetate as eluent), to give 15.67 g of product as a pale yellow oil.

IR $\nu_{max}$ (film) 1335 and 1145 cm$^{-1}$.

NMR $\delta$ (CDCl$_3$) 2.81 (3H, s), 2.82 (2H, t, J=6 Hz), 2.84 (3H, s), 3.30 (2H, t, J=6 Hz), 3.82 (2H, s), 7.33 (5H, s).

Preparation 14c

Benzyl 9-{N-benzyl N-[2-(N-methyl)methylsulphonamido]ethyl}aminodeoxyclavulanate A solution of 1-benzylamino 2-(N-methyl)methanesulphonamidoethane (4.84 g) in dimethylformamide (15 ml) was added dropwise to a solution of benzyl 9-O-dichloroacetylclavulanate (4.0 g) in dimethylformamide (25 ml) cooled to −12° C. The rate of addition was such that the temperature of the solution did not rise above −10° C. When the addition was complete the mixture was stirred at −5° C. for 30 minutes. The mixture was dissolved in toluene (100 ml) and the resulting solution was washed with 5 portions of water (50 ml), then with brine, and finally dried over magnesium sulphate. The solution was evaporated to about 20 ml and the product was isolated by column chromatography of the residual solution using gradient elution (Kieselgel, 1:1 60/80 petroleum ether: ethyl acetate going to ethylacetate as eluent). Thus was obtained 1.23 g of pale yellow gum.

IR $\nu_{max}$ (CHCl$_3$) 1805, 1750, 1695, 1330 and 1150 cm$^{-1}$.

NMR δ(CDCl$_3$) 2.53 (2H, t, J=6 Hz), 2.69 (3H, s), 3.72 (3H, s), 3.00 (1H, d, J=17 Hz), 3.19 (2H, t, J=6 Hz), 3.23 (2H, d, J=7 Hz), 3.45 (1H, dd, J=3 and 17 Hz), 3.49 (2H, s), 4.71 (1H, broad t, J=7 Hz), 5.07 (1H, s), 5.17 (2H, s), 5.64 (1H, d, J=3 Hz), 7.23 (5H, s), 7.31 (5H, s).

EXAMPLE 14

9-N-[2-(N-methyl)methylsulphonamidoethyl-]aminodeoxyclavulanic acid

A solution of benzyl 9-N-{N-benzyl-[2-(N-methyl)-methylsulphonamido]ethyl}aminodeoxyclavulanate (1.23 gm) in a mixture of ethanol (30 ml) tetrahydrofuran (10 ml) and water (10 ml) was hydrogenated over 10% palladium on carbon (0.4 gm) for 1 hr. The solution was filtered through celite and the filter cake washed with water. The organic solvents were removed from the combined filtrates on a rotary evaporator and the aqueous solution was washed twice with ethyl acetate. The aqueous solution was filtered through celite and evaporated to about 1 ml. The residual solution was triturated with ethanol and the crystalline solid filtered off, washed with ethanol and dried under vacuum to give 0.36 gm of white solid.

N.M.R. δ (D$_2$O) 2.89 (3H, s), 3.01 (3H, s), 3.15 (1H, d, J=17 Hz) 3.15–3.6 (4H, m), 3.63 (1H, dd, J=3 and 17 Hz), 3.83 (2H, d, J=7 Hz) 4.84 (1H, broad t, J=7 Hz), 5.05 (1H, s), 5.80 (1H, d, J 7=3 Hz).

Preparation 15a

N-(2-Hydroxyethyl)-N-(2-methallyl)amine

2-Methallylchloride (22.5 g; 250 mmol) was treated with 2 equivalents of ethanolamine and heated at 90° for 3 hours. The reaction mixture was poured into diethyl ether and the solid ethanolamine hydrochloride filtered off. The filtrate was evaporated to afford an oil. This crude oil was distilled at reduced pressure (water pump) and a distillate collected, bp 95°–100°. This oil was chromatographed on silica, eluting with ethylacetate grading to ethylacetate-ethanol-water 5:3:2. Fractions were collected containing a polar material, and combined fractions were evaporated to an oil. Yield=8.9 g (30%) ν(film) 3300 (broad), 1450, 1120, 1055, 895 cm$^{-1}$ δ (CDCl$_3$) 1.74(3H, s, CH$_3$), 2.70(2H, t, J5 Hz, CH$_2$CH$_2$N), 3.17(2H, s, NCH$_2$C(CH$_3$)), 3.28(2H, s, OH and NH), 3.64(2H, t, J5 Hz, CH$_2$CH$_2$O), 4.85(2H, broad, s, C(CH$_3$)=CH$_2$).

Preparation 15b

Benzyl 9-N-(2-hydroxyethyl)-N-(2-methallyl)-aminodeoxyclavulanate

Benzyl dichloroacetylclavulanate (15.6 g; 39 mmol) in dimethylformamide (100 cm$^3$) at −30° was treated 1.9 equivalents of N-(2-hydroxyethyl)-N-(2-methallyl)amine, dropwise, in dimethylformamide (20 cm$^3$) over 10 minutes. The reaction was stirred for one hour between −20° and 0°. The mixture was poured into ethylacetate (300 cm$^3$) and washed with water (4×150 cm$^3$) and saturated brine (5×200 cm$^3$), dried (anhydrous magnesium sulphate) and evaporated to an oil. This oil was chromatographed on silica, eluting with ethylacetate-cyclohexane; 1:1 grading to neat ethylacetate. Fractions were collected containing a material Rf (SiO$_2$/ethlacetate)=0.4 (detection by aqueous potassium permanganate spray). Combined fractions were evaporated to afford an oil, yield=1 g; ν(film) 1810, 1750, 1695, 900, 745, 700 cm$^{-1}$.

Preparation 15c

Benzyl 9-N-[2-[6β-(DL-2-phenoxycarbonyl-2-thien-3'-ylacetamido)penicillanoyloxy]ethyl]-N-(2-methallyl-)aminodeoxyclavulanate To 6β(DL-2-Phenoxycarbonyl-2-thien-3'-ylacetamido)penicillanic acid (1.19 g; 2.59 mmol) in methylene dichloride (20 cm$^3$) at 0° was added benzyl 9-N-(2-hydroxyethyl)-N-(2-methallyl)aminodeoxyclavulanate (1 equivalent). To this was added 1 equivalent of dicyclohexylcarbodiimide (DCCI) and stirred for 1½ hours at 0°. The reaction mixture was filtered and the filtrate washed with saturated brine, dried (anhydrous magnesium sulphate) and evaporated to an oil. This oil was chromatographed on silica eluting with ethyl acetate-cyclohexane; 1:2. Fractions were collected containing the title compound, Rf (SiO$_2$/ethyl acetate-cyclohexane; 1:1)=0.6 (detection by aqueous potassium permanganate spray). Combined fractions were evaporated to afford 460 mg (22%) of a foam.

ν(film) 3330, 1790, 1750, 1690, 1515, 1490, 1303, 1190, 1160, 1130, 1010, 895 cm$^{-1}$, 250 MHz $^1$Hnmr.

δ (CDCl$_3$) 1.40–1.60 (6H, m, gem diCH$_3$), 1.68 (3H, s, C(CH$_3$)=CH$_2$), 2.57 (2H, broad t, J5 Hz, CH$_2$CH$_2$N), 2.88 (2H, s, NCH$_2$C(CH$_3$)), 3.04 (1H, d, J17 Hz, 6βCH), 3.18 (2H, d, J 7 Hz, 9CH$_2$), 3.47 (1H, dd, J17 and 3 Hz, 6 CH), 4.16 (2H, broad t, J5 Hz, CH$_2$CH$_2$O), 4.39 and 4.41 (1H, 2xs, 3CH of penicillanate), 4.65 (1H, broad t, J7 Hz, 8CH), 4.83 (2H, broad s, C(CH$_3$)=CH$_2$), 4.95 and 4.98 (1H, 2xs, CHCONH), 5.08 (1H, d, J≈1 Hz, 3CH of clavulanate), 5.16 and 5.22 (2H, ABq, J12 Hz, OCH$_2$C$_6$H$_5$), 5.50–5.57 (1H, m, 5αCH of pencillanate), 5.66 (1H, d, J3 Hz, 5αCH of clavulanate), 5.63–5.73 (1H, m, 6αCH of penicillanate), 7.05–7.57 (9H, broad m, NH, C$_6$H$_5$ and thienyl aromatics), 7.36 (5H, s, CH$_2$C$_6$H$_5$).

EXAMPLE 15

9-N-[2-[6β-(DL-2-Phenoxycarbonyl-2-thien-3'-ylacetamido)penicillanoyloxy]ethyl]aminodeoxyclavulanic acid Benzyl 9-N-[2-[6β-(DL-2-phenoxycarbonyl-2-thien-3'-yl-acetamido)penicillanoyloxy]ethyl]-N-(2-methallyl)amino deoxyclavulanate (425 mg, 0.5 mmol) in tetrahydrofuranethanol (1:1, 10 cm$^3$) was hydrogenolysed at atmospheric pressure in the presence of prehydrogenated 10% palladium on carbon (200 mg) for 2½ hours, when a further 200 mg of palladium on carbon was added and hydrogenolysed for a further 20 hours. The catalyst was filtered off and the filtrate evaporated to an oil. This oil was chromatographed on silica eluting with ethyl acetate-ethanol-water 6:2:1 and fractions Rf(SiO$_2$-/ethyl acetate-ethanol-water 6:2:1)=ca. 0.5 (detection by aqueous potassium permanganate spray) were collected, and combined fractions evaporated to afford a solid from acetonitrile, yield=30 mg (9%) ν(Nujol) 1785, shoulder at 1750, 1687, 1620 cm$^{-1}$.

δ (DMSO-D$_6$/D$_2$O) 1.30–1.60 (6H, m, gem diCH$_3$), 2.96 (1H, d, J16 Hz, 6βCH), 3.17 (2H, bm NH$_2$CH$_2$CH$_2$), 3.48 (1H, dd, J16 and 3 Hz, 6αCH), 3.58 (2H, d, J7 Hz, 9CH$_2$), 4.12–4.28 and 4.30–4.47 (2H, 2×bm, NCH$_2$CH$_2$O), 4.50–4.51 (1H, 2xs, 3CH of penicillanate thiazolidine ring), 4.63 (1H, s, 3CH of clavulanate oxazolidine ring), 4.67 (1H, t, J7 Hz, 8CH),
5.39–5.58 (2H, m, 5CH and 6CH of penicillante β lactam), 5.66 (1H, d, J3 Hz, 5CH of clavulanate β lactam),
7.00–7.54 (8H, m, phenyl and thienyl aromatic protons).

Preparation 16a p-Nitrobenzyl
9-N-(2-hydroxyethyl)-N-(2-methallyl)amino deoxyclavulanate (4-Nitrobenzyl)9-O-dichloroacetylclavulanate (18.3 g, 41 mmol) in dimethylformamide (100 cm³) at −20°, was treated with 1.9 equivalents of N-(2-hydroxyethyl)-N-(2-methallyl)amine dropwise in dimethylformamide. The mixture was stirred for 1¾ hours between −20° and +5°. The reaction mixture was poured into ethyl acetate (300 cm³) and washed with water (5 × 100 cm³) and saturated brine (5 × 100 cm³), dried (anhydrous magnesium sulphate) and evaporated to a crude oil (20 g). R$_f$ of desired product (SiO/Ethyl acetate)=<0.2.

Preparation 16b p-Nitrobenzyl
9-N-[2-[6β-(DL-2-phenoxycarbonyl-2-thien-3'-ylacetamido)penicillanoyloxy]ethyl]-N-(2-methallyl-)aminodeoxyclavulanate (4-Nitrobenzyl) 9-N-(2-hydroxyethyl)-N-(2-methallyl)aminodeoxyclavulanate (5 g of crude material) plus 1 equivalent of 6β-(DL-2-phenoxycarbonyl-2-thien-3'-ylacetamido)penicillanic acid in methylene dichloride (50 cm³) was cooled to 0° and then treated with 1 equivalent of dicyclohexylcarbodiimide in methylene dichloride dropwise. The mixture was stirred for 1½ hours allowing the temperature to rise from 0° to 10°. The reaction mixture was washed with water (3 × 50 cm³) and saturated brine (5 × 50 cm⁻³), dried (anhydrous magnesium sulphate) and evaporated to a foam. This crude product was chromatographed on silica eluting with ethyl acetate-cyclohexane; 2:3. Fractions containing material R$_f$ (SiO₂/ethyl acetate-cyclohexane; 2:3)=0.38 were collected and combined fractions evaporated to afford an oil. This oil was dissolved in ethyl acetate (5 cm³) and filtered to remove some insoluble material. The filtrate was evaporated to afford the title compound as a foam, yield=0.79 g (20% overall from (4-nitrobenzyl)-9-O-dichloroacetylclavulanate).

ν(film) 3330, 1790, 1750, 1690, 1520, 1345, 1303, 1185, 1160, 1127, 1010 cm⁻¹. δ (CDCl₃) 250 MHz FT ¹Hnmr 1.40–1.60 (6H, m gem di CH₃), 1.68 (3H, s, C(CH₃)=CH₃), 2.61 (2H, t, J 5.5 Hz, NCH₂CH₂), 2.90 (2H, s, NCH₂C(CH₃)), 3.07 (1H, d, J 17 Hz, 6βCH), 3.15 and 3.22 (2H, D, ABq, 14 and 7 Hz, 9CH₂), 3.50 (1H, dd, J17 and 3 Hz, 6αCH of clavulanate β-lactam), 4.13–4.26 (2H, m, NCH₂CH₂O), 4.39 and 4.42 (1H, 2xs, 3CH of penicillin thiazolidine ring), 4.78 (1H, broad t, J7 Hz, 8CH), 4.84 (2H, s, C(CH₃)=CH₂), 4.86 and 4.88 (1H, 2xs, CHCONH), 5.12 (1H, broad s, 3CH of clavulanate oxazolidine ring), 5.26 and 5.32 (2H, ABq, J12.5 Hz, CO₂CH₂C₆H₄NO₂), 5.51–5.57 (1H, m, 5αCH of penicillin β-lactam), 5.62–5.73 (1H, m, 6αCH of penicillin β-lactam), 5.68 (1H, d, J3 Hz, 5αCH of clavulanate β-lactam), 7.03–7.65 (11H, m, thienyl and phenylaromatics CONH, -continued

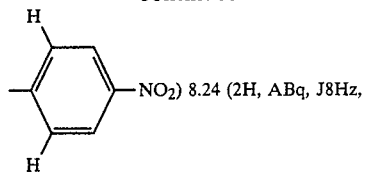 NO₂) 8.24 (2H, ABq, J8Hz,

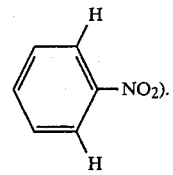 NO₂).

EXAMPLE 16

9-N-[2-[6β-(DL-2-Phenoxycarbonyl-2-thien-3-ylacetamido)penicillanoyloxy]ethyl]aminodeoxyclavulanic acid (4-Nitrobenzyl)9-N-[2-(6β-(DL-2-phenoxycarbonyl-2-thien-3'-ylacetamido)penicillanoyloxy]ethyl]-N-(2-methallyl)aminodeoxyclavulanate (1.5 g) in tetrahydrofuran-ethanol (1:1; 25 cm³) at atmospheric pressure was hydrogenolysed in the presence of 10% palladium on carbon (1.5 g; which had been prehydrogenated for 20 hours. The catalyst was filtered off and the filtrate evaporated. The crude product was chromatographed on silica eluting with ethyl acetate-ethanol-water (6:2:1) and fractions collected R$_f$(SiO₂/ethyl acetate/ethanol/-water; (6:2:1)=0.4 (detection by aqueous potassium permanganate spray). Combined fractions were evaporated to a foam, yield=150 mg (13%) ν(nujol) 3330, 1785, 1750, 1695, 1615, 1590, 1305, 1187, 1160, 1125 cm⁻¹; ν(KBr) 1780, 1750 (shoulder), 1685, 1620 cm⁻¹. The ¹H nuclear magnetic resonance spectra was consistant with the desired compound.

EXAMPLE 17

(a)

9-N-[2-[6β-(DL-2-Phenoxycarbonyl-2-thien-3'-ylacetamido)penicillanoyloxy]ethyl]-N-(2-methallyl-)aminodeoxyclavulanic acid

[4-Nitrobenzyl]9-N-[2-[6β-(DL-2-phenoxycarbonyl-2-thien-3'-ylacetamido)penicillanoyloxy]ethyl]-N-(2-methallyl)aminodeoxyclavulanate (0.63 g) in tetrahydrofuran-ethanol (1:1, 20 cm³) was hydrogenolysed at atmospheric pressure in the presence of 10% palladium on carbon (0.61 g, prehydrogenated) for 1½ hours. The catalyst was filtered off and the filtrate evaporated to an oil which was chromatographed on silica eluting with ethyl acetate-ethanol-water (6:2:1). Fractions were collected containing the required compound R$_f$ (SiO₂-/ethyl acetate-ethanol-water (6:2:1)=0.6 (detection by aqueous potassium permanganate spray). Combined fractions were evaporated to a foam, yield=100 mg (19%) ν(nujol) 3325, 1785, 1725, 1615, 1305, 1190, 1163, 1125, 895 cm⁻¹; 250 MHz nmr (D₆-DMSO//D₂O) 1.30–1.56 (6H, m, gem di CH₃), 1.62 (3H, s, C(CH₃)=CH₂), 2.68 (2H, broad s, NCH₂C(CH₃)), 2.82 (1H, d, J17 Hz, 6βCH), 2.99 (2H, broad s, NCH₂CH₂), 3.05–3.28 (2H, broad m, 9CH₂), 3.43 (1H, dd, J 17 and 3 Hz, 6αCH), NCH₂CH₂O obscured by HOD, 4.34 and 4.35 (1H, 2xs, 3CH of penicillanate thiazolidine ring), CHCONH exchanged by HOD, 4.58 (1H, s, 3CH of clavulanate oxazolidine ring), 4.61 (1H, t, J 7 Hz, 8CH), 4.81–4.91 (2H, m, C(CH₃)=CH₂), 5.36–5.62 (2H, m, 5CH and 6CH of penicillanate β-lactam), 5.57 (1H, d, J3 Hz, 5αCH of clavulanate β-lactam), 7.00–7.50 (8H, m, thienyl and phenyl aromatics).

(b)

This product is convered to 9-N-[2-[6β-(DL-2-phenoxycarbonyl-2-thien-3′-ylacetamido)penicillanoyloxy]ethyl]aminodeoxyclavulanic acid by further hydrogenation.

Preparation 18a

Benzyl 9-N-[3-(imidazol-1-yl)propyl]-N-2-methallylaminoclavulanate

Benzyl dichloroacetylclavulanate (6.35 g; 15.9 mmol) in dimethylformamide (50 cm³) at −20° was treated dropwise with 1.9 equivalents of N-[3-imidazol-1-yl)-propyl]-N-methallylamine in dimethylformamide (20 cm³). The reaction was stirred from −20° to 0° over 1 hour 20 minutes when it was poured into ethylacetate (300 cm³) and washed with water (3×100 cm³), saturated brine (5×100 cm³), dried (anhydrous magnesium sulphate) and evaporated to an oil. This oil was chromatographed on silica eluting with methyl-acetate. Fractions were collected containing the title compound; Rf (SiO₂/methylacetate)=0.5 (detection by aqueous potassium permanganate spray). Combined fractions were evaporated to afford 1.55 g (22%) of an oil. (film) 1800, 1747, 1690, 1500, 1448, 1300, 1225, 1180, 1010, 900, 890 cm⁻¹. δ (CDCl₃) 1.69 (3H, s, C(CH₃)=CH₂), 1.82 (2H, tt, J 7 and 7 Hz, NCH₂CH₂CH₂N),

2.45 (2H, t, J 7 Hz, NCH₂CH₂), 2.78 (2H, s, NCH₂C(CH₃)), 2.95 (1H, d, J 17 Hz, 6βCH), 3.08 (2H, d, J 7 Hz, 9CH₂), 3.43 (1H, dd, J 17 and 2.5 Hz, 6αCH),

3.90 (2H, t, J 7 Hz, CH₂CH₂N  N), 4.61 (1H, bt, J 7 Hz, 9CH), 4.80 (2H, bs, NCH₂C(CH₃)=CH₂) 5.03 (1H, bs, 3CH), 5.15 (2H, bs, CH₂C₆H₅), 5.60 (1H, d, J 2.5 Hz, 5αCH),

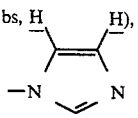

6.83 and 7.01 (2H, 2 × bs, H    H), 7.31 (5H, s, C₆H₅),
          −N    N

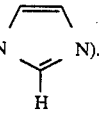

7.40 (1H, s, —N    N).
              H

Preparation 18b

N-[3-(Imidazol-1-yl)propyl]-N-2-methallylamine

N(3-Aminopropyl)imidazole (25 g; 0.2 mol) was heated with 2-methallylchloride (0.1 mol) for 1 hour under reflux. When cool the resulting oil was shaken with ether, an immiscible oil separated out. The ethereal phase was decanted and evaporated to low volume when it was chromatographed on silica eluting with ethyl acetate-ethanol-water; 1:1:1. Fractions containing the title compound were evaporated to afford mobile oil, yield=5.6 g (31%) ν(film) 3280, 1505, 1450, 1370, 1280, 1230, 1105, 1075, 905, 820, 750, 655 cm⁻¹ m/e 179 (M+).

EXAMPLE 18

9-N-[3-Imidazol-1-yl)propyl]aminodeoxyclavulanic acid

Benzoyl 9-N-[3-(imidazol-1-yl)propyl]-N-2-methallylaminodeoxyclavulanate (1.4 g) in ethanol (25 cm³) was hydrogenolysed at atmospheric pressure in the presence of 0.8 g of 10% palladium on carbon (prehydrogenated for 10 minutes) for a total of 4 hours. The catalyst was filtered off and washed with ethanol, then separately with aqueous ethanol (60 cm³). The aqueous washings were evaporated to an oil, which on the addition of ethanol crystallised. The crystals were filtered off and washed with ethanol then dried to afford the title compound as a white crystalline zwitterionic solid, yield=110 mg (11.5%) Rf (SiO₂/methylacetate-ethanol-water; 1:1:1)=0.25 (detection by aqueous potassium permanganate spray).

(Nujol) 1795, 1690, 1622, 1592, 1570, 1303, 1237, 1187, 1050, 1018, 987, 937, 893, 825, 752, 740 cm⁻¹.
(KBr) 1792, 1692, 1590, 1350 (shoulder) 1397, 1300, 1187, 1123, 1075, 1052, 1016, 738 cm⁻¹. δ (CD₂O) 2.09–2.33 (2H, m, N(CH₂CH₂CH₂N),

2.93 (2H, m, NCH₂(CH₂)₂N    N), 3.10 (1H, d, J 17 Hz, 6βCH), 3.57 (1H, dd, J 17 and 3 Hz, 6βCH), 3.65 and 3.73 (2H, dABq J 13.5 and 8 Hz, 9CH₂),

4.15 (2H, t, J 7 Hz, CH₂N    N), 4.76 (1H, bt, J 8 Hz, 8CH), 5.00 (1H, bs, 3CH), 5.75 (1H, d, J 3 Hz, 5αCH),

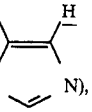

7.04 and 7.17 (2 × 1H, 2 × s, —N    N),

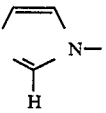

7.17 (1H, s, N    N—
              H

Preparation 19a

Benzyl 9-N(4,4-diethoxybutyl)-N-(2-methallyl)aminodeoxyclavulanate

Benzyl dichloroacetylclavulanate (8.71 g; 21.8 mmol) in dimethylformamide (50 cm$^3$) at −20° was treated dropwise with 43.6 mmol of N(4,4-diethoxybutyl)-N-(2methallyl)amine in dimethyl formamide (20 cm$^3$). The reaction was stirred for 1 hour allowing the temperature to rise to 0°. The mixture was then poured into ethylacetate (200 cm$_3$), washed with water (4×100 cm$^3$) and saturated brine (5×100 cm$^3$), dried (anhydrous magnesium sulphate) and evaporated to afford an oil. This crude product was chromatographed on silica eluting with ethylacetate-cyclohexane (2:3 grading to 1:1). Fractions were collected containing the title compound, combined fractions were evaporated to afford 6.5 g (61%) of an oil. (film) 1805, 1750, 1695, 1450, 1372, 1305, 1170, 1120, 1050, 1015, 1000, 892, 740, 697 cm$^{-1}$, δ (CDCl$_3$) 1.18 (6H, t, 7 Hz, 2×OCH$_2$CH$_3$), 1.55 (4H, bs, CH$_2$CH$_2$CH(OC$_2$H$_5$)$_2$), 1.68 (3H, s, C(CH$_3$)═CH$_2$) 2.18–2.42 (2H, m, NCH$_2$(CH$_2$)$_2$), 2.81 (2H, s, NCH(CH$_3$)), 3.00 (1H, d, J 17 Hz, 6 βCH), 3.11 (2H, d, J 7 Hz, 9CH$_2$), 3.30–3.75 (5H, bm, 2×OCH$_2$CH$_3$, 6αCH), 4.35–4.55 (1H, m, CH$_2$CH(OC$_2$H$_5$)$_2$), 4.68(1H, bt, J 7 Hz, 8CH), 4.79 (2H, bs, C(CH$_3$)═CH$_2$), 5.04 (1H, bs, 3CH ), 5.16 (2H, s, OCH$_2$C$_5$H$_5$), 5.62 (1H, d, J 3 Hz, 5αCH), 7.32 (5H, s, C$_6$H$_5$).

Preparation 19b

N-(4,4-diethoxybutyl)-N-2-methallyl amine

Aminobutyraldehyde diethylacetal (25 g; 155 mmol) was treated with ½ equivalent of methallylchloride (7.5 cm$^3$) and heated to 100° until refluxing no longer occured. The reaction was allowed to cool, ether added and the mixture washed with water and saturated brine, dried (anhydrous magnesium sulphate) and evaporated to an oil. This crude oil was chromatographed on silica eluting with methylacetate. Fractions were collected containing the title compound Rf(SiO$_2$/methylacetate) ca. 0.3 combined fractions were evaporated to a colourless oil, yield=9.5 g (57%) ν(film) 3320, 1650, 1448, 1370, 1340, 1120, 1055, 995, 890, 750 cm$^{-1}$ δ (CDCl$_3$) 1.18 (6H, t, J 6 Hz, 2×CH$_2$CH$_3$), 1.12 (1H, s, exchanges with HOD, NH), 1.40–1.82 (4H, m, CH$_2$CH$_2$O (CH$_2$CH$_3$)$_2$), 1.63 (3H, s, C(CH$_3$)═CH$_2$), 2.50–2.70 (2H, m, NCH$_2$(CH$_2$)$_2$), 3.13 (2H, bs, NCH$_2$C(CH$_3$)═CH$_2$), 3.28–3.85 (4H, m, 2×OCH$_2$), 4.4–4.57 (1H, m, CH$_2$CH(OCH$_2$CH$_3$)$_2$), 4.72–4.90 (2H, m, ═CH$_2$).

EXAMPLE 19

9-N-(4,4-Diethoxybutyl)amino deoxyclavulanic acid

Benzyl 9-N-diethoxybutyl-N-methallylamino deoxyclavulanate (2 g; 4.11 mmol) in ethanol (20 cm$_3$) was hydrogenolysed at atmospheric pressure with 0.7 g of 10% palladium on carbon (prehydrogenated for 10 minutes) for 25 minutes. The catalyst was filtered off and washed with ethanol. The filtrate was evaporated to afford an oil. Scratching afforded crystals to which acetonitrile was added and the resultant crystals filtered, washed with acetonitrile and dried to afford 0.6 g (43%) of the title compound Rf (SiO$_2$/ethylacetate-ethalalcohol-water; 5:4:2)=0.46 ν (nujol) 1795, 1695, 1615, 1305, 1290, 1190, 1122, 1047, 1018, 980, 950, 928, 892, 748 cm$^{-1}$ δ (D$_2$O) 1.21 (6H, t, J 7 Hz, 2×CH$_2$CH$_3$), 1.67-1.82 (4H, m, NCH$_2$(CH$_2$)$_2$CH), 3.0–3.11 (2H, m, NCH$_2$(CH$_2$)$_2$), 3.28 (1H, d, J 17 Hz, 6βCH), 3.55–3.86 (7H, broad m, 2×OCH$_2$CH$_3$, 9CH$_2$, 6βCH), 4.65–4.71 (1H, m, CH(OC$_2$H$_5$)$_5$), 4.84 (1H, t, J 8 Hz, 8CH), 5.05 (1H, bs, 3CH), 5.81 (1H, d, J 3 Hz, 5αCH).

Preparation 20a

Benzyl 9N-(4-acetoxybutyl)methallylaminodeoxyclavulanate

Benzyl 9-0-dichloroacetylclavulanate (4.944 g, 12.36 mmol) in dry dimethylformamide (30 ml) at 0° C. was treated dropwise with (4-acetoxybutyl)methyallyamine (4.5732 g, 24.72 mmol) in dry dimethylformamide (10 ml). The reaction was monitored by thin layer chromatography and when the starting material had been consumed (ca. 2.5 hr) the reaction was diluted with ethyl acetate and washed with brine (3×). The organic phase was concentrated and extracted wuth tartaric acid (2 g in 50 ml water) four times. The aqueous extracts were combined and stirred vigorously with ethyl acetate (200 ml). A solution of sodium hydroxide was added dropwise until the aqueous layer was at pH7.0. The organic layer was evaporated after being dried (MgSO$_4$) affording the title compound as an oil 2.953 g (52% yield).

ν$_{max}$ (film) 1808, 1743 br, 1699 cm$^{-1}$.

EXAMPLE 20

9-N-(4-Acetoxybutyl)aminodeoxyclavulanic acid

Benzyl 9-N-(4-acetoxybutyl)methallylaminodeoxyclavulanate (2.953 g, 6.476 mmol) in ethanol (20 ml) containing Pd/c (10%, 0.8 g) was hydrogenated for 15 min, all starting material had been consumed by this time as judged by thin layer chromatography. The reaction was filtered and the catalyst washed with water. The aqueous washings were concentrated and the title compound crystallised out upon the addition of acetone, 0.73 g (36% yield).

ν$_{max}$ (Nujol) 1812, 1718, 1694, 1618 and 1583 cm$^{-1}$.

δ (D$_2$O) 1.52–1.86 (4H, m, CH$_2$CH$_2$ CH$_2$CH$_2$), 2.03 (3H, s, CH$_3$), 2.88–3.21 (3H, m, NCH$_2$(CH$_2$)$_3$ and 6β—CH), 3.40–3.81 (3H, m, NCH$_2$CHC and 6β—CH), 3.96–4.18 (2H, m, CH$_2$O), 4.77 (1H, dt, J 8 and 1H$_3$, 8—CH, partly obscured by HOD), 4.96 (1H, d, J 1 Hz, 3—CH) and 5.74 (1H, d, J 3H$_3$, 5—CH).

Preparation 21 (a)

4-Methyl-4-nitro-1-tosyloxypentane

A solution of 4-methyl-4-nitro-1-pentanol (7 gm) in pyridine (40 ml) was cooled in an ice bath and treated with tosyl chloride (19 gm) added in portions over 20 mins. When the addition was complete the mixture was stirred at room temperature for 1 hr. Water (20 ml) was then added and the mixture stirred for 15 mins. The mixture was poured into water and extracted twice with ethyl acetate. The ethyl acetate solution was washed successively with water, citric acid solution, water, sodium bicarbonate solution, water and brine. The solution was dried over magnesium sulphate and evaporated. The product was obtained by crystallisation from ether: 60/80 petroleum ether. Yield 8.18 gm.

ν$_{max}$ (nujol) 1530 1360 1175 cm$^{-1}$.

δ (CDCl$_3$) 1.53(6H, s) 1.5–2.1(4H, s) 2.44(3H,s), 4.01(2H,t,J=6 Hz), 7.34(2H,d,J=8 Hz), 7.77(2H,d,J=8 Hz).

Preparation 21 (b)

N-Benzyl-4-methyl-4-nitro-pent-1-ylamine

To a stirred mixture of benzylamine (9 ml) and triethylamine (5.5 ml) was added 4-methyl-4-nitro-1-tosyloxypentane (11.9 gm). The mixture was then heated to 70° C. for 2 hrs. The mixture was cooled and partitioned between ethyl acetate and water, the ethyl acetate solution was washed twice with water, then with brine and dried over magnesium sulphate. The solution was evaporated and the product isolated by column chromatography of the residue using gradient elution (Kieselgel; 1:1 60/80 petroleum ether:ethyl acetate going to ethyl acetate). Yield 6.89 gm.

$\nu_{max}$ (film) 1535, 1350 cm$^{-1}$.

δ (CDCl$_3$) 1.2–1.6(3H,m), 1.53(6H,s), 1.8–2.05(2H,m), 2.59(2H, t, J=7 Hz), 5.72(2H,s), 7.25(5H,s).

Preparation 21 (c)

Benzyl 9-[N-benzyl-N-(4-methyl-4-nitro)pentyl]aminodeoxyclavulanate

A solution of benzyl 9-0-dichloroacetylclavulanate (4.00 gm) in dimethylformamide (25 ml) was cooled to −12° C., and a solution of N-benzyl-4-methyl-4-nitro-pent-1-ylamine (4.72 gm) in dimethylformamide (15 ml) was added dropwise at such a rate that the temperature did not rise above −10° C. When the addition was complete the mixture was stirred at −10° C. for 1 hr. The solution was poured into toluene (120 ml) and the toluene solution was washed with five portions of water, and then brine. The solution was dried over magnesium sulphate and evaporated. The product was isolated by column chromatography of the residue using gradient elution (Kieselgel:3:1 going to 1:1 60/80 petroleum ether:ethyl acetate). Yield 3.27 gm.

$\nu_{max}$ (CHCl$_3$) 1805, 1750, 1695, 1535 cm$^{-1}$.

δ (CDCl$_3$) 1.1–1.4 (2H,m), 1.50(6H, s), 1.65–2.0(2H, m), 2.31(2H,t,J=7 Hz), 2.97(1H, d,J=17 Hz), 3.41(2H, s), 3.42(1H,dd,J=3 and 17 Hz), 4.68(1H,t,J=7 Hz), 5.04(1H,s), 5.16(2H,s), 5.61(1H,d,J=3 Hz), 7.23(5H, s) 7.31(5H,s).

EXAMPLE 21

9-N-[4-Methyl-4-nitropentyl]aminodeoxyclavulanic acid

A solution of benzyl 9-[N-benzyl-N-(4-methyl-4-nitropentyl]aminodeoxyclavulanate (2.0 gm) in a mixture of tetrahydrofuran (30 ml), ethanol (40 ml) and water (30 ml) was hydrogenated over 10% palladium charcoal (700 mgs) for 1½ hours. The solution was filtered through Celite and the combined filtrates were evaporated to about 3 ml. and triturated with ethanol. The crystalline solid was filtered off, washed with ethanol and dried under vacuum. Yield 485 mgs; m.p. 205° C. (with decomposition).

$\nu_{max}$ (KBr) 1790, 1694, 1610, 1535 cm$^{-1}$.

δ (D$_2$O) 1.5–2.1(4H, m), 1.69(6H, s), 3.02(2H,t,J=7 Hz), 3.12(1H,d,J=17 Hz), 3.06(1H,dd,J=3 and 17 Hz), 3.73(2H,d,J=7 Hz), 4.79(1H, broad t, J=7 Hz), 5.02(1H,s), 5.78(1H,d,J=3 Hz).

(Found: C, 51.44; H, 6.44; N, 12.70%; C$_{14}$H$_{21}$N$_3$O$_6$ requires: C, 51.37; H, 6.47; N, 12.84%).

Preparation 22 (a)

N-Benzyl-N′N′-dimethylcarbamoyl ethylenediamine

A stirred mixture of N-benzyl ethylenediamine (6.0 gm) in chloroform (20 ml) and sodium hydroxide (1.6 gm) in water (20 ml) was cooled to −5° C. A solution of dimethyl carbamoyl chloride (3.7 ml) in chloroform (20 ml) was added at such a rate that the temperature did not rise above 0° C. When the addition was complete the stirred mixture was allowed to warm to room temperature for 1 hr. The organic phase was separated, washed with water, then brine and dried over magnesium sulphate. The solution was evaporated and the product purified by column chromatography using gradient elution (Kieselgel:ethyl acetate going to 1:1 ethyl acetate:methanol as eluent). Yield 4.92 gm of a yellow oil.

$\nu_{max}$ (film) 3330, 1630, 1535 cm$^{-1}$.

δ (CDCl$_3$) 2.30(1H,s), 2.68–2.9(2H,m), 2.85(6H,s),3.2–3.4(2H,m) 3.76(2H,s),5.10(1H, broad s), 7.27(5H,s).

Preparation 22 (b)

Benzyl 9-[N-benzyl-N-(N′N′-dimethylureido)ethyl]aminodeoxyclavulanate

A stirred solution of 9-0-dichloroacetylclavulanate (4.00 gm) in dimethylformamide (25 ml) was cooled to −12° C., and a solution of N-benzyl-N′N′-dimethylcarbamoyl ethylenediamine (4.42 gm) in dimethylformamide (15 ml) was then added dropwise at such a rate that the temperature did not rise above −10° C. When the addition was complete the solution was stirred at −10° C. for 1 hr and then poured into toluene (100 ml). The toluene solution was washed with six portions of water, then brine, and dried over magnesium sulphate. The solution was evaporated to about 10 ml and the product was isolated by column chromatography of the solution (Kieselgel; ethyl acetate as eluent). Yield 1.74 gm of pale yellow oil.

$\nu_{max}$ (CHCl$_3$) 3420, 1800, 1750, 1695, and 1638 cm$^{-1}$.

δ (CDCl$_3$) 2.54(2H,t,J=6 Hz), 2.80(6H, s), 2.96(1H,d,J=17 Hz), 3.1–3.3(4H,m),3.42(1H,dd,J=3 and 17 Hz), 3,43(2H,s)4.68(1H, broad t, J=7 Hz), 4.84(1H, broad s), 5.06(1H,s),5.17(2H,s),5.61(1H,d,J=3 Hz), 7.23(5H,s),7.31(5H,s).

EXAMPLE 22

9-[N-benzyl-N-(N′N′-dimethylureido)ethyl]aminodeoxyclavulanic acid and 9-N-(N′N′-dimethylureido)ethylaminodeoxyclavulanic acid A solution of benzyl 9-[N-benzyl-N-(N′N′-dimethylureido)ethyl]aminodeoxyclavulanate in a mixture of tetrahydrofuran (30 ml) ethanol (40 ml) and water (30 ml) was hydrogenated over 10% palladium charcoal (600 mgs) for 1¼ hrs. The solution was filtered through Celite and the filter cake washed with water. The combined filtrates were evaporated and the products separated by column chromatography using gradient elution (Kieselgel; 5:4:2 going to 3:6:4 ethyl acetate:isopropanol:water). Eluted were:

9-[N-benzyl-N-(N′N′-dimethylureido)ethyl]aminodeoxyclavulanic acid, 326 mg as a light brown, freeze-dried foam.

$\nu_{max}$ (KBr) 1785, 1690, 1610 cm$^{-1}$.

δ (D₂O) 2.78(6H,s), 3.08(1H,d,J=17 Hz), 3.05–3.25(2H,m), 3.3–3.5 (2H,m), 3.58(1H, dd,J=3 and 17 Hz), 3.82(2H,d,J=8 Hz), 4.20(2H,s), 4.89(1H, broad, J=8 Hz), 5.02(1H,s), 5.77(1H, d,J=3 Hz) 7.45(5H,s).

9-N-(N'N'-dimethylureido)ethylaminodeoxyclavulanic acid, 191 mg as a white crystalline solid.

$v_{max}$ (KBr) 1790, 1690, 1620 (broad) cm⁻¹.

δ (D₂O) 2.87 (6H,s) 3.11 (2H,t,J=7 Hz), 3.14(1H,d,J=17 Hz) 3.46 (2H,t,J=7 Hz) 3.61(1H,dd,J=3 and 17 Hz), 3.75(2H,d,J=8 Hz) 4.84 (1H, broad t, 5=8 Hz), 5.03(1H,s), 5.80(1H,d,J=3 Hz), (Found: C, 47.30; H, 6.76; N, 16.68%; $C_{13}H_{22}N_4O_5$ (monohydrate) requires; C, 47.27; H, 6.71; N, 16.96%).

Preparation 23 (a)

1-chloro-2-phenylsulphonyl ethane m-Chloroperoxybenzoic acid (21.0 g; 121.7 mmol) was added portion wise to a solution of 2-chloroethyl phenylsulphide (8.5 ml; 58 mmol) in dichloromethane (200 ml) at 0° C. After the addition was complete the reaction mixture was allowed to warm to room temperature and stirred for ¼ hr. Dichloromethane (100 ml) was then added and the organic phase washed with saturated sodium bicarbonate solution (3×300 ml), saturated brine (2×300 ml) and dried over anhydrous magnesium sulphate. Removal of the solvent gave the title compound as a white crystalline solid, in 99% yield.

$v_{max}$ (1% CHCl₃) 1590, 1450, 1330, 1315, 1310 and 1150 cm⁻¹.

$δ_H$ (CDCl₃) 3.39–3.95(4H, m,C$\underline{H}_2$C$\underline{H}_2$Cl),

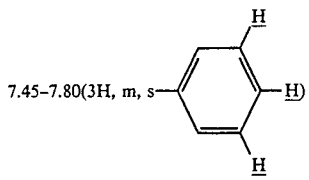

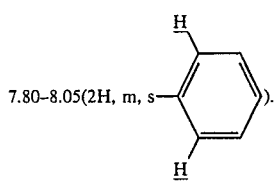

Preparation 23 (b)

N-(2-phenylsulphonylethyl)methallylamine

A solution of methallylamine (8.0 g; 1.12 mol), in toluene (20 ml) was added dropwise to a solution of 1-chloro-2-phenylsulphonylethane (11.54 g; 56.4 mmol) in toluene (100 ml) at 0° C. When the addition was complete the reaction mixture was allowed to warm to room temperature and stirred for 1 hr. Thin layer chromatography indicated that all of the starting material had been consumed. Ether (150 ml) was added and the precipitate filtered off. Removal of the solvent from the filtrate produced a colourless oil which was subjected to silica gel column chromatography using ethyl acetate as eluent. Fractions containing the component Rf=0.37 (ethyl acetate) were combined and evaporated to give the title amine as a colourless oil, in 75% yield.

$v_{max}$ (1% CHCl₃) 1450, 1320, 1310 and 1145 cm⁻¹.

$δ_H$ (CDCl₃) 1.61(1H, s, NH), 1.67(3H, s, CH₂C:CH₂(C$\underline{H}_3$), 2.85–3.06 (2H,m,$\overline{O}_2$S—C$\underline{H}_2$CH₂N), 3.09(2H,s,C$\underline{H}_2$C:CH₂(CH₃)), 3.20–3.40(2H,m,O₂S—C$\underline{H}_2$CH₂),4.49(2H, broad s, CH₂C:C$\underline{H}_2$(CH₃)),

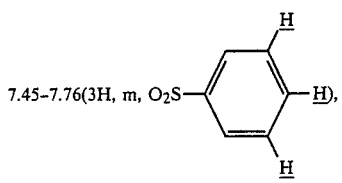

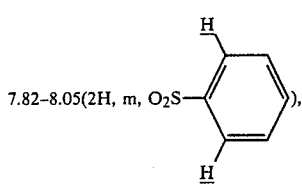

[singlet δ=1.61 disappeared on addition of D₂O].

Preparation 23 (c)

p-Nitrobenzyl 9-N-methallyl-N-[2-(phenylsulphonyl)ethyl-]aminodeoxyclavulanate A solution of N-(2-phenylsulphonylethyl)methallylamine (8.7 g; 36.4 mmol.) in dimethylformamide (30 ml) was added dropwise over ¼ hr to a solution of p-nitrobenzyl 9-0-dichloroacetylclavulanate (8.13 g; 18.27 mmol.) in dimethylformamide (90 ml) at −30° C. The reaction mixture was then stirred at −30° C. for ¼ hr, then allowed to warm to room temperature, and stirred for a further 4 hr. Thin layer chromatography indicated that all of the starting material had been consumed. The mixture was poured into ethyl acetate (150 ml) and the organic phase washed with water (3×200 ml), saturated brine (2×200 ml) then dried over magnesium sulphate. Removal of the solvent produced a yellow oil which was subjected to silica gel column chromatography using ethyl acetate:cyclohexane (2:3) as eluent. Fractions containing the component Rf=0.31 (ethyl acetate:cyclohexane; 2:3) were combined and evaporated to give the title compound as a pale yellow oil in 20% yield.

$v_{max}$(CHCl₃) 1810, 1760, 1710, 1700, 1525, 1355, 1310 and 1155 cm⁻¹.

$δ_H$ (CDCl₃). 1.57(3H, S, CH₂C:CH₂(C$\underline{H}_3$)); 2.65–3.35(7H, m, 6β—C$\underline{H}$; C$\underline{H}_2$C$\underline{H}_2$—SO₂— and C$\underline{H}_2$C:CH₂(CH₃)); 3.50(1H, dd, J17.2 and 3 Hz, 6α—C$\underline{H}$), 4.62(1H, t, J8 Hz, 8—C$\underline{H}$, partially obscured by broad S at δ=4.71); 4.71(2H, broad s, CH₂C:C$\underline{H}_2$(CH₃)), 5.09(1H, broad S, 3—C$\underline{H}$),

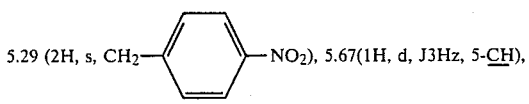

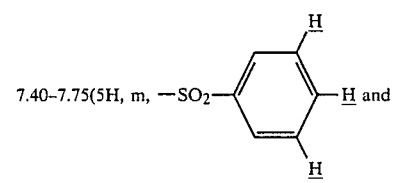

-continued

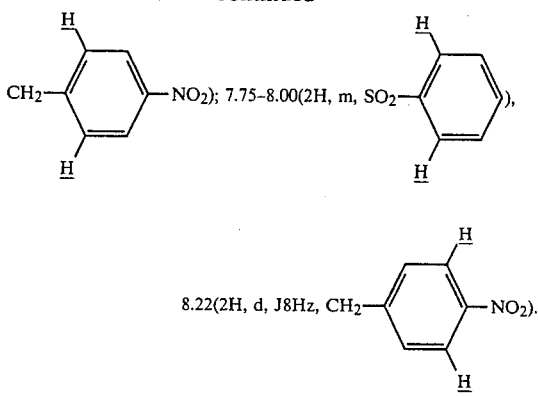 ; 7.75–8.00(2H, m, SO₂—

8.22(2H, d, J8Hz, CH₂— 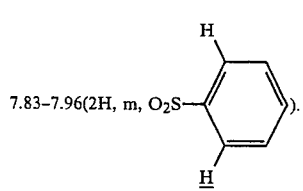 —NO₂).

EXAMPLE 23

9-N-[2-(phenylsulphonyl)ethyl]aminodeoxyclavulanic acid

A solution of p-nitrobenzyl 9-N-methallyl-N-[2-(phenylsulphonyl)ethyl]aminodeoxyclavulanate (0.216 g; 0.39 mmol) in tetrahydrofuran (10 ml) containing water (1 ml) was added to a prehydrogenated suspension of 10% palladium on carbon (0.1 g) in tetrahydrofuran (3 ml). The mixture was hydrogenated for 1¼ hr after which thin layer chromatography indicated the ester had been consumed. The catalyst was filtered off and washed separately with tetrahydrofuran (15 ml) and water (30 ml). The aqueous washings were evaporated to give the title compound as a colourless glass, crystallised from hot ethanol in 39% yield.

$\nu_{max.}$ (KBr) 1795, 1690, 1600, 1305 and 1145 cm⁻¹.

$\delta_H$ (DMSO/D₂O). 2.93(1H, d, J16 Hz, 6β—CH), 3.06(2H, t, J7 Hz, NCH₂CH₂SO₂—), 3.47(2H, d, J7.8 Hz, 9—CH₂), 3.50(1H, dd, J16 and 3 Hz, partially obscured by d, δ=3.47, 6α—CH), 3.56–3.69(2H, m, CH₂CH₂SO₂—), 4.53–4.64(2H, m, 8—CH and 3—CH), 5.63(1H, d, J3 Hz, 5—CH), 7.63–7.74(2H, m, O₂S— 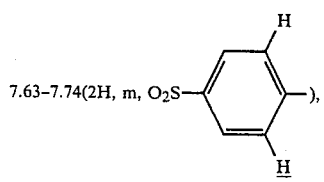 ), 7.74–7.83(1H, m, O₂S— 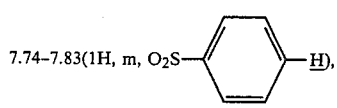 H), 7.83–7.96(2H, m, O₂S— 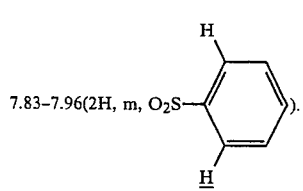 ).

Preparation 24 (a)

Benzyl 9-N-benzyl-N-(3-N-benzylcarbamoylprop-1-yl)aminodeoxyclavulanate

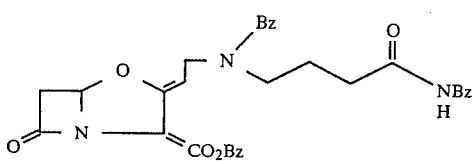

A solution of 4-(N-benzylamino)-N-benzylbutanamide (2.0 g; 7.1 mmol) in dimethylformamide (5 ml) was added dropwise over ¼ hr to a solution of benzyl 9-0-dichloroacetylclavulanate (1.5 g; 3.7 mmol) in dimethylformamide (15 ml) at −20° C. After the addition was complete the reaction mixture was stirred from −20° C. to −10° C. for 1½ hr then to room temperature for a further ½ hr. The solution was then poured into ethyl acetate and the organic phase washed with water (3×) and saturated brine (1×). After being dried over magnesium sulphate the solvent was removed in vacuo to yield an orange oil which was subjected to silica gel column chromatography using ethyl acetate as eluent. Fractions containing the component Rf=0.27 (ethyl acetate) were combined and evaporated to produce the title compound in 18% yield.

$\nu_{max}$ (5% CHCl₃) 1800, 1745, 1660 and 1510 cm⁻¹.

$\delta_H$ (CDCl₃)

1.77 (2H, tt, J7Hz, CH₂CH₂CH₂C(=O)—), 2.02–2.47 (4H, m, CH₂CH₂CH₂C(=O)—), 2.92(1H, d, J17.5 Hz,6β—CH) 3.11(2H,d,J7.5 Hz, 9—CH₂), 3.36(1H,dd, J17.5 and 2.5 Hz, 6α—CH), 3.38(2H, s,N—CH₂Ph), 4.31(2H,d,J6 Hz CONHCH₂Ph, addition of D₂O caused the peak to collapse to a singlet δ=4.30),4.63(1H,t,J8 Hz,8—CH), 5.00(1H, s,3—CH),5.13(2H,s,CO₂CH₂Ph), 5.56(1H,d,J2.5 Hz,5—CH), 6.05(1H,m,NH addition of D₂O caused peak to disappear) 7.05–7.45(15H,m,ArH).

Preparation 24 (b)

9-N-benzyl-N-(3-N-benzylcarbamoylprop-1-yl)aminodeoxyclavulanic acid

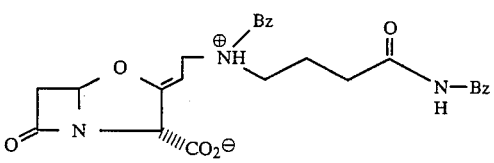

Benzyl 9-N-benzyl-N-(3-N-benzylcarbamoylprop-1-yl)aminodeoxyclavulanate (0.20 g, 0.36 mmol) in ethanol (8 ml) was added to a suspension of 10% palladium on carbon (0.07 g) in ethanol (2 ml) which had been prehydrogenated for ¼ hr. The mixture was hydrogenated at room temperature for 1 hr. The catalyst was filtered off and washed with 15% aqueous ethanol then the solvent removed from the combined filtrates to give a yellow foam which was subjected to silica gel column chromatography using ethyl acetate:ethanol:water (5:4:2) as eluent. Fractions that contained the component Rf=0.32 (ethyl acetate:ethanol:water: 5:4:2) were combined and evaporated in vacuo to give the title compound in 50% yield.

$v_{max}$ (KBr) 1790, 1620 and 1550 cm$^{-1}$.

$\delta_H$ (acetone D$_6$) 2.05(2H, m,CH$_2$CH$_2$C$\underline{H}_2$CO), 2.19–2.34(2H,m,CH$_2$CH$_2$C$\underline{H}_2$CO), 2.84(2H,m,C$\underline{H}_2$CH$_2$CH$_2$CO, partially obscured by d, $\delta$=2.94), 2.94(1H,d,J16.5 Hz, 6β—C$\underline{H}$) 3.43 and 3.56(2H,d ABq, J 8 and 15 Hz, 9—C$\underline{H}_2$, partially obscured by dd, δ=3.43),3.43(1H, dd, J 3 and 16 Hz, 6α—C$\underline{H}$), 4.02 and 4.20(2H, ABq, J13 Hz, N—C$\underline{H}_2$Ph), 4.31 and 4.38(2H, ABq, J15 Hz, NHC$\underline{H}_2$Ph), 4.84(1H, s, 3—C$\underline{H}$), 4.91(1H, t, J8 Hz,8—C$\underline{H}$), 5.70(1H, d, J2.5 Hz,5—C$\underline{H}$), 7.14–7.34(5H,m,N—C$\underline{H}_2$Ph),

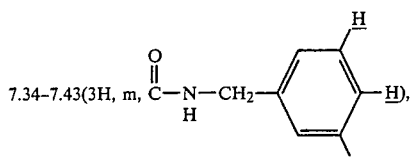
7.34–7.43(3H, m,

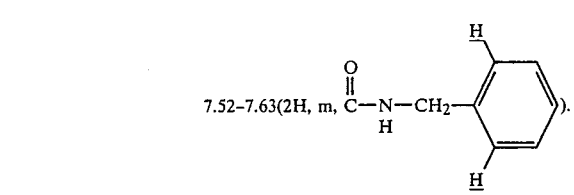
7.52–7.63(2H, m,

EXAMPLE 24

9-N-(3-N-benzylcarbamoylprop-1-yl)amino deoxyclavulanic acid

9-N-benzyl-N-(3-N-benzylcarbamoylprop-1-yl)aminodeoxyclavulanic acid is subjected to hydrogenation as described in Example 9 to yield the title compound.

Preparation 25 (a)

N-Benzyl-3-bromopropanamide

BrCH$_2$CH$_2$COCl + H$_2$NBz → BrCH$_2$CH$_2$CONHBz

A solution of benzylamine (6.49 ml) and triethylamine (8.26 ml) in ethyl acetate (60 ml) was added dropwise to a solution of 3-bromopropionyl chloride (6 ml) in ethyl acetate (10 ml) at 0° C. The reaction mixture was stirred to room temperature for 1 hr. The organic phase was washed with water (2×150 ml), saturated brine (150 ml) and dried over magnesium sulphate. Removal of the solvent produced the amide as a crystalline solid.

$v_{max}$. (5% CHCl$_3$) 1670 and 1510 cm$^{-1}$. δH, (CDCl$_3$) 2.7H and 3.60 (4H, 2×t, J 6 Hz, C$\underline{H}_2$e,uns/CH/ $_2$CO), 4.41 (2H, d, J 6 Hz, N—C$\underline{H}_2$Ph), 5.80–6.30 (1H, broad s, N$\underline{H}$), 7.27 (5H, s, Ar$\underline{H}$).

Preparation 25 (b)

3-(N-Methallylamino)-N-benzylpropanamide

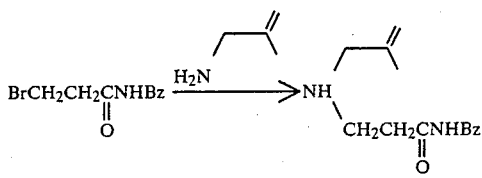

N-Benzyl-3-bromopropanamide (6 g), methallylamine (1.9 g) and triethylamine (3.5 ml) in dimethylformamide (12 ml) were heated together under reflux for 2¼ hr, then poured into ethyl actate (100 ml). The organic phase was washed with water (2×100 ml), saturated brine (100 ml) and dried over magnesium sulphate. Removal of the solvent under reduced pressure gave a yellow oil which produced the title compound in 17% yield after column chromatography using ethyl acetate:ethanol (1:1) as eluent.

$v_{max}$. (5% CHCl$_3$) 1660, 1510 cm$^{-1}$. δH (CDCl$_3$) 1.62 (3H, s, CH$_2$C:CH$_2$(C$\underline{H}_3$)), 1.65 (1H, s, disappeared on addition of D$_2$O, N$\underline{H}$), 2.35 and 2.83 (2H, 2×t, J 6 Hz, C$\underline{H}_2$CH$_2$CO), 3.20 (2H, broad s, C$\underline{H}_2$C:CH$_2$(CH$_3$)), 4.39 (2H, d, J 6 Hz, NC$\underline{H}_2$Ph), 4.76 (2H, broad s, CH$_2$C:C$\underline{H}_2$(CH$_3$)), 7.24, (5H, s, Ar$\underline{H}$), 7.85–8.30 (1H, broad s, N$\underline{H}$CO).

Preparation 25 (c)

Benzyl 9-N-methallyl-N-(3-N-benzylcarbamoyleth-1-yl)aminodeoxyclavulanate

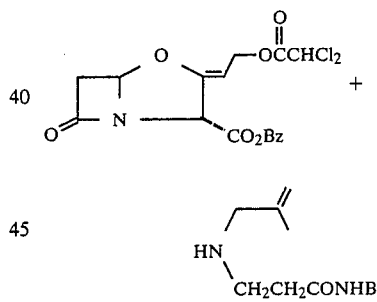

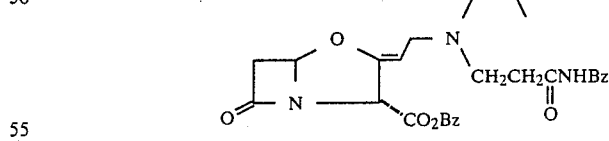

A solution of 3-(N-methallylamino)-N-benzylpropanamide (7.12 g; 30.6 mmol) in dimethylformamide (10 ml) was added dropwise to a solution of benzyl 9-0-dichloroacetylclavulanate (6.14 g; 15.3 mmol) in dimethylformamide (30 ml) at −30° C. The reaction mixture was stirred from −30° to −20° C. for 1 hr then at room temperature for 1½ hr. The mixture was poured into ethylacetate and the organic phase washed with water (3×), saturated brine (1×), then dried over magnesium sulphate. Removal of the solvent under reduced pressure produced a yellow oil which was subjected to silica gel column chromatography using ethyl acetate as eluent. The fractions containing the component Rf=0.49 (ethyl acetate) were combined and evaporated to give the desired amine as a pale yellow oil in 35% yield.

$\nu_{max}$. (5% CHCl$_3$) 1790, 1750 and 1660 cm$^{-1}$. $\delta$H (CDCl$_3$) 1.44 (3H, s, CH$_2$C:CH$_2$(C$\underline{H}_3$)), 2.39 and 2.52 (4H, 2×t, J 6 Hz, NC$\underline{H}_2$C$\underline{H}_2$CO), 2.79 (2H, s, C$\underline{H}_2$C:CH$_2$(CH$_3$)), 3.00 (1H, d, J 16.5 Hz, 6β—C$\underline{H}$), 3.11 (2H, d, J 7 Hz, 9—C$\underline{H}_2$), 3.46 (1H, dd, J 16.5 and 2.8 Hz, 6α—C$\underline{H}$), 4.40 (2H, d, J 6 Hz, N—C$\underline{H}_2$Ph), 4.51 (1H, dt, J 7.0 and 1 Hz, 8—C$\underline{H}$), 4.73 and 4.78 (2H, 2×s, CH$_2$C:C$\underline{H}_2$(CH$_3$)), 5.02 (1H, d, J 1 Hz, 3—C$\underline{H}$), 5.13 and 5.23 (2H, ABq, J 7 Hz, CO$_2$C$\underline{H}_2$Ph), 5.61 (1H, d, J 2.8 Hz, 5—C$\underline{H}$), 7.20–7.45 (10H, m, Ar$\underline{H}$), 8.45 (1H, broad s, N$\underline{H}$).

EXAMPLE 25

9-N-(3-N-Benzylcarbamoyleth-1-yl)aminodeoxyclavulanic acid

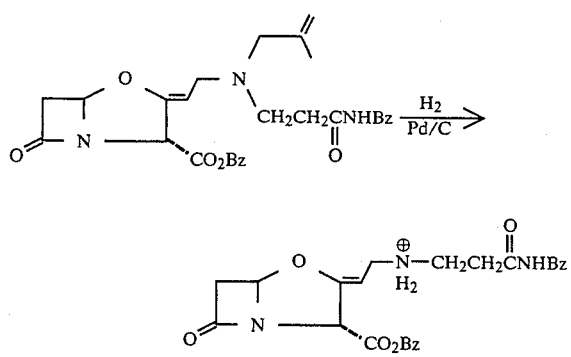

A solution of benzyl 9-N-methallyl-(3-N-benzylcarbamoyleth-1-yl)aminodeoxyclavulanate (1.2 g; 2.4 mmol) in ethanol:tetrahydrofuran (2:1; 10 ml) was added to a prehydrogenated suspension of 10% palladium on carbon (0.4 g) in ethanol:tetrahydrofuran (2:1; 16 ml). The mixture was hydrogenated at room temperature for ¾ hr then the catalyst filtered off, and washed with aqueous ethanol (25 ml). The combined filtrates were evaporated in vacuo to a brown foam; which on column chromatography using ethyl acetate:ethanol (1:1) as eluent gave the title compound (Rf=0.57; ethyl acetate:ethanol; 1:1) crystallised from hot ethanol in 29% yield.

$\nu_{max}$. (KBr) 1795, 1690, 1665, 1610 and 1575 cm$^{-1}$. $\delta$H, (DMSO/D$_2$O) 2.54 and 3.07 (4H, 2×t, J 7 Hz, NC$\underline{H}_2$C$\underline{H}_2$CO), 2.97 (1H, d, J 17 Hz, 6β—C$\underline{H}$), 3.44 (1H, dd, J 2.7 and 17 Hz, 6α—C$\underline{H}$), 3.55 (2H, d, J 7.8 Hz, 9—C$\underline{H}_2$) 4.23 (2H, s, C$\underline{H}_2$Ph) 4.65 (1H, broad t, J 7 Hz, 8—C$\underline{H}$), 4.71 (1H, broad s, 3—C$\underline{H}$), 5.64 (1H, d, J 2 Hz, 5—C$\underline{H}$) 7.17–7.35 (5H, m, Ar$\underline{H}$).

Preparation 26

Benzyl 9-N-(indol-3'-ylethyl)-N-benzylaminodeoxyclavulanate

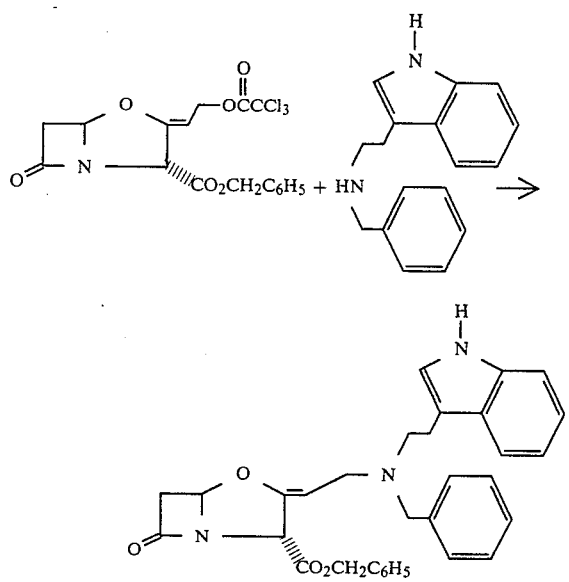

Benzyl trichloroacetylclavulanate (12.7 g; 29 mmol) in dimethylformamide (70 cm$^3$) at −20° was treated with 1.9 equivalents of 3-(2-benzylaminoethyl)indole (13.9 g) in dimethylformamide (40 cm$^3$), dropwise. Stirred for 1¾ hours at 0° when the reaction mixture was poured into ethyl acetate (250 cm$^3$) and washed with water (5×100 cm$^3$) and saturated brine (5×100 cm$^3$), dried (anhydrous magnesium sulphate) and evaporated to an oil. This crude oil was chromatographed on silica eluting with ethyl acetate-cyclohexane (1:1). Fractions were collected containing the title compound and these were evaporated to afford 6 g of an oil.

EXAMPLE 26

9-N-(2-Indol-3'-ylethyl)aminodeoxyclavulanic acid

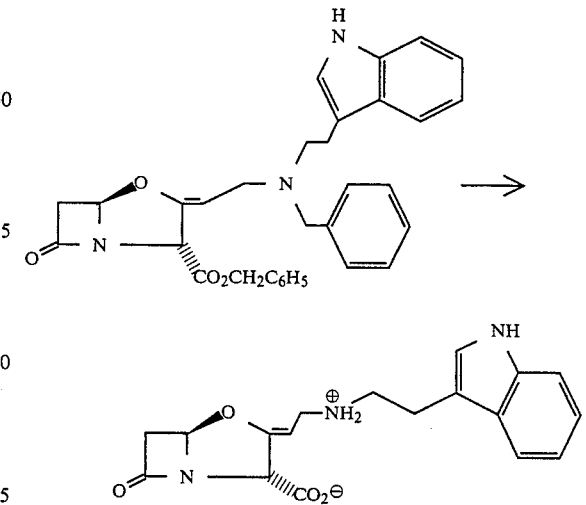

Benzyl 9-N-(2-indol-3'-ylethyl)benzyl aminodeoxyclavulanate (6 g) in ethanol/tetrahydrofuran (40 cm$^3$;

1:1) and water (5 cm³), was hydrogenolysed at atmospheric pressure with 2 g of 10% Pd/C for 2 hours when 10 cm³ water was added and hydrogenolysis continued for a further 2 hours. The catalyst was filtered and washed with aqueous ethanol. Evaporation afforded the title compound as a white crystalline solid from acetone. Yield=0.36 g ν (nujol) 3170, 1818, 1600, 1625, 1610, 1580 cm⁻¹, ν (KBr) 3170, 1810, 1700, 1630–1605 (br) 1575, 1467, δ (DMSO D6/D₂O) 2.95(1H, d, J 16.5 Hz, 6βC<u>H</u>), 2.9–3.1(2H, m, NC<u>H₂</u>CH₂), 9C<u>H₂</u> and 6αC<u>H</u> obscured by HOD, 4.52(1H, s, 3C<u>H</u>), 4.64(1H, t, J 7 Hz, 8C<u>H</u>), 5.63(1H, d, J2.5 Hz, 5αC<u>H</u>),

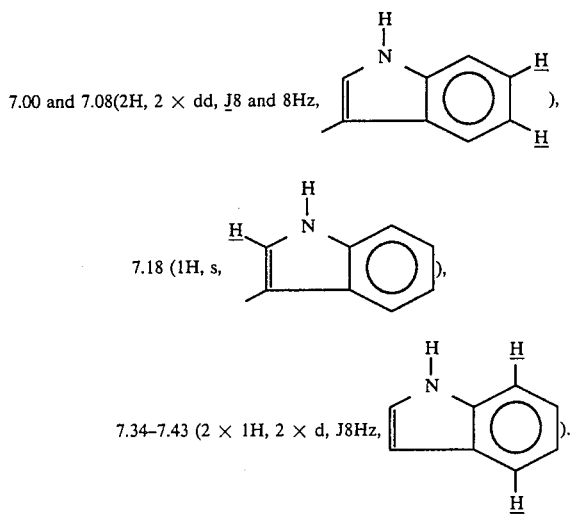

7.00 and 7.08(2H, 2 × dd, J8 and 8Hz, 7.18 (1H, s, 7.34–7.43 (2 × 1H, 2 × d, J8Hz,

Preparation 27

Benzyl 9-N-(2-chloro-2-phenylethyl)-N-benzylaminodeoxyclavualanate

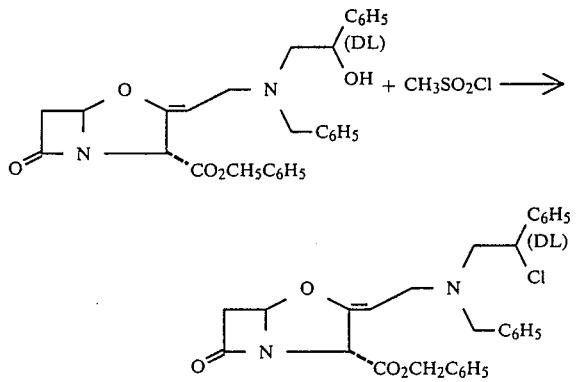

Benzyl 9-N-(2-hydroxy-2-phenylethyl)-N-benzylaminodeoxyclavulanate (1.03 g, 2.07 mmol) in dichloromethane (15 cm⁻³) at 20° C. was treated with pyridine (2 eq.; 0.33 cm⁻³) followed by 2 equivalents of methane sulphonylchloride (0.32 cm⁻³) and stirred for two hours. The mixture was evaporated, redissolved in ethyl acetate and washed with saturated brine, dried (anhydrous magnesium sulphate) and evaporated to low volume. This crude product was chromatographed on silica eluting with ethylacetate/cyclohexane 1:2. Fractions containing the title compound were evaporated Rf (SiO₂/ethylacetate-cyclohexane; 1:2)=0.5 to afford 250 mg (23%) of an oil. ν (film) 1800, 1750, 1690, 750, 695 cm⁻¹. δ (CDCl₃) 2.82–3.09 (3H, br. m, NC<u>H₂</u>CHCl and 6β—C<u>H</u>), 3.16–3.25 (2H, m, 9C<u>H₂</u>), 3.44 and 3.47 (1H, 2×dd, 6α—C<u>H</u>, J 16 and 3 Hz), NC<u>H₂</u>C₆H₅ partially obscured, 4.61 and 4.69 (1H, 2×dt, J 7 and 1 Hz, 8C<u>H</u>), 4.83 and 4.85 (1H, 2×t, J 6.5 Hz, NCH₂C<u>H</u>Cl), 5.05 (1H, m, 3C<u>H</u>) [5.14 and 5.21 (ABq, J 11 Hz) and 5.15 and 5.23 (ABq, J 11 Hz), 2H, CO₂C<u>H₂</u>C₆H₅] 5.59–5.68 (1H, m, 5α—C<u>H</u>), 7.06–7.43 (15H, br. m, OCH₂C₆<u>H₅</u>, NCH₂C₆<u>H₅</u> and CHC₆<u>H₅</u>).

EXAMPLE 27

9-N-(2-chloro-2-phenylethyl)-aminodeoxyclavulanic acid

Benzyl 9-N-(2-chloro-2-phenylethyl)-N-benzylaminodeoxyclavulanate is hydrogenolysed by the method described in Example 26 to yield the title compound.

Preparation 28

Benzyl 9-N-(2-carbamoylethyl)methallylaminodeoxyclavulanate

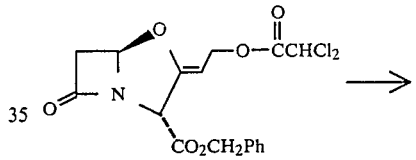

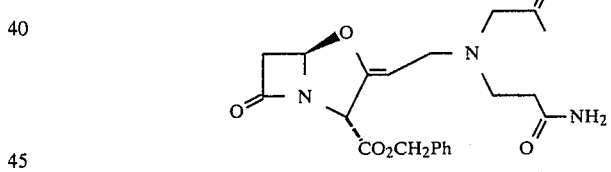

Benzyl dichloroacetylclavulanate (20 g; 0.05 mol) in dry dimethylformamide (200 ml) at −20° C. was treated dropwise with 2-carbamoylethylmethallylamine (14.2 g; 0.1 mol) in dry dimethylformamide (50 ml) over 25 min. After 1 hr the reaction was diluted with ethyl acetate and washed with brine (×5). The organic layer was then extracted with tartaric acid solution. This extract was immediately neutralized and back extracted into fresh ethyl acetate with saturated sodium hydrogen carbonate solution. The organic layer was separated, dried (MgSO₄) and evaporated to give the title ester in 43.6% yield.

ν_max. 1800, 1745 and 1677 cm⁻¹. δ (CDCl₃) 1.69 (3H, s, CH₃), 2.10–3.68 (10H, m, 5×CH₂), 4.61 (1H, br. t, J 7 Hz, 8—CH), 4.79 (2H, br. s, C:CH₂), 5.02 (1H, s, 3—CH), 5.13 (2H, s, CH₂Ph), 5.59 (1H, d, J 3 Hz, 5—CH), 6.20 (1H, br., NH₂ rotamer), 7.23 (5H, s, aromatics), 7.55 (1H, br, NH₂ rotamer).

EXAMPLE 28

9-N-(2-carbamoylethyl)aminodeoxyclavulanic acid

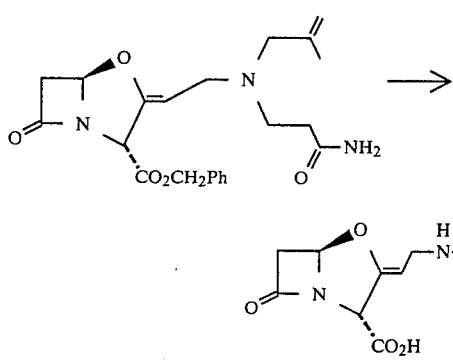

Benzyl 9-N-(2-carbamoylethyl)-methallylaminodeoxyclavulanate (8.5 g; 20.58 mmol) in ethanol (100 ml) was added to 10% Pd on carbon (2 g) in water (20 ml)/ethanol (30 ml) which had been prehydrogenated. The mixture was hydrogenated for 25 min by which time all starting material had been consumed (t.l.c.). The reaction was cooled in an ice-bath and then filtered. The filter cake was washed with distilled water, concentration of the aqueous washings under high vacuum caused the title acid to crystallise. Filtration gave pure product (2.1 g) in 38% yield.

$v_{max}$. (Nujol) 1803, 1799 sh, 1691 and 1611 cm$^{-1}$. δ (D$_2$O) 2.71 (2H, t, J 7 Hz, CH$_2$CONH$_2$), 2.99–3.44 (3H, m, NCH$_2$CH$_2$CONH$_2$ and 6β—CH), 3.59 (1H, dd, J 3 and 14 Hz, 6α—CH) partly obscured by 3.77 (2H, d, J 8 Hz, 9—CH$_2$), 4.82 (1H, br. t, J 8 Hz, 8—CH), 5.01 (1H, s, 3—CH) and 5.78 (1H, d, J 3 Hz, 5—CH).

Preparation 29a

N-(2-Phenylaminoethyl)methallylamine

N-2-Phenylaminoethylamine (12.5 g; 92 mmol) was treated with 2-methallylchloride (4.15 g; 4.5 cm$^3$) with vigorous stirring and gentle warming. An exothermic reaction occurred and once cool, diethyl ether was added and the resultant solid filtered off. The filtrate was evaporated and chromatographed on silica eluting with ethylacetate. Fractions were collected containing the title amine, and combined fractions were evaporated to afford an oil, 3.85 g (22%) δ (CDCl$_3$) 1.72 (3H, s, C(CH$_3$)), 2.72–2.95 (2H, m) and 3.05–3.22 (4H, m), NHCH$_2$CH$_2$N and NCH$_2$C(CH$_3$)), 4.84 (2H, bs, =CH$_2$), 6.50–6.80 (3H, m, N— 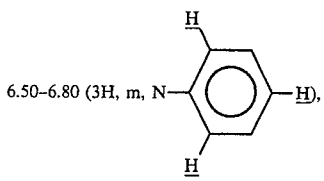 —H), 7.00–7.32 (2H, m, N— 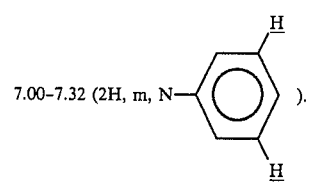 ).

Preparation 29b

Benzyl 9-N-(2-phenylaminoethyl)-2-methallyl aminodeoxyclavulanate

Benzyl dichloroacetylclavulanate (4.2 g; 10.5 mmol) in dry dimethylformamide (20 cm$^3$) at −20° was treated with 1.9 equivalents of N-(2-phenylaminoethyl)-2-methallylamine (3.78 g) in dimethylformamide (10 cm$^3$), dropwise over several minutes with vigorous stirring. The reaction was allowed to warm up to room temperature over 2 hours, then poured into ethylacetate (250 cm$^3$) and washed with water (5×100 cm$^3$) and saturated brine (5×150 cm$^3$), dried (anhydrous magnesium sulphate) and evaporated to an oil. This crude oil was chromatographed on silica, eluting with toluene-ethylacetate (10:1).

Fractions containing the title compound, Rf (SiO$_2$/toluene:ethylacetate; 7:1) ≃0.7 (detection by aqueous potassium permanganate spray). Combined fractions were evaporated to afford 800 mg (105%) of an oil. ν(film) 3360, 1800, 1745, 1690, 1600, 890, 750, 690 cm$^{-1}$.

EXAMPLE 29

9-N-(2-Phenylaminoethyl)aminodeoxyclavulanic acid

Benzyl 9-N-(2-phenylaminoethyl)-2-methallyl)amino deoxyclavulanate (400 mg; 0.87 mmol) in ethanol/tetrahydrofuran (10 cm$^3$; 1:3) was hydrogenolysed with 150 mg 10% palladium on carbon for 1¼ hours at atmospheric pressure. The catalyst was filtered off, washed with tetrahydrofuran and the filtrate evaporated, redissolved in ethanol/tetrahydrofuran (10 cm$^3$; 1:1) plus 2 drops water and hydrogenolysed with 150 mg fresh catalyst for 1¾ hours.

The catalyst was filtered off and the filtrate evaporated to an oil; this oil was chromatographed on silica eluting with ethylacetate-ethanol-water 8:4:2 grading to 5:4:2. Fractions containing the title compound were collected, Rf (SiO$_2$/ethylacetate-ethanol-water; 10:4:2)=0.5 (detection by potassium permanganate spray). Combined fractions were evaporated to afford the title compound as crystalline solid from methanol, yield=33 mg (12%) ν(Nujol) 3270, 1800, 1688, 1597 (broad), 1300, 1185, 1115, 1040, 1015, 1000, 922, 890, 752, 742, 690 cm$^{-1}$, ν(KBr) 3280, 1795, 1692, 1600, 1295, 1185, 1115, 1040, 1015, 890, 750, 694 cm$^{-1}$. δ (D$_2$O) 3.08 (1H, d, J 17 Hz, 6βCH), 3.23 (2H, t, J 6 Hz, $\overset{\oplus}{N}$H$_2$CH$_2$CH$_2$NH),

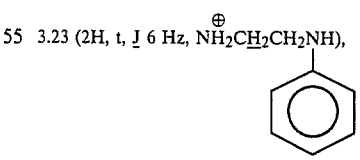

3.49 (2H, t, J 6 Hz, NCH$_2$CH$_2$NH),
  |
  C$_6$H$_5$ 3.55 (1H, dd, J 17 and 3 Hz, 6αCH), 3.74 and 3.81 (2H, dABq, J$_{AB}$ 12 Hz and J$_d$ 7.5 Hz, 9CH$_2$), 8CH partially obscured by HOD, 5.00 (1H, s, 3CH), 5.73 (1H, bd, J 3 Hz, 5αCH), 6.73–6.91 (3H, m, N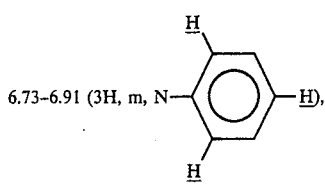, 7.20–7.35 (2H, m, N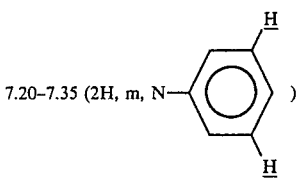)

Preparation 30a

N-(2-Hydroxy-2-phenylethyl)benzylamine

2-Amino-1-phenylethanol (20 g; 146 mmol) in ethanol (100 cm$^3$) was treated with 1 equivalent of baenzaldehyde (15 cm$^3$) and stirred. After several minutes the resultant imine began to crystallise out. After 1 hour this imine was filtered off cold and washed with cold ethanol. Drying afforded 29.6 g (90%) of the imine. This imine was dissolved in tetrahydrofuran (150 cm$^3$) and hydrogenated with 10 g of 10% palladium on carbon until hydrogen uptake ceased. The catalyst was filtered off and the solvent evaporated. Addition of cold ethanol afforded the title compound as a colourless crystalline solid, yield=18.5 g (56%) $\nu$(Nujol) 3270, 1180, 1100, 1060, 1030, 975, 970, 925, 921, 870, 850, 752, 698 cm$^{-1}$, $\delta$ (CDCl$_3$) 2.55–3.10 (4H, m, NC$\underline{H}_2$C$\underline{H}$OH, two protons exchange on deuteration), 3.72 (2H, s, NC$\underline{H}_2$C$_6$H$_5$), 4.56–4.82 (1H, m, CH$_2$C$\underline{H}$OH), 7.23 and 7.26 (10H, 2×s, 2×C$_6\underline{H}_5$).

Preparation 30b

Benzyl 9-N-(2-hydroxy-2-phenylethyl)-N-benzylaminodeoxyclavulanate

Benzyldichloroacetylclavulanate (10 g; 25 mmol) in dimethylformamide (50 cm$^3$) was treated at $-25°$ C. with 1.9 equivalents of N-(2-hydroxy-2-phenylethyl)-benzylamine in dimethylformamide (50 cm$^3$), dropwise over several minutes. The temperature was allowed to rise slowly to $+15°$ over 1½ hours, after which the mixture was poured into ethylacetate (250 cm$^3$) and washed with water (5×100 cm$^3$) and saturated brine (6×200 cm$^3$), dried (ahnhydrous magnesium sulphate) and evaporated to an oil. This oil was chromatographed on silica eluting with ethyl acetate-cyclohexane 1:2. Fractions were collected containing the title compound, Rf (SiO$_2$/toluene-ethylacetate; 7:1)=0.33 (detection by aqueous potassium permanganate spray). Combined fractions were evaporated to afford 6.1 g (49%) of the title compound. $\nu$(film) 3440 (broad), 1805, 1750, 1692, 740, 700 cm$^{-1}$, $\delta$ (CDCl$_3$) 2.38–2.65 (2H, m, NC$\underline{H}_2$CHOH), 2.92 and 2.95 (1H, 2×d, J 17 Hz, 6$\beta$C$\overline{\underline{H}}$), 3.26 (2H, d, J 7 Hz, 9C$\underline{H}_2$), 3.42 (1H, dd, J 17 and 3 Hz, 6$\alpha$CH only observed when 9CH$_2$ decoupled with 8CH), 3.15–3.85 (2H, bm, NC$\underline{H}_2$C$_6$H$_5$), 4.53–4.85 (2H, bm, CH$_2$C$\underline{H}$OH and 8C$\underline{H}$), 5.08 (1H, bs, 3C$\underline{H}$), 5.18 (2H, bs, OC$\underline{H}_2$C$_6$H$_5$), 5.62 (1H, d, J 3 Hz, 5$\alpha$C$\underline{H}$), 7.27 (15H, bs, 3×C$_6\underline{H}_5$).

Preparation 30c

9-N-(2-Hydroxy-2-phenylethyl)benzylaminodeoxyclavulanic acid

Benzyl 9-N-(2-hydroxy-2-phenylethyl)benzylamino deoxyclavulanate (5.4 g; 10.84 mmol) in tetrahydrofruan (80 cm$^3$) was hydrogenolysed at atmospheric pressure in the presence of 2 g 10% palladium on carbon for 1½ hours. The catalyst was filtered off and the mixture re-hydrogenated with fresh catalyst (2 g) for a further two hours. The catalyst was filtered off and washed with aqueous tetrahydrofuran. The filtrate was evaporated, re-dissolved in tetrahydrofuran and re-hydrogenated for five hours in the presence of fresh Pd/C (2 g). After eight hours total hydrogenation the catalyst was filtered off and washed with aqueous tetrahydrofuran, the filtrate was evaporated and the residue chromatographed on silica eluting with ethylacetate-ethanol-water (10:4:1). Fractions were collected containing material Rf (SiO$_2$/ethylacetate-ethanol-water (10:4:2))=0.66 (detection by potassium permanganate spray), combined fractions were evaporated to afford a foam from acetone, yield=1.15 g (26%). $\nu$(Nujol) 1790, 1700, 1615, 1305, 1195, 1120, 1060, 1040, 1020, 900, 745, 705 cm$^{-1}$; $\nu$(KBr) 1787, 1690, 1610, 1390, 1303, 1190, 1015, 895, 740, 697 cm$^{-1}$; $\delta$ (D$_2$O/DMSOd6) 2.83–3.15 (3H, m, C$\underline{H}_2$CHOH and 6$\beta$C$\underline{H}$), 3.48–3.53 (1H, m, 6$\alpha$C$\underline{H}$), 3.71 (2H, broad m, 9C$\underline{H}_2$), 4.05–4.25 (2H, m, NC$\underline{H}_2$C$_6$H$_5$), 4.85–5.04 (3H, m, 3C$\underline{H}$ and 8C$\underline{H}$ and C$\underline{H}$OH), 5.74 (1H, bs, 5$\alpha$C$\underline{H}$), 7.23–7.54 (10$\underline{H}$, m, 2×C$_6\underline{H}_5$).

EXAMPLE 30

9-N-(2-Hydroxy-2-phenylethyl)aminodeoxyclavulanic acid

Isolated from the above was a material Rf (SiO$_2$-/ethylacetate-ethanol-water; 10:4:2)=0.37 (detection by aqueous potassium permanganate spray). Combined fractions were evaporated to afford an off-white solid from acetonitrile, yield=320 mg (93%), spectral analysis showed this compound to be the secondary amin zwitterion. $\nu$(Nujol) 1790, 1695, 1620, 1305, 1192, 1120, 1095, 1065, 1040,1015, 745, 700 cm$^{-1}$, $\nu$(KBr)1785, 1690, 1610,1390, 1305, 1190, 1017, 750, 700 cm$^{-1}$. $\delta$ (D$_2$O/DMSOd6) [3.09 (d, J 17 Hz), 3.12 (d, J 17 Hz), 1H 6$\beta$C$\underline{H}$] 3.21–3.36 (2H, m, NC$\underline{H}_2$CHOH), 3.58 (1H, bd, J 17 Hz, 6$\alpha$C$\underline{H}$), 3.73–3.91 (2$\overline{\text{H}}$, m, 9 CH$_2$), 4.85 (1H, t, J 8 Hz, 8C$\underline{H}$ partially obscured by HO$\overline{\text{D}}$), 5.00 (1H, s, 3C$\underline{H}$), 4.96–5.09 (1H, m, CH$_2$C$\underline{H}$OH obscured partially by 3C$\underline{H}$), 5.79 (1H, bs, 5$\alpha$C$\underline{H}$), 7.35–7.56 (5H, m, C$_6$H$_5$).

The following Tables 1 and 2 show representative examples of the activities of the above described compounds.

TABLE 1

| Synergistic Activity of Compound with Amoxycillin | | | |
|---|---|---|---|
| Compound of Example No | Conc. of Compound $\mu$g/ml | MIC $\mu$g/ml S. aureus Russell | Amoxycillin E. coli JT39 |
| 1 | 5 | 0.16 | 8 |
|  | 1 | 1.25 | 16 |
| 2 | 5 | Inhib | 2(ampicillin) |
|  | 1 | 0.15(ampicillin) | 8(ampicillin) |
| 4 | 5 | <0.01 | 4 |
|  | 1 | 0.3 | 16 |
| 5 | 5 | Inhib | 2 |
|  | 1 | 0.3 | 4 |
| 12 | 5 | 0.16 | 4 |

TABLE 1-continued

| Synergistic Activity of Compound with Amoxycillin | | | |
|---|---|---|---|
| Compound of Example No | Conc. of Compound μg/ml | MIC μg/ml S. aureus Russell | Amoxycillin E. coli JT39 |
| 13 | 1 | 1.25 | 6 |
|    | 5 | (0.04) | 2 |
| 18 | 1 | 0.6 | 4 |
|    | 5 | Inhib | 4 |
| 19 | 1 | 0.3 | 8 |
|    | 5 | 0.16 | 4 |
| 20 | 1 | 1.25 | 8 |
|    | 5 | 0.08 | 2 |
| 21 | 1 | 0.6 | 8 |
|    | 5 | Inhib | (4.0) |
| 22 (2nd compound) | 1 | 0.16 | 8.0 |
|    | 5 | 0.04 | 4 |
|    | 1 | 0.3 | 8 |
| 23 | 5 | Inhib | 1 |
|    | 1 | 0.3 | 4 |
| 25 | 5 | Inhib | (4.0) |
|    | 1 | (0.62) | 8.0 |
| 26 | 5 | Inhib | (1.0) |
|    | 1 | Inhib | 4.0 |
| 29 | 5 | Inhib | 4 |
|    | 1 | Inhib | 8 |
| 30 | 5 | Inhib | 2 |
|    | 1 | 0.3 | 8 |

Inhib = Inhibitor by compound alone.
( ) = Inhibited in control well.

TABLE 2

| | Antibacterial Activity | |
|---|---|---|
| Compound of Example No | MIC (μg/ml) S.aureus Russell | E.coli JT39 |
| 1 | 8 | 16 |
| 2 | 8 | 31.2 |
| 4 | 4 | 31.2 |
| 5 | 8 | 31.2 |
| 12 | 8 | 31.2 |
| 13 | 16 | 31.2 |
| 18 | 8 | 31.2 |
| 19 | 16 | 31.2 |
| 20 | 16 | 31.2 |
| 21 | 4 | 8 |
| 22 (2nd compound) | 4 | 62.5 |
| 23 | 16 | 31.2 |
| 25 | 2 | 8 |
| 26 | ≦0.5 | 8 |
| 28 | 16 | 16 |
| 29 | 4 | 16 |
| 30 | 2 | 31.2 |

We claim:
1. A compound of the formula (I):

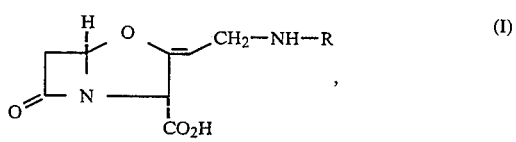

a pharmaceutically acceptable salt thereof or an in-vivo hydrolyzable ester thereof wherein R is alkyl of 2-12 carbon atoms or aralkyl of 2-6 carbon atoms in the alkyl moiety substituted on an alkyl carbon atom other than that adjacent to —NH— group, by 1-3 substituents selected from the group consisting of halo; non-aromatic heterocyclyl of 4-7 ring atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, said non-aromatic heterocyclyl being linked through carbon; an aromatic heterocyclyl of 4-7 ring atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; nitro; oxo; —$OR^1$; $SR^1$; —$P(O)R^2R^3$; —$NR^4R^5$; =$NR^6$; and —$S(O)_nR^S$ wherein n is one or two and $R^S$ is hydroxy, hydrocarbyloxy or heterocyclyl of 4-7 ring atoms unsubstituted or substituted by alkyl of 1-6 carbon atoms, a heterocyclyl of 4-7 ring atoms, amino, alkanoylamino of 1-6 carbon atoms in the alkyl moiety, mono-, di- or trialkylamino of 1-6 carbon atoms in each alkyl group, hydroxy, alkoxy of 1-6 carbon atoms, mercapto, alkylthio of 1-6 carbon atoms, heterocyclylthio of 4-7 ring atoms, arylthio, sulphamoyl, carbamoyl, amidino, guanidino, nitro, chloro, bromo, fluoro, carboxy or a salt or ester thereof, alkanoyloxy of 1-6 carbon atoms in the alkyl moiety, arylcarbonyl or heterocyclylcarbonyl of 4-7 ring atoms; or $R^S$ is —$NR^TR^U$ wherein $R^T$ and $R^U$ are each hydrogen or a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; or $R^T$ and $R^U$ together form the residue of a heterocyclic ring of 4-7 ring atoms; $R^1$ is hydrogen, a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, heterocyclyl of 4-7 ring members, —$COR^H$, $CO_2R^H$ or $CON(R^H)_2$ wherein $R^H$ is hydrogen, a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, or a heterocyclyl of 4-7 ring atoms, or two of said $R^1$ groups are joined to form a ring; $R^2$ and $R^3$ are each hydroxy, a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, or carbyloxy; $R^4$ is hydrogen or a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; $R^5$ is hydrogen, a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, a heterocyclyl of 4-7 ring atoms, —$COR^H$, $CO_2R^H$ or $CON(R^H)_2$ wherein $R^H$ is hydrogen, a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, or heterocyclyl of 4-7 ring atoms, or —$S(O)_nR^S$ wherein n and $R^S$ are as above defined; and $R^6$ is hydroxy, a hydrocarbon of up to 18 carbon atoms unsubstituted or substituted by up to 3 substituents selected from the group consisting of halo, alkyl, of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, hydrocarbyloxy, amino, arylamino or —$NHCONH_2$; provided that a carbon atom of the group R which carries an oxo substituent does not carry a second substituent other than a group —$NR^4R^5$.

2. A compound according to claim 1 wherein when R is a substituted alkyl moiety, the alkyl moiety contains 2-6 carbon atoms and when R is a substituted aralkyl moiety, the aryl moiety is phenyl.

3. A compound according to claim 1 wherein the hydrocarbon groups contain up to 10 carbon atoms.

4. A compound according to claim 1 wherein the hydrocarbon groups contain up to 6 carbon atoms.

5. A compound according to claim 1 wherein R is a substituted alkyl moiety wherein the alkyl moiety is ethyl.

6. A compound according to claim 1 wherein R is alkyl of 2-6 carbon atoms or aralkyl of 2-6 carbon atoms in the alkyl moiety substituted by —$OR^1$ wherein $OR^1$ is alkoxy of 1-6 carbon atoms, alkanoyloxy of 1-6 carbon atoms in the alkyl moiety or a moiety of the formula (A):

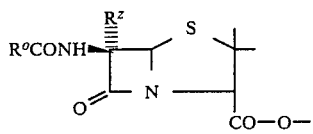

(A)

wherein $R^oCONH$ is an organic acylamino moiety of an antibacterialy active penicillin and $R^z$ is hydrogen or methoxy.

7. A compound according to claim 1 wherein R is alkyl of 2-6 carbon atoms substituted by $NR^4R^5$ wherein $NR^4R^5$ is amino, alkoxycarbonylamino of 1-6 carbon atoms in the alkoxy moiety, alkylsulphoylamido of 1-6 carbon atoms in the alkyl moiety or alkylureidoamino of 1-6 carbon atoms in the alkyl moiety.

8. A compound according to claim 1 wherein R is alkyl of 2-6 carbon atoms substituted by —$S(O)_nR^S$ wherein n is one or two and $R^S$ is hydroxy, hydrocarbyloxy or heterocyclyl moiety or 4-7 ring atoms unsubstituted or substituted by alkyl of 1-6 carbon atoms, a heterocyclyl of 4-7 ring atoms, amino, alkanoylamino of 1-6 carbon atoms in the alkyl moiety, mono-, di- or trialkylamino of 1-6 carbon atoms in each alkyl group, hydroxy, alkoxy of 1-6 carbon atoms, mercapto, alkylthio of 1-6 carbon atoms, heterocyclylthio of 4-7 ring atoms, arylthio, sulphamoyl, carbamoyl, amidino, guanidino, nitro, chloro, bromo, fluoro, carboxy or a salt or ester thereof, alkanoyloxy of 1-6 carbon atoms in the alkyl moiety, arylcarbonyl or heterocyclylcarbonyl of 4-7 ring atoms; or $R^S$ is —$NR^TR^U$ wherein $R^T$ and $R^U$ are each hydrogen or a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; or $R^T$ and $R^U$ together form the residue of a heterocyclic ring of 4-7 ring atoms.

9. The compound according to claim 1 which is:
9-N-(2,2-dimethoxyethyl)aminodeoxyclavulanic acid;
9-N-(2-chloroethyl)aminodeoxyclavulanic acid;
9-N-[2(N-methoxycarbonylamino)ethyl]amino-9-deoxyclavulanic acid;
9-N-(2-pyrid-2'-ylethyl)aminodeoxyclavulanic acid;
9-N-(2-pyrid-4'-ylethyl)aminodeoxyclavulanic acid;
9-N(2-methoxyethyl)aminodeoxyclavulanic acid;
9-N-[(N'-benzyl-N'-methylsulphonamido)ethyl-]aminodeoxyclavulanic acid;
9-N-(2-diethyloxyphosphorylethyl)aminodeoxyclavulanic acid;
9-N-[4-(sulphonato)butyl]aminodeoxyclavulanic acid;
9-N(2-phenylthioethyl)aminodeoxyclavulanic acid;
9-N-2[(N,N-dimethylsulphamoyl)benzylamino]ethylaminodeoxyclavulanic acid;
9-N-(2-methylsulphonamidoethyl)aminodeoxyclavulanic acid;
9-N-(3-methylsulphonamidopropyl)aminodeoxyclavulanic acid;
9-N-[2-(N-methyl)methylsulphonamidoethyl]aminodeoxy-clavulanic acid;
9-N-[2-[6β-(DL-2-Phenoxycarbonyl-2-thien-3'-ylacetamido)penicillanoyloxy]ethyl]aminodeoxyclavulanic acid;
9-N-[2-[6β-(DL-2-Phenoxycarbonyl-2-thien-3-ylacetamido)penicillanoyloxy]ethyl]aminodeoxyclavulanic acid;
9-N-[2-[6β-(DL-2-Phenoxycarbonyl-2-thien-3'-ylacetamido)penicillanoyloxy]ethyl]-N-(2-methallyl-)aminodeoxyclavulanic acid;
9-N-[3-Imidazol-1-yl)propyl]aminodeoxyclavulanic acid;
9-N-(4,4-Diethoxybutyl)aminodeoxyclavulanic acid;
9-N-(4-Acetoxybutyl)aminodeoxyclavulanic acid;
9-N-[4-Methyl-4-nitropentyl]aminodeoxyclavulanic acid;
9-[N-benzyl-N-(N',N'-dimethylureido)ethyl-]aminodeoxyclavulanic acid and 9-N-(N',N'-dimethylureido)ethylaminodeoxyclavulanic acid;

9-N-[2-(phenylsulphonyl)ethyl]aminodeoxyclavulanic acid;
9-N-(3-N-benzylcarbamoylprop-1-yl)aminodeoxyclavulanic acid;
9-N-(3-N-Benzylcarbamoyleth-1-yl)aminodeoxyclavulanic acid;
9-N-(2-Indol-3'-ylethyl)aminodeoxyclavulanic acid;
9-N-(2-chloro-2-phenylethyl)-aminodeoxyclavulanic acid; or
9-N-(2-carbamoylethyl)aminodeoxyclavulanic acid.

10. A process for the production of a compound of claim 1 which comprises either:

(a) removing a group $R^x$ from a compound of the formula (II):

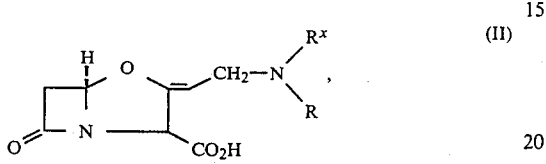

a salt or ester thereof wherein R is alkyl of 2-12 carbon atoms or aralkyl of 2-6 carbon atoms in the alkyl moiety substituted on an alkyl carbon atom other than that adjacent to —NH— group, by 1-3 substituents selected from the group consisting of halo; non-aromatic heterocyclyl of 4-7 ring atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, said non-aromatic heterocyclyl being linked through carbon; an aromatic heterocyclyl of 4-7 ring atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; nitro; oxo; —$OR^1$; $SR^1$; —$P(O)R^2R^3$; —$NR^4R^5$; =$NR^6$; and —$S(O)_nR^S$ wherein n is one or two and $R^S$ is hydroxy, hydrocarbyloxy or heterocyclyl of 4-7 ring atoms unsubstituted or substituted by alkyl of 1-6 carbon atoms, a heterocyclyl of 4-7 ring atoms, amino, alkanoylamino of 1-6 carbon atoms in the alkyl moiety, mono-, di- or trialkylamino of 1-6 carbon atoms in each alkyl group, hydroxy, alkoxy of 1-6 carbon atoms, mercapto, alkylthio of 1-6 carbon atoms, heterocyclylthio of 4-7 ring atoms, arylthio, sulphamoyl, carbamoyl, amidino, guanidino, nitro, chloro, bromo, fluoro, carboxy or a salt or ester thereof, alkanoyloxy of 1-6 carbon atoms in the alkyl moiety, arylcarbonyl or heterocyclylcarbonyl of 4-7 ring atoms; or $R^S$ is —$NR^TR^U$ wherein $R^T$ and $R^U$ are each hydrogen or a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; or $R^T$ and $R^U$ together form the residue of a heterocyclic ring of 4-7 ring atoms; $R^1$ is hydrogen, a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, heterocyclyl of 4-7 ring members, —$COR^H$, $CO_2R^H$ or $CON(R^H)_2$ wherein $R^H$ is hydrogen, a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, or a heterocyclyl of 4-7 ring atoms, or two of said $R^1$ groups are joined to form a ring; $R^2$ and $R^3$ are each hydroxy, a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, or carbyloxy; $R^4$ is hydrogen or a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; $R^5$ is hydrogen, a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, a heterocyclyl of 4-7 ring atoms, —$COR^H$, $CO_2R^H$ or $CON(R^H)_2$ wherein $R^H$ is hydrogen, a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, or heterocyclyl of 4-7 ring atoms, or —$S(O)_nR^S$ wherein n and $R^S$ are as above defined; and $R^6$ is hydroxy, a hydrocarbon of up to 18 carbon atoms unsubstituted or substituted by up to 3 substituents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxy, hydrocarbyloxy, amino, arylamino or —NHCONH$_2$; provided that a carbon atom of the group R which carries an oxo substituent does not carry a second substituent other than a group —NR$^4$R$^5$; and R$^x$ is a removal protecting group; or (b) reacting a compound of the formula (III):

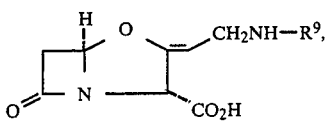

a salt or ester thereof wherein R$^9$ is hydrogen or an amino protecting group; with a compound of the formula R—Z; wherein R is as above defined and Z is a readily displaceable group, removing any group R$^9$ that is not hydrogen; and optionally thereafter converting the compound produced to a salt or ester as desired.

11. A pharmaceutical composition useful for effecting beta-lactamase inhibition in humans and animals and for treating bacterial infections in humans and animals which comprises a therapeutically effective amount of a compound of the formula (I):

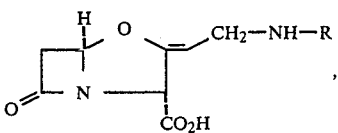

a pharmaceutically acceptable salt thereof or an in-vivo hydrolyzable ester thereof wherein R is alkyl of 2–12 carbon atoms or aralkyl of 2–6 carbon atoms in the alkyl moiety substituted on an alkyl carbon atom other than that adjacent to —NH— group, by 1–3 substituents selected from the group consisting of halo; non-aromatic heterocyclyl of 4–7 ring atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, said non-aromatic heterocyclyl being linked through carbon; an aromatic heterocyclyl of 4–7 ring atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo; nitro; oxo; —OR$^1$; SR$^1$; —P(O)R$^2$R$^3$; —NR$^4$R$^5$; =NR$^6$; and —S(O)$_n$R$^S$ wherein n is one or two and R$^S$ is hydroxy, hydrocarbyloxy or heterocyclyl of 4–7 ring atoms unsubstituted or substituted by alkyl of 1–6 carbon atoms, a heterocyclyl of 4–7 ring atoms, amino, alkanoylamino of 1–6 carbon atoms in the alkyl moiety, mono-, di- or trialkylamino of 1–6 carbon atoms in each alkyl group, hydroxy, alkoxy of 1–6 carbon atoms, mercapto, alkylthio of 1–6 carbon atoms, heterocyclylthio of 4–7 ring atoms, arylthio, sulphamoyl, carbamoyl, amidino, guanidino, nitro, chloro, bromo, fluoro, carboxy or a salt or ester thereof, alkanoyloxy of 1–6 carbon atoms in the alkyl moiety, arylcarbonyl or heterocyclylcarbonyl of 4–7 ring atoms; or R$^S$ is —NR$^T$R$^U$ wherein R$^T$ and R$^U$ are each hydrogen or a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo; or R$^T$ and R$^U$ together form the residue of a heterocyclic ring of 4–7 ring atoms; R$^1$ is hydrogen, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, heterocyclyl of 4–7 ring members, —COR$^H$, CO$_2$R$^H$ or CON(R$^H$)$_2$ wherein R$^H$ is hydrogen, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, or a heterocyclyl of 4–7 ring atoms, or two of said R$^1$ groups are joined to form a ring; R$^2$ and R$^3$ are each hydroxy, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, or carbyloxy; R$^4$ is hydrogen or a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo; R$^5$ is hydrogen, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, a heterocyclyl of 4–7 ring atoms, —COR$^H$, CO$_2$R$^H$ or CON(R$^H$)$_2$ wherein R$^H$ is hydrogen, a hydrocarbon of up to 18 carbon atoms unsubstituted or substituted by up to 3 substitutents selected from the group consisting of halo, alkyl of 1–6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, or heterocyclyl of 4-7 ring atoms, or $-S(O)_nR^S$ wherein n and $R^S$ are as above defined; and $R^6$ is hydroxy, a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, hydrocarbyloxy, amino, arylamino or $-NHCONH_2$; provided that a carbon atom of the group R which carries an oxo substituent does not carry a second substituent other than a group $-NR^4R^5$, in combination with a pharmaceutically acceptable carrier.

12. A composition according to claim 11 wherein when R is a substituted alkyl moiety, the alkyl moiety contains 2-6 carbon atoms and when R is a substituted aralkyl moiety, the aryl moiety is phenyl.

13. A composition according to claim 11 wherein the hydrocarbon groups contain up to 10 carbon atoms.

14. A composition according to claim 11 wherein the hydrocarbon groups contain up to 6 carbon atoms.

15. A composition according to claim 11 wherein R is a substituted alkyl moiety wherein the alkyl moiety is ethyl.

16. A composition according to claim 11 wherein R is alkyl of 2-6 carbon atoms or aralkyl of 2-6 carbon atoms in the alkyl moiety substituted by $-OR^1$ wherein $OR^1$ is alkoxy of 1-6 carbon atoms, alkanoyloxy of 1-6 carbon atoms in the alkyl moiety or a moiety of the formula (A):

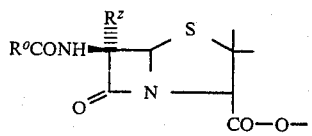

wherein $R^oCONH$ is an organic acylamino moiety of an antibacterialy active penicillin and $R^z$ is hydrogen or methoxy.

17. A composition according to claim 11 wherein R is alkyl of 2-6 carbon atoms substituted by $NR^4R^5$ wherein $NR^4R^5$ is amino, alkoxycarbonylamino of 1-6 carbon atoms in the alkoxy moiety, alkylsulphoylamido of 1-6 carbon atoms in the alkyl moiety or alkylureidoamino of 1-6 carbon atoms in the alkyl moiety.

18. A composition according to claim 11 wherein R is alkyl of 2-6 carbon atoms substituted by $-S(O)_nR^S$ wherein n is one or two and $R^S$ is hydroxy, hydrocarbyloxy or heterocyclyl moiety or 4-7 ring atoms unsubstituted or substituted by alkyl of 1-6 carbon atoms, a heterocyclyl of 4-7 ring atoms, amino, alkanoylamino of 1-6 carbon atoms in the alkyl moiety, mono-, di- or trialkylamino of 1-6 carbon atoms in each alkyl group, hydroxy, alkoxy of 1-6 carbon atoms, mercapto, alkylthio of 1-6 carbon atoms, heterocyclylthio of 4-7 ring atoms, arylthio, sulphamoyl, carbamoyl, amidino, guanidino, nitro, chloro, bromo, fluoro, carboxy or a salt or ester thereof, alkanoyloxy of 1-6 carbon atoms in the alkyl moiety, arylcarbonyl or heterocyclylcarbonyl of 4-7 ring atoms; or $R^S$ is $-NR^TR^U$ wherein $R^T$ and $R^U$ are each hydrogen or a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; or $R^T$ and $R^U$ together form the residue of a heterocyclic ring of 4-7 ring atoms.

19. The composition according to claim 11 wherein the compound is:

9-N-(2,2-dimethoxyethyl)aminodeoxyclavulanic acid;
9-N-(2-chloroethyl)aminodeoxyclavulanic acid;
9-N-[2(N-methoxycarbonylamino)ethyl]amino-9-deoxyclavulanic acid;
9-N-(2-pyrid-2'-ylethyl)aminodeoxyclavulanic acid;
9-N-(2-pyrid-4'-ylethyl)aminodeoxyclavulanic acid;
9-N-(2-methoxyethyl)aminodeoxyclavulanic acid;
9-N-[(N'-benzyl-N'-methylsulphonamido)ethyl]aminodeoxyclavulanic acid;
9-N-(2-diethyloxyphosphorylethyl)aminodeoxyclavulanic acid;
9-N-[4-(sulphonato)butyl]aminodeoxyclavulanic acid;
9-N(2-phenylthioethyl)aminodeoxyclavulanic acid;
9-N-2[(N,N-dimethylsulphamoyl)benzylamino]ethylaminodeoxyclavulanic acid;
9-N-(2-methylsulphonamidoethyl)aminodeoxyclavulanic acid;
9-N-(3-methylsulphonamidopropyl)aminodeoxyclavulanic acid;
9-N-[2-(N-methyl)methylsulphonamidoethyl]aminodeoxy-clavulanic acid;
9-N-[2-[6β-(DL-2-Phenoxycarbonyl-2-thien-3'-ylacetamido)penicillanoyloxy]ethyl]aminodeoxyclavulanic acid;
9-N-[2-[6β-(DL-2-Phenoxycarbonyl-2-thien-3-ylacetamido)penicillanoyloxy]ethyl]aminodeoxyclavulanic acid;
9-N-[2-[6β-(DL-2-Phenoxycarbonyl-2-thien-3'-ylacetamido)penicillanoyloxy]ethyl]-N-(2-methallyl)aminodeoxyclavulanic acid;
9-N-[3-Imidazol-1-yl)propyl]aminodeoxyclavulanic acid;
9-N-(4,4-Diethoxybutyl)aminodeoxyclavulanic acid;
9-N-(4-Acetoxybutyl)aminodeoxyclavulanic acid;
9-N-[4-Methyl-4-nitropentyl]aminodeoxyclavulanic acid;
9-[N-benzyl-N-(N',N'-dimethylureido)ethyl]aminodeoxyclavulanic acid and 9-N-(N',N'-dimethylureido)ethylaminodeoxyclavulanic acid;
9-N-[2-(phenylsulphonyl)ethyl]aminodeoxyclavulanic acid;
9-N-(3-N-benzylcarbamoylprop-1-yl)aminodeoxyclavulanic acid;
9-N-(3-N-Benzylcarbamoyleth-1-yl)aminodeoxyclavulanic acid;
9-N-(2-Indol-3'-ylethyl)aminodeoxyclavulanic acid;
9-N-(2-chloro-2-phenylethyl)-aminodeoxyclavulanic acid; or
9-N-(2-carbamoylethyl)aminodeoxyclavulanic acid.

20. A method of inhibiting beta-lactamase activity and treating bacterial infections in humans and animals which comprises administering to a human or animal in need thereof a therapeutically effective amount of a compound of the formula (I):

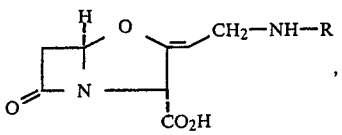

a pharmaceutically acceptable salt thereof or an in-vivo hydrolyzable ester thereof wherein R is alkyl of 2-12 carbon atoms or aralkyl of 2-6 carbon atoms in the alkyl moiety substituted on an alkyl carbon atom other than that adjacent to —NH— group, by 1-3 substituents selected from the group consisting of halo, non-aromatic heterocyclyl of 4-7 ring atoms unsubstituted or substituted by up to 3 substitutents selected from the group consisting of halo; alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, said non-aromatic heterocyclyl being linked through carbon; an aromatic heterocyclyl of 4-7 ring atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; nitro; oxo; —$OR^1$; $SR^1$; —$P(O)R^2R^3$; —$NR^4R^5$; =$NR^6$; and —$S(O)_nR^S$ wherein n is one or two and $R^S$ is hydroxy, hydrocarbyloxy or heterocyclyl of 4-7 ring atoms unsubstituted or substituted by alkyl of 1-6 carbon atoms, a heterocyclyl of 4-7 ring atoms, amino, alkanoylamino of 1-6 carbon atoms in the alkyl moiety, mono-, di- or trialkylamino of 1-6 carbon atoms in each alkyl group, hydroxy, alkoxy of 1-6 carbon atoms, mercapto, alkylthio of 1-6 carbon atoms, heterocyclylthio of 4-7 ring atoms, arylthio, sulphamoyl, carbamoyl, amidino, guanidino, nitro, chloro, bromo, fluoro, carboxy or a salt or ester thereof, alkanoyloxy of 1-6 carbon atoms in the alkyl moiety, arylcarbonyl or heterocyclylcarbonyl of 4-7 ring atoms; or $R^S$ is —$NR^TR^U$ wherein $R^T$ and $R^U$ are each hydrogen or a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; or $R^T$ and $R^U$ together form the residue of a heterocyclic ring of 4-7 ring atoms; $R^1$ is hydrogen, a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, heterocyclyl of 4-7 ring members, —$COR^H$, $CO_2R^H$ or $CON(R^H)_2$ wherein $R^H$ is hydrogen, a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, or a heterocyclyl of 4-7 ring atoms, or two of said $R^1$ groups are joined to form a ring; $R^2$ and $R^3$ are each hydroxy, a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, or carbyloxy; $R^4$ is hydrogen or a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; $R^5$ is hydrogen, a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, a heterocyclyl of 4-7 ring atoms, —$COR^H$, $CO_2R^H$ or $CON(R^H)_2$ wherein $R^H$ is hydrogen, a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, or heterocyclyl of 4-7 ring atoms, or —$S(O)_nR^S$ wherein n and $R^S$ are as above defined; and $R^6$ is hydroxy, a hydrocarbon of up to 18 carbon atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxy, hydrocarbyloxy, amino, arylamino or —$NHCONH_2$; provided that a carbon atom of the group R which carries an oxo substituent does not carry a second substituent other than a group —$NR^4R^5$, in combination with a pharmaceutically acceptable carrier.

21. A method according to claim 20 wherein when R is a substituted alkyl moiety, the alkyl moiety contains 2-6 carbon atoms and when R is a substituted aralkyl moiety, the aryl moiety is phenyl.

22. A method according to claim 20 wherein the hydrocarbon groups contain up to 10 carbon atoms.

23. A method according to claim 20 wherein the hydrocarbon groups contain up to 6 carbon atoms.

24. A method according to claim 20 wherein R is a substituted alkyl moiety wherein the alkyl moiety is ethyl.

25. A method according to claim 20 wherein R is alkyl of 2–6 carbon atoms or aralkyl of 2–6 carbon atoms in the alkyl moiety substituted by —OR$^1$ wherein OR$^1$ is alkoxy of 1–6 carbon atoms, alkanoyloxy of 1–6 carbon atoms in the alkyl moiety or a moiety of the formula (A):

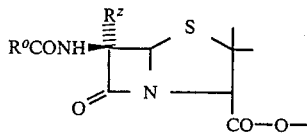

(A)

wherein R$^o$CONH is an organic acylamino moiety of an antibacterially active penicillin and R$^z$ is hydrogen or methoxy.

26. A method according to claim 20 wherein R is alkyl of 2–6 carbon atoms substituted by NR$^4$R$^5$ wherein NR$^4$R$^5$ is amino, alkoxycarbonylamino of 1–6 carbon atoms in the alkoxy moiety, alkylsulphoylamido of 1–6 carbon atoms in the alkyl moiety or alkylureidoamino of 1–6 carbon atoms in the alkyl moiety.

27. A method according to claim 20 wherein R is alkyl of 2–6 carbon atoms substituted by —S(O)$_n$R$^S$ wherein n is one or two and R$^S$ is hydroxy, hydrocarbyloxy or heterocyclyl moiety or 4–7 ring atoms unsubstituted or substituted by alkyl of 1–6 carbon atoms, a heterocyclyl of 4–7 ring atoms, amino, alkanoylamino of 1–6 carbon atoms in the alkyl moiety, mono-, di- or trialkylamino or 1–6 carbon atoms in each alkyl group, hydroxy, alkoxy of 1–6 carbon atoms, mercapto, alkylthio of 1–6 carbon atoms, heterocyclylthio of 4–7 ring atoms, arylthio, sulphamoyl, carbamoyl, amidino, guanidino, nitro, chloro, bromo, fluoro, carboxy or a salt or ester thereof, alkanoyloxy of 1∝6 carbon atoms in the alkyl moiety, arylcarbonyl or heterocyclylcarbonyl of 4–7 ring atoms; or R$^S$ is —NR$^T$R$^U$ wherein R$^T$ and R$^U$ are each hydrogen or a hydrocarbon of up to 18 carbon atoms unsubstituted or substituted by up to 3 substituents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo; or R$^T$ and R$^U$ together form the residue of a heterocyclic ring of 4–7 ring atoms.

28. A method according to claim 20 wherein the compound is:
9-N-(2,2-dimethoxyethyl)aminodeoxyclavulanic acid;
9-N-(2-chloroethyl)aminodeoxyclavulanic acid;
9-N-[2(N-methoxycarbonylamimo)ethy]amino-9-deoxyclavulanic acid;
9-N-(2-pyrid-2'-ylethyl)aminodeoxyclavulanic acid;
9-N-(2-pyrid-4'-ylethyl)aminodeoxyclavulanic acid;
9-N(2-methoxyethyl)aminodeoxyclavulanic acid;
9-N-[(N'-benzyl-N'-methylsulphonamido)ethyl-]aminodeoxyclavulanic acid;
9-N-(2-diethyloxyphorphosylethyl)aminodeoxyclavulanic acid;
9-N-[4-(sulphonato)butyl]aminodeoxyclavulanic acid;
9-N(2-phenylthioethyl)aminodeoxyclavulanic acid;
9-N-2[(N,N-dimethylsulphamoyl)benzylamino]ethylaminodeoxyclavulanic acid;
9-N-(2-methylsulphonamidoethyl)aminodeoxyclavulanic acid;
9-N-(3-methylsulphonamidopropyl)aminodeoxyclavulanic acid;
9-N-[2-(N-methyl)methylsulphonamidoethyl]aminodeoxy-clavulanic acid;
9-N-[2-[6β-(DL-2-Phenoxycarbonyl-2-thien-3'-ylacetamido)penicillanoyloxy]ethyl]aminodeoxyclavulanic acid;
9-N-[2-[6β-(DL-2-Phenoxycarbonyl-2-thien-3-ylacetamido)penicillanoyloxy]ethyl]aminodeoxyclavulanic acid;
9-N-[2-[6β-(DL-2-Phenoxycarbonyl-2-thien-3'-ylacetamido)penicillanoyloxy]ethyl]-N-(2-methallyl-)aminodeoxyclavulanic acid;
9-N-[3-Imidazol-1-yl)propyl]aminodeoxyclavulanic acid;
9-N-(4,4-Diethoxybutyl)aminodeoxyclavulanic acid;
9-N-(4-Acetoxybutyl)aminodeoxyclavulanic acid;
9-N-[4-Methyl-4-nitropentyl]aminodeoxyclavulanic acid;
9-[N-benzyl-N-(N'N'-dimethylureido)ethyl]aminodeoxyclavulanic acid and 9-N-(N'N'-dimethylureido)ethylaminodeoxyclavulanic acid;
9-N-[2-(phenylsulphonyl)ethyl]aminodeoxyclavulanic acid;
9-N-(3-N-benzylcarbamoylprop-1-yl)aminodeoxyclavulanic acid;
9-N-(3-N-Benzylcarbamoyleth-1-yl)aminodeoxyclavulanic acid;
9-N-(2-Indol-3'-ylethyl)aminodeoxyclavulanic acid;
9-N-(2-chloro-2-phenylethyl)-aminodeoxyclavulanic acid; or
9-N-(2-carbamoylethyl)aminodeoxyclavulanic acid.

29. A pharmaceutical composition useful for treating bacterial infections in humans and animals which comprises a synergistically effective amount of a compound of the formula (I):

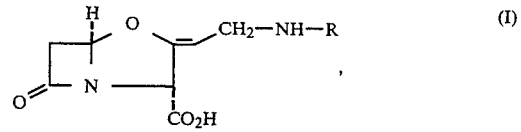

(I)

a pharmaceutically acceptable salt thereof or an in-vivo hydrolyzable ester thereof wherein R is alkyl of 2–12 carbon atoms or aralkyl of 2–6 carbon atoms in the alkyl moiety substituted on an alkyl carbon atom other than that adjacent to —NH— group, by 1–3 substituents selected from the group consisting of halo, non-aromatic heterocyclyl of 4–7 ring atoms unsubstituted or substituted by up to 3 substituents selected from the group consisting of halo; alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, said non-aromatic heterocyclyl being linked through carbon; an aromatic heterocyclyl of 4–7 ring atoms unsubstituted or substituted by up to 3 substituents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo; nitro; oxo; —OR$^1$; SR$^1$; —P(O)R$^2$R$^3$; —NR$^4$R$^5$;

=NR⁶; and —S(O)ₙRˢ wherein n is one or two and Rˢ is hydroxy, hydrocarbyloxy or heterocyclyl of 4–7 ring atoms unsubstituted or substituted by alkyl of 1–6 carbon atoms, a heterocyclyl of 4–7 ring atoms, amino, alkanoylamino of 1–6 carbon atoms in the alkyl moiety, mono-, di- or trialkylamino of 1–6 carbon atoms in each alkyl group, hydroxy, alkoxy of 1–6 carbon atoms, mercapto, alkylthio of 1–6 carbon atoms, heterocyclylthio of 4–7 ring atoms, arylthio, sulphamoyl, carbamoyl, amidino, guanidino, nitro, chloro, bromo, fluoro, carboxy or a salt or ester thereof, alkanoyloxy of 1–6 carbon atoms in the alkyl moiety, arylcarbonyl or heterocyclylcarbonyl of 4–7 ring atoms; or Rˢ is —NRᵀRᵁ wherein Rᵀ and Rᵁ are each hydrogen or a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo; or Rᵀ and Rᵁ together form the residue of a heterocyclic ring of 4–7 ring atoms; R¹ is hydrogen, a hydrocarbon of up to 18 carbon atoms unsubstituted or substituted by up to 3 substituents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, heterocyclyl of 4–7 ring members, —CORᴴ, CO₂Rᴴ or CON(Rᴴ)₂ wherein Rᴴ is hydrogen, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, or a heterocyclyl of 4–7 ring atoms, or two of said R¹ groups are joined to form a ring; R² and R³ are each hydroxy, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, or carbyloxy; R⁴ is hydrogen or a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo; R⁵ is hydrogen, a hydrocarbon of up to 18 carbon atoms unsubstituted or substituted by up to 3 substituents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, a heterocyclyl of 4–7 ring atoms, —CORᴴ, CO₂Rᴴ or CON(Rᴴ)₂ wherein Rᴴ is hydrogen, a hydrocarbon of up to 18 carbon atoms unsubstituted or substituted by up to 3 substituents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, or heterocyclyl of 4–7 ring atoms, or —S(O)ₙRˢ wherein n and Rˢ are as above defined; and R⁶ is hydroxy, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, hydrocarbyloxy, amino, arylamino or —NHCONH₂; provided that a carbon atom of the group R which carries an oxo substituent does not carry a second substituent other than a group —NR⁴R⁵ and an antibacterially effective amount of a penicillin or cephalosporin, in combination with a pharmaceutically acceptable carrier.

30. A composition according to claim 29 wherein when R is a substituted alkyl moiety, the alkyl moiety contains 2–6 carbon atoms and when R is a substituted aralkyl moiety, the aryl moiety is phenyl.

31. A composition according to claim 29 wherein the hydrocarbon groups contain up to 10 carbon atoms.

32. A composition according to claim 29 wherein the hydrocarbon groups contain up to 6 carbon atoms.

33. A composition according to claim 29 wherein R is a substituted alkyl moiety wherein the alkyl moiety is ethyl.

34. A composition according to claim 29 wherein R is alkyl of 2–6 carbon atoms or aralkyl of 2–6 carbon atoms in the alkyl moiety substituted by —OR¹ wherein OR¹ is alkoxy of 1–6 carbon atoms, alkanoyloxy of 1–6 carbon atoms in the alkyl moiety or a moiety of the formula (A):

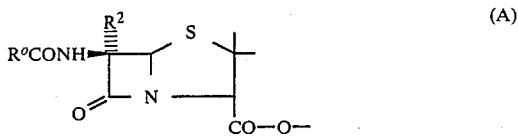

wherein RᵒCONH is an organic acylamino moiety of an antibacterially active penicillin and Rᶻ is hydrogen or methoxy.

35. A composition according to claim 29 wherein R is alkyl of 2–6 carbon atoms substituted by NR⁴R⁵ wherein NR⁴R⁵ is amino, alkoxycarbonylamino of 1–6 carbon atoms in the alkoxy moiety, alkylsulphoylamido of 1–6 carbon atoms in the alkyl moiety or alkylureidoamino of 1–6 carbon atoms in the alkyl moiety.

36. A composition according to claim 29 wherein R is alkyl of 2–6 carbon atoms substituted by —S(O)ₙRˢ wherein n is one or two and Rˢ is hydroxy, hydrocarbyloxy or heterocyclyl moiety or 4–7 ring atoms unsubstituted or substituted by alkyl of 1–6 carbon atoms, a heterocyclyl of 4–7 ring atoms, amino, alkanoylamino of 1–6 carbon atoms in the alkyl moiety, mono-, di- or trialkylamino of 1-6 carbon atoms in each alkyl group, hydroxy, alkoxy of 1-6 carbon atoms, mercapto, alkylthio of 1-6 carbon atoms, heterocyclylthio of 4-7 ring atoms, arylthio, sulphamoyl, carbamoyl, amidino, guanidino, nitro, chloro, bromo, fluoro, carboxy or a salt or ester thereof, alkanoyloxy of 1-6 carbon atoms in the alkyl moiety, arylcarbonyl or heterocyclylcarbonyl of 4-7 ring atoms; or $R^S$ is —$NR^TR^U$ wherein $R^T$ and $R^U$ are each hydrogen or a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; or $R^T$ and $R^U$ together form the residue of a heterocyclic ring of 4-7 ring atoms.

37. A composition according to claim 29 wherein the compound is:
9-N-(2,2-dimethoxyethyl)aminodeoxyclavulanic acid;
9-N-(2-chloroethyl)aminodeoxyclavulanic acid;
9-N-[2-(N-methoxycarbonylamino)ethyl]amino-9-deoxyclavulanic acid;
9-N-(2-pyrid-2'-ylethyl)aminodeoxyclavulanic acid;
9-N-(2-pyrid-4'-ylethyl)aminodeoxyclavulanic acid;
9-N(2-methoxyethyl)aminodeoxyclavulanic acid;
9-N-[(N'-benzyl-N'-methylsulphonamido)ethyl-]aminodeoxyclavulanic acid;
9-N-(2-diethyloxyphosphorylethyl)aminodeoxyclavulanic acid;
9-N-[4-(sulphonato)butyl]aminodeoxyclavulanic acid;
9-N(2-phenylthioethyl)aminodeoxyclavulanic acid;
9-N-2[(N,N-dimethylsulphamoyl)benzylamino]ethylaminodeoxyclavulanic acid;
9-N-(2-methylsulphonamidoethyl)aminodeoxyclavulanic acid;
9-N-(3-methylsulphonamidopropyl)aminodeoxyclavulanic acid;
9-N-[2-(N-methyl)methylsulphonamidoethyl-]aminodeoxyclavulanic acid;
9-N-[2-[6β-(DL-2-Phenoxycarbonyl-2thien-3'-ylacetamido) penicillanoyloxy]ethyl]aminodeoxyclavulanic acid;
9-N-[2-[6β-(DL-2-Phenoxycarbonyl-2-thien-3-ylacetamido)penicillanoyloxy]ethyl]aminodeoxyclavulanic acid;
9-N-[2-[6β-(DL-2-Phenoxycarbonyl-2-thien-3'-ylacetamido)penicillanoyloxy]ethyl]-N-(2-methallyl-)aminodeoxyclavulanic acid;
9-N-[3-Imidazol-1-yl)propyl]aminodeoxyclavulanic acid;
9-N-(4,4-Diethoxybutyl)aminodeoxyclavulanic acid;
9-N-(4-Acetoxybutyl)aminodeoxyclavulanic acid;
9-N-[4-Methyl-4-nitropentyl]aminodeoxyclavulanic acid;
9-[N-benzyl-N-(N'N'-dimethylureido)ethyl]aminodeoxyclavulanic acid and 9-N-(N'N'-dimethylureido)ethylaminodeoxyclavulanic acid;
9-N-[2-(phenylsulphonyl)ethyl]aminodeoxyclavulanic acid;
9-N-(3-N-benzylcarbamoylprop-1-yl)aminodeoxyclavulanic acid;
9-N-(3-N-Benzylcarbamoyleth-1-yl)aminodeoxyclavulanic acid;
9-N-(2-Indol-3'-ylethyl)aminodeoxyclavulanic acid;
9-N-(2-chloro-2-phenylethyl)-aminodeoxyclavulanic acid; or 9-N-(2-carbamoylethyl)aminodeoxyclavulanic acid.

38. A method of treating bacterial infections in humans and animals which comprises administering to a human or animal in need thereof a synergistically effective amount of a compound of the formula (I):

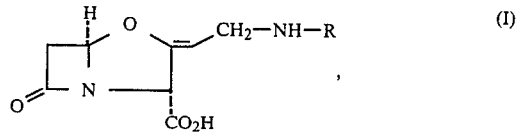

a pharmaceutically acceptable salt thereof or an in-vivo hydrolyzable ester thereof wherein R is alkyl of 2-12 carbon atoms or aralkyl of 2-6 carbon atoms in the alkyl moiety substituted on an alkyl carbon atom other than that adjacent to —NH— group, by 1—3 substituents selected from the group consisting of halo, non-aromatic heterocyclyl of 4-7 ring atoms unsubstituted or substituted by up to 3 substituents selected from the group consisting of halo; alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, said non-aromatic heterocyclyl being linked through carbon, an aromatic heterocyclyl of 4-7 ring atoms unsubstituted or substituted by up to 3 substituents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; nitro; oxo; —$OR^1$; $SR^1$; —$P(O)R^2R^3$; —$NR^4R^5$; =$NR^6$; and —$S(O)_nR^S$ wherein n is one or two and $R^S$ is hydroxy, hydrocarbyloxy or heterocyclyl of 4-7 ring atoms unsubstituted or substituted by alkyl of 1-6 carbon atoms, a heterocyclyl of 4-7 ring atoms, amino, alkanoylamino of 1-6 carbon atoms in the alkyl moiety, mono-, di- or trialkylamino of 1-6 carbon atoms in each alkyl group, hydroxy, alkoxy of 1-6 carbon atoms, mercapto, alkylthio of 1-6 carbon atoms, heterocyclylthio of 4-7 ring atoms, arylthio, sulphamoyl, carbamoyl, amidino, guanidino, nitro, chloro, bromo, fluoro, carboxy or a salt or ester thereof, alkanoyloxy of 1-6 carbon atoms in the alkyl moiety, arylcarbonyl or heterocyclylcarbonyl of 4-7 ring atoms; or $R^S$ is —$NR^TR^U$ wherein $R^T$ and $R^U$ are each hydrogen or a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo; or $R^T$ and $R^U$ together form the residue of a heterocyclic ring of 4-7 ring atoms; $R^1$ is hydrogen, a hydrocarbon of up to 18 carbon atoms unsubstituted or substituted by up to 3 substitutents selected from the group consisting of halo, alkyl of 1-6 carbon atoms, alkoxy of 1-6 carbon atoms, haloalkyl of 1-6 carbon atoms, hydroxy, amino, carboxy, alkoxycarbonyl of 1-6 carbon atoms in the alkoxy moiety, alkoxycarbonylalkyl of 1-6 carbon atoms in the alkoxy moiety and 1-6 carbon atoms in the alkyl moiety, aryl and oxo, heterocyclyl of 4–7 ring members, —COR$^H$, CO$_2$R$^H$ or CON(R$^H$)$_2$ wherein R$^H$ is hydrogen, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, or a heterocyclyl of 4–7 ring atoms, or two of said R$^1$ groups are joined to form a ring; R$^2$ and R$^3$ are each hydroxy, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, or carbyloxy; R$^4$ is hydrogen or a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo; R$^5$ is hydrogen, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, a heterocyclyl of 4–7 ring atoms, —COR$^H$, CO$_2$R$^H$ or CON(R$^H$)$_2$ wherein R$^H$ is hydrogen, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, or heterocyclyl of 4–7 ring atoms, or —S(O)$_n$R$^S$ wherein n and R$^S$ are as above defined; and R$^6$ is hydroxy, a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo, hydrocarbyloxy, amino, arylamino or —NHCONH$_2$; provided that a carbon atom of the group R which carries an oxo substituent does not carry a second substituent other than a group —NR$^4$R$^5$ and an antibacterially effective amount of a penicillin or cephalosporin, in combination with a pharmaceuticaly acceptable carrier.

39. A method according to claim 38 wherein when R is a substituted alkyl moiety, the alkyl moiety contains 2–6 carbon atoms and when R is a substituted aralkyl moiety, the aryl moiety is phenyl.

40. A method according to claim 38 wherein the hydrocarbon groups contain up to 10 carbon atoms.

41. A method according to claim 38 wherein the hydrocarbon groups contain up to 6 carbon atoms.

42. A method according to claim 38 wherein R is a substituted alkyl moiety wherein the alkyl moiety is ethyl.

43. A method according to claim 38 wherein R is alkyl of 2–6 carbon atoms or aralkyl of 2–6 carbon atoms in the alkyl moiety substituted by —OR$^1$ wherein OR$^1$ is alkoxy of 1–6 carbon atoms, alkanoyloxy of 1–6 carbon atoms in the alkyl moiety or a moiety of the formula (A):

$$R^oCONH \begin{array}{c} R^z \\ \vdots \\ \end{array} \begin{array}{c} S \\ \\ N \\ CO-O- \end{array} \qquad (A)$$

wherein R$^o$CONH is an organic acylamino moiety of an antibacterialy active penicillin and R$^z$ is hydrogen or methoxy.

44. A method according to claim 38 wherein R is alkyl of 2–6 carbon atoms substituted by NR$^4$R$^5$ wherein NR$^4$R$^5$ is amino, alkoxycarbonylamino of 1–6 carbon atoms in the alkoxy moiety, alkylsulphoylamido of 1–6 carbon atoms in the alkyl moiety of alkylureidoamino of 1–6 carbon atoms in the alkyl moiety.

45. A method according to claim 38 wherein R is alkyl of 2–6 carbon atoms substituted by —S(O)$_n$R$^S$ wherein n is one or two and R$^S$ is hydroxy, hydrocarbyloxy or heterocyclyl moiety or 4–7 ring atoms unsubstituted or substituted by alkyl of 1–6 carbon atoms, a heterocyclyl of 4–7 ring atoms, amino, alkanoylamino of 1–6 carbon atoms in the alkyl moiety, mono-, di- or trialkylamino of 1–6 carbon atoms in each alkyl group, hydroxy, alkoxy of 1–6 carbon atoms, mercapto, alkylthio of 1–6 carbon atoms, heterocyclylthio of 4–7 ring atoms, arylthio, sulphamoyl, carbamoyl, amidino, guanidino, nitro, chloro, bromo, fluoro, carboxy or a salt or ester thereof, alkanoyloxy of 1–6 carbon atoms in the alkyl moiety, arylcarbonyl or heterocyclylcarbonyl of 4–7 ring atoms; or R$^S$ is —NR$^T$R$^U$ wherein R$^T$ and R$^U$ are each hydrogen or a hydrocarbon of up to 18 carbon atoms unsubstituted or substituted by up to 3 substitutents selected from the group consisting of halo, alkyl of 1–6 carbon atoms, alkoxy of 1–6 carbon atoms, haloalkyl of 1–6 carbon atoms, hydroxy, amino, carboxy, alkoxycarbonyl of 1–6 carbon atoms in the alkoxy moiety, alkoxycarbonylalkyl of 1–6 carbon atoms in the alkoxy moiety and 1–6 carbon atoms in the alkyl moiety, aryl and oxo; or R$^T$ and R$^U$ together form the residue of a heterocyclic ring of 4–7 ring atoms.

46. A method according to claim 38 wherein the compound is:

9N-(2,2-dimethoxyethyl)aminodeoxyclavulanic acid;
9-N-(2-chloroethyl)aminodeoxyclavulanic acid;
9-N-[2(N-methoxycarbonylamino)ethyl]amino-9-deoxyclavulanic acid;
9-N-(2-pyrid-2'-ylethyl)aminodeoxyclavulanic acid;
9-N-(2-pyrid-4'-ylethyl)aminodeoxyclavulanic acid;
9-N(2-methoxyethyl)aminodeoxyclavulanic acid;
9-N-[(N'-benzyl-N'-methylsulphonamido)ethyl]aminodeoxyclavulanic acid;
9-N-(2-diethyloxyphosphorylethyl)aminodeoxyclavulanic acid;
9-N-[4-(sulphonato)butyl]aminodeoxyclavulanic acid;

9-N(2-phenylthioethyl)aminodeoxyclavulanic acid;
9-N-2](N,N-dimethylsulphamoyl)benzylamino]ethylaminodeoxyclavulanic acid;
9-N-(2-methylsulphonamidoethyl)aminodeoxyclavulanic acid;
9-N-(3-methylsulphonamidopropyl)aminodeoxyclavulanic acid;
9-N-[2-(N-methyl)methylsulphonamidoethyl]aminodeoxyclavulanic acid;
9-N-[2-[6β-(DL-2-Phenoxycarbonyl-2-thien-3'-ylacetamido)penicillanoyloxy]ethyl]aminodeoxyclavulanic acid;
9-[2-[6β-(DL-2-Phenoxycarbonyl-2-thien-3-ylacetamido)penicillanoyloxy]ethyl]aminodeoxyclavulanic acid;
9-N-[2-[6β-(DL-2-Phenoxycarbonyl-2-thien-3'-ylacetamido)penicillanoyloxy]ethyl]-N-(2-methallyl)aminodeoxyclavulanic acid;
9-N-[3-Imidazol-1-yl)propyl]aminodeoxyclavulanic acid;
9-N-(4,4-Diethoxybutyl)aminodeoxyclavulanic acid;
9-N-(4-Acetoxybuyl)aminodeoxyclavulanic acid;
9-N-[4-Methyl-4-nitropentyl]aminodeoxyclavulanic acid;
9-[N-benzyl-N-(N'N'-dimethylureido)ethyl]aminodeoxyclavulanic acid and 9-N-(N'N'-dimethylureido)ethylaminodeoxyclavulanic acid;
9-N-[2-(phenylsulphonyl)ethyl]aminodeoxyclavulanic acid;
9-N-(3-N-benzylcarbamoylprop-1-yl)aminodeoxyclavulanic acid;
9-N-(3-N-Benzylcarbamoyleth-1-yl)aminodeoxyclavulanic acid;
9-N-(2-Indol-3'-ylethyl)aminodeoxyclavulanic acid;
9-N-(2-chloro-2-phenylethyl)-aminodeoxyclavulanic acid; or
9N-(2-carbamoylethyl)aminodeoxyclavulanic acid.

* * * * *